US009907851B2

(12) United States Patent
Yum et al.

(10) Patent No.: US 9,907,851 B2
(45) Date of Patent: Mar. 6, 2018

(54) COMPOSITIONS WITH A RHEOLOGICAL MODIFIER TO REDUCE DISSOLUTION VARIABILITY

(71) Applicant: Durect Corporation, Cupertino, CA (US)

(72) Inventors: Su Il Yum, Los Altos, CA (US); Wendy Chao, San Jose, CA (US); Huey-Ching Su, San Jose, CA (US); Roger Fu, Saratoga, CA (US); Michael S. Zamloot, Austin, TX (US); Karl Bratin, Groton, CT (US); Ravi M. Shanker, Groton, CT (US)

(73) Assignee: Durect Corporation, Cupertino, CA (US)

(*) Notice: Subject to any disclaimer, the term of this patent is extended or adjusted under 35 U.S.C. 154(b) by 0 days.

(21) Appl. No.: 15/380,828

(22) Filed: Dec. 15, 2016

(65) Prior Publication Data
US 2017/0196978 A1 Jul. 13, 2017

Related U.S. Application Data

(63) Continuation of application No. 14/214,057, filed on Mar. 14, 2014, now Pat. No. 9,555,113.

(60) Provisional application No. 61/801,110, filed on Mar. 15, 2013.

(51) Int. Cl.
A61K 31/485 (2006.01)
A61K 31/4458 (2006.01)
A61K 31/137 (2006.01)
A61K 47/02 (2006.01)
A61K 47/14 (2017.01)
A61K 47/26 (2006.01)
A61K 47/38 (2006.01)

(52) U.S. Cl.
CPC ............ A61K 47/02 (2013.01); A61K 31/485 (2013.01); A61K 47/14 (2013.01); A61K 47/26 (2013.01); A61K 47/38 (2013.01)

(58) Field of Classification Search
CPC .... A61K 31/485; A61K 9/4816; A61K 9/485; A61K 47/38; A61K 47/14; A61K 47/26; A61K 47/02
See application file for complete search history.

(56) References Cited

U.S. PATENT DOCUMENTS

| | | |
|---|---|---|
| 2,799,241 A | 7/1957 | Wurster |
| 2,931,802 A | 4/1960 | Toney et al. |
| 3,339,546 A | 9/1967 | Chen |
| 3,743,398 A | 7/1973 | Johnson et al. |
| 3,845,770 A | 11/1974 | Theeuwes et al. |
| 3,853,837 A | 12/1974 | Fujino et al. |
| 3,916,889 A | 11/1975 | Russell |
| 3,916,899 A | 11/1975 | Theeuwes et al. |
| 3,952,741 A | 4/1976 | Baker |
| 3,992,365 A | 11/1976 | Beddell et al. |
| 3,995,631 A | 12/1976 | Higuchi et al. |
| 4,008,719 A | 2/1977 | Theeuwes et al. |
| 4,014,334 A | 3/1977 | Theeuwes et al. |
| 4,016,880 A | 4/1977 | Theeuwes et al. |
| 4,024,248 A | 5/1977 | Konig et al. |
| 4,063,064 A | 12/1977 | Saunders et al. |
| 4,088,864 A | 5/1978 | Theeuwes et al. |
| 4,100,274 A | 7/1978 | Dutta et al. |
| 4,111,202 A | 9/1978 | Theeuwes |
| 4,160,020 A | 7/1979 | Ayer et al. |
| 4,327,725 A | 5/1982 | Cortese et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,578,075 A | 3/1986 | Urquhart et al. |
| 4,622,219 A | 11/1986 | Haynes |
| 4,681,583 A | 7/1987 | Urquhart et al. |
| 4,681,765 A | 7/1987 | Guley |
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |

(Continued)

FOREIGN PATENT DOCUMENTS

| | | |
|---|---|---|
| AU | 8374575 | 8/1975 |
| CA | 2222567 | 1/2002 |

(Continued)

OTHER PUBLICATIONS

"New Drugs/Programs"; *Current Drug Discovery;* Nov. 2004; pp. 7-10.
"Ritalin product monograph"; *CPS Compendium of Pharmaceuticals and Specialties,* 34th ed.; Gillis, M., Ed. Canadian Pharmacists Association: Ottawa, (1999); pp. 1573-1574.
3M, "3M DDS Announces Development of New HFA-Compatible Exipients: Novel Oligomeric Acids as MDI Suspension Aid and Solubilizers" *3M Delivery Newsletter,* vol. 15, *3M Drug Delivery Systems;* Jun. 2000, pp. 9-11.
Abdul-Fattah, Ahmad M., et al; "Preparation and In Vitro Evaluation of Solid Dispersions of Halofantrine."; *International Journal of Pharmaceutics* 235; (2002); pp. 17-33.

(Continued)

Primary Examiner — Johann R Richter
Assistant Examiner — Genevieve S Alley
(74) Attorney, Agent, or Firm — Michael B. Rubin; Bozicevic, Field & Francis LLP

(57) ABSTRACT

The present disclosure provides compositions (e.g., extended release compositions) which exhibit a desirable pharmacokinetic profile of an active agent while providing reduced dissolution sample variability, e.g., in the form of reduced inter-capsule variability and/or a reduction in storage-time dependent change in mean release of the active agent from the composition. Related methods of making and administering the disclosed compositions and formulations are also provided.

11 Claims, 41 Drawing Sheets

(56) References Cited

U.S. PATENT DOCUMENTS

| | | |
|---|---|---|
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |
| 4,938,763 A | 7/1990 | Dunn et al. |
| 4,957,681 A | 9/1990 | Klimesch et al. |
| 4,957,744 A | 9/1990 | della Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,280 A | 4/1998 | Mooney, III et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Heafield et al. |
| 5,908,850 A | 6/1999 | Zeitlin et al. |
| 5,919,473 A | 7/1999 | Elkhoury |
| 5,932,597 A | 8/1999 | Brown |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |
| 6,245,351 B1 | 6/2001 | Nara et al. |
| 6,291,013 B1 | 9/2001 | Gibson et al. |
| 6,294,195 B1 | 9/2001 | Oshlack et al. |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,919,373 B1 | 7/2005 | Lam et al. |
| 6,921,541 B2 | 7/2005 | Chasin et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 | 11/2010 | Gibson et al. |
| 7,838,522 B2 | 11/2010 | Esposito et al. |
| 8,124,123 B2 | 2/2012 | Pillai et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,163,798 B2 | 4/2012 | Gupta et al. |
| 8,168,217 B2 | 5/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,945,614 B2 | 2/2015 | Yum et al. |
| 8,951,556 B2 | 2/2015 | Yum et al. |
| 8,974,821 B2 | 3/2015 | Yum et al. |
| 9,233,160 B2 | 1/2016 | Yum et al. |
| 9,517,271 B2 | 12/2016 | Yum et al. |
| 9,555,113 B2 | 1/2017 | Yum et al. |
| 9,592,204 B2 | 3/2017 | Yum et al. |
| 2001/0000522 A1 | 4/2001 | Dyer et al. |
| 2001/0029257 A1 | 10/2001 | Murdock et al. |
| 2001/0047005 A1 | 11/2001 | Farrar et al. |
| 2001/0055613 A1 | 12/2001 | Burnside et al. |
| 2002/0086878 A1 | 7/2002 | Dobrozsi et al. |

(56) References Cited

U.S. PATENT DOCUMENTS

| | | |
|---|---|---|
| 2002/0114835 A1 | 8/2002 | Sackler et al. |
| 2002/0143065 A1 | 10/2002 | Liu et al. |
| 2003/0004177 A1 | 1/2003 | Kao et al. |
| 2003/0045454 A1 | 3/2003 | Okumu et al. |
| 2003/0152637 A1 | 8/2003 | Chasin et al. |
| 2003/0157168 A1 | 8/2003 | Breder et al. |
| 2003/0165562 A1 | 9/2003 | Gutierrez-Rocca et al. |
| 2003/0185873 A1 | 10/2003 | Chasin et al. |
| 2003/0191147 A1 | 10/2003 | Sherman et al. |
| 2004/0001889 A1 | 1/2004 | Chen et al. |
| 2004/0024021 A1 | 2/2004 | Sudo et al. |
| 2004/0052336 A1 | 3/2004 | Langlet et al. |
| 2004/0101557 A1 | 5/2004 | Gibson et al. |
| 2004/0109893 A1 | 6/2004 | Chen et al. |
| 2004/0138237 A1 | 7/2004 | Shah |
| 2004/0146562 A1 | 7/2004 | Shah |
| 2004/0161382 A1 | 8/2004 | Yum et al. |
| 2004/0224020 A1 | 11/2004 | Schoenhard |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0158382 A1 | 7/2005 | Cruz et al. |
| 2005/0171052 A1 | 8/2005 | Cook et al. |
| 2005/0208132 A1 | 9/2005 | Sathyan et al. |
| 2005/0232876 A1 | 10/2005 | Minga et al. |
| 2005/0244489 A1 | 11/2005 | Paris |
| 2005/0260264 A1 | 11/2005 | Edgren et al. |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0104909 A1 | 5/2006 | Vaghefi et al. |
| 2006/0115527 A1 | 6/2006 | Hassan et al. |
| 2006/0165800 A1 | 7/2006 | Chen et al. |
| 2006/0210599 A1 | 9/2006 | Gibson et al. |
| 2007/0027105 A1 | 2/2007 | Junnarkar et al. |
| 2007/0031502 A1 | 2/2007 | Pettersson et al. |
| 2007/0104763 A1 | 5/2007 | Jobdevairakkam et al. |
| 2007/0259033 A1 | 11/2007 | Cruz |
| 2008/0023261 A1 | 1/2008 | Kaneko et al. |
| 2008/0026052 A1 | 1/2008 | Schoenhard |
| 2008/0145419 A1 | 6/2008 | Gibson et al. |
| 2008/0152708 A1 | 6/2008 | Gibson et al. |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0164240 A1 | 6/2009 | Friedmann et al. |
| 2009/0165578 A1 | 7/2009 | Zamloot et al. |
| 2009/0169631 A1 | 7/2009 | Zamloot et al. |
| 2009/0215808 A1 | 8/2009 | Yum et al. |
| 2010/0260844 A1 | 10/2010 | Scicinski et al. |
| 2011/0287093 A1 | 11/2011 | Schoenhard |
| 2012/0135072 A1 | 5/2012 | Yum et al. |
| 2012/0135073 A1 | 5/2012 | Yum et al. |
| 2012/0165358 A1 | 6/2012 | Cruz et al. |
| 2013/0281480 A1 | 10/2013 | Yum et al. |
| 2013/0287845 A1 | 10/2013 | Yum et al. |
| 2013/0295168 A1 | 11/2013 | Yum et al. |
| 2013/0309176 A1 | 11/2013 | Port et al. |
| 2013/0337059 A1 | 12/2013 | Yum et al. |
| 2013/0337060 A1 | 12/2013 | Yum et al. |
| 2014/0011842 A1 | 1/2014 | Scicinski et al. |
| 2014/0275147 A1 | 9/2014 | Yum et al. |
| 2015/0196644 A1 | 7/2015 | Yum et al. |
| 2016/0038479 A1 | 2/2016 | Yum et al. |
| 2016/0038592 A1 | 2/2016 | Yum et al. |
| 2016/0058746 A1 | 3/2016 | Scicinski et al. |
| 2016/0136102 A1 | 5/2016 | Yum et al. |
| 2017/0252330 A1 | 9/2017 | Scicinski |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0635531 | 2/1995 |
| EP | 0640336 | 3/1995 |
| EP | 0711548 | 5/1996 |
| EP | 0773034 | 5/1997 |
| EP | 0778768 | 6/1997 |
| EP | 0537559 | 1/1998 |
| EP | 1010436 | 6/2000 |
| EP | 0782569 | 3/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 2003508449 | 3/2003 |
| WO | WO 1990003768 | 4/1990 |
| WO | WO 1990003809 | 4/1990 |
| WO | WO 1991018016 | 11/1991 |
| WO | WO 199214466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 2000000120 | 1/2000 |
| WO | WO 2000016750 | 3/2000 |
| WO | WO 2000078335 | 12/2000 |
| WO | WO 2001008661 | 2/2001 |
| WO | WO 2001015734 | 3/2001 |
| WO | WO 2001051024 | 7/2001 |
| WO | WO 2001076599 | 10/2001 |
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |

(56) References Cited

FOREIGN PATENT DOCUMENTS

| | | |
|---|---|---|
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004054542 | 7/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | 2006134018 | 12/2006 |
| WO | WO 2007058923 | 5/2007 |
| WO | 2007070632 | 6/2007 |
| WO | 2007135193 | 11/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2009088414 | 7/2009 |
| WO | WO 2013142279 | 9/2013 |
| WO | WO 2014144984 | 3/2014 |
| WO | WO 2014144975 | 9/2014 |

OTHER PUBLICATIONS

Adams, Edgar G, et al.; "A comparison of the abuse liability of tramadol, NSAIDS, and hydrocodone in patients with chronic pain"; *Journal of Pain and Symptom Management.* 31(5); (2006); pp. 465-476.

Ajayaghosh, A., et al., "Solid-Phase Synthesis of N-Methyl- and N-Ethylamides of Peptides Using Photolytically Detachable ((3-Nitro-4-((alkylamino)methyl)benzamido)methyl)polystyrene Resin"; *J. Org. Chem.* 55; (1990); pp. 2826-2829.

Allahham Allahham, et al; "Flow and injection characteristics of pharmaceutical parenteral formulations using a micro-capillary rheometer"; *International Journal of Pharmaceutics.* 270; (2004); pp. 139-148.

Ansel, H.C. et al.; *Pharmaceutical Dosage Forms and Drug Delivery System,* sixth ed., (1995); 20 pages.

Ash Michael and Ash Irene; "Handbook of Pharmaceutical Additives: An International Guide to More Than 6000 Products by Trade Name, Chemical, Function, and Manufacturer" ; *Gower* (1995); 3 pages.

Aungst, B.J., et al; "Improved Oral Bioavailability of an HIV Protease Inhibitor Using Gelucire 44/14 and Labrasol Vehicles"; *Bulletin Technique Gattefosse,* No. 87; (1994); pp. 49-54.

Aungst, B.J., et al; "Amphiphilic vehicles improve the oral bioavailability of a poorly soluble HIV Protease inhibitor at high doses."; *International Journal of Pharmaceutics,* vol. 156; (1997); pp. 79-88.

Bansal, Tripta, et al; "Solid Self Nanoemulsifying Delivery Systems as a Platform Technology for Formulation of Poorly Soluble Drugs"; *Critical Reviews™ in Therapeutic Drug Carrier Systems,* 25(1); (2008); pp. 63-116.

Barakat, N.S.; "Etodolac-Liquid-Filled Dispersion into Hard Gelatin Capsules: An Approach to Improve Dissolution and Stability of Etodolac Formulation"; *Drug Development and Indistrial Pharmacy.* 32; (2006); pp. 865-876.

Barb, R., et al.; "Evaluation of the Saber Delivery System for the Controlled Release of Deslorelin: Effect of Dose in Estrogen Primed Ovarectomized Gilts"; *Proceed Int'l, Symp. Control. Rel. Bioact. Mater.;* (1999) Controlled Release Society, Inc.; pp. 1170-1171.

Barker S.A., et al; "An investigation into the structure and bioavailability of α-tocopherol dispersions in Gelucire 44/14"; *Journal of Controlled Release 91;* (2003); pp. 477-488.

Becker & Johnson "Effects of Gonadotropin-Releasing Hormone Infused in a Pulsatile or Continuous Fashion Serum Gonadotropin Concentrations and Ovulation in the Mare"; *J. Anim. Sci.* vol. 70; (1992);. pp. 1208-1215.

Bekersky I, et al.; "Effect of low- and high-fat meals on tacrolimus absorption following 5 mg single oral doses to healthy human subjects"; *J Clin Pharmacol;* 41; (2001); pp. 176-182.

Berge et al. "Pharmaceutical salts" *J Pharm. Sci.* 66(1); Jan. 1977; pp. 1-19.

Betschart, R., et al.; "Evaluation of the SABER™ Delivery System for the Controlled Release of the GnRH Analogue Deslorelin for Advancing Ovulation in Mares: Effect of Gamma Radiation"; *Proceed. Int'l. Symp. Control. Rel. Bioact. Mater.,* 25, Controlled Release Society Inc.; (1998); pp. 655-656.

Blachez, P., et al; "Development of immediate release pellets of poorly soluble compounds using Gelucire® 44/14 using melt pelletization"; Poster, Conference *"AAPS Annual Meeting & Exposition";* Salt Lake City, Utah, United States; Oct. 26, 2003; 2 pages.

Blažková, A. et al; "Viscosity properties of aqueous solutions of hydroxyethylcellulose"; *Chem Papers* 44(3); (1990); pp. 289-301.

Brevard J, et al. "Pain and opioid abuse in a population of substance abuse patients: data from the Navippro™ system." *Conference paper presented at the 42nd American Pain Society (APS) Annual Scientific Meeting,* Washington D.C.; (2007); 1 page.

Bühler, K.; GnRH Agonists and Safety, In GnRH Analagoues The State of the Art 1993, A Summary of the 3rd International Symposium on GnRH Analogues in Cancer and Human Reproduction, Geneva, Feb. 1993; pp. 139-146.

Burns, P. et al.; "Pharmacodynamic Evaluation of the Saber™ Delivery System for the Controlled Release of the GnRH Analogue Deslorelin Acetate for Advancing Ovulation in Cyclic Mares"; *Proceed. Int'l. Symp. Control. Rel. Bioact. Mater.,* 24; Controlled Release Society Inc. (1997); 4 pages.

"Cab-O-Sil® , Untreated Fumed Silica: Properties & Functions"; Cabot Corporation, Cab-O-Sil Division; (1993); pp. 1-34.

Carraway, et al.; "Drug Delivery From a Controlled Release Aerosol: Effects of Formulation Variables"; *AAPS J Abstract. Southern BioSystems, Inc.,* Birmingham AL, USA; (2000); 1 page.

Carraway, et al.; "Drug Release from a Novel Controlled Release Aerosol Based on Sucrose Acetate Isobutyrate" *AAPS Midwest Regional Meeting Chicago,* IL; May 22, 2000; 2 pages.

Cellulose Acetate Butyrate. In: European pharmacopoeia. 4 edn. Strasbourg Cedex, France: Council of Europe; (2001); pp. 853-854.

Chambin, O.; et al; "Interest of Multifunctional Lipid Excipients: Case of Gelucire® 44/14"; *Drug Development and Industrial Pharmacy,* 31; (2005); pp. 527-534.

Chambin, O., et al; "Influence of drug polarity upon the solid-state structure and release properties of self-emulsifying drug delivery systems in relation with water affinity"; *Colloids and Surfaces B: Biointerfaces* 71; (2009); pp. 73-78.

Chauhan, Bhaskar, et al; "Preparation and Characterization of Etoricoxib Solid Dispersions Using Lipid Carriers by Spray Drying Technique"; *AAPS PharmSciTech* ; 6(3), Article 50; (http://www.aapspharmscitech.org); (2005); pp. E405-E412.

Chauhan, B., et al; "Preparation and evaluation of glibenclamide-polyglycolized glycerides solid dispersions with silicon dioxide by spray drying technique"; *European J. Pharm. Sci.* 26(2); (2005); pp. 219-230.

Chen, X. Q., et al; "Evaluation of Lipid-Based Formulations in Dogs and Monkeys for a Highly Lipophilic Compound"; Conference *Annual Meeting of AAPS;* (2007); San Diego, CA; poster abstract; 1 page.

Coy, et al.; "Solid Phase Synthesis of Lutenizing Hormone-Releasing Hormone and Its Analogs"; *Methods Enzymol.* 37; (1975); pp. 416-424.

Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences,* vol. 97 No. 2; Feb. 2008; pp. 995-1012; article first published online Dec. 6, 2007.

(56) References Cited

OTHER PUBLICATIONS

Damian, Festo, et al; "Physicochemical characterization of solid dispersions of the antiviral agent UC-781 with polyethylene glycol 6000 and Gelucire 44/14"; *European Journal of Pharmaceutical Sciences* 10; (2000); pp. 311-322.

Darling, et al. (2000) "Extended Release of Human Growth Hormone Suspended in Saber™ Formulation Design and in Vitro Assessment" Genentech, Inc., South San Francisco, CA USA and Southern BioSystems, Inc. Birmingham AL, USA. Poster; 1 page.

DataRase WPI SECTION Ch, Week 198532 Derwent Publications Ltd., London GB; Class B07, AN 1985-193549 XP002284488 & JP 60120811 A (Sealer, R P KK) Jun. 28, 1985 (Abstract).

Desai et al.; "Surface Modification of Polymeric Biomaterials for Reduced Thrombogenicity"; *Polym. Mater. Sci. Eng.*, 62; Jun. 1990;. pp. 731-735.

Dodson, K.M., et al. "Oral Controlled Release of Antiretrovirals Using the Saber Delivery System Incorporated into Soft Gelatin Capsules", *AAPS Meeting*, (1999), New Orleans, LA.; 2 pages.

Dordunoo, S.K., et al; "Preformulation Studies on Solid Dispersions Containing Triamterene or Temazepam in Polyethylene Glycols or Gelucire 44/14 for Liquid Filling of Hard Gelatin Capsules"; *Drug Development and Industrial Pharmacy*, vol. 17, No. 12; (1991); pp. 1685-1713.

Dordunoo, Stephen K., et al; "Solidification studies of polyethylene glycols, Gelucire® 44/14 or their dispersions with Triamterene or Temazepam"; *Journal of Pharm. Pharmacology* 48; (1996); pp. 782-789.

Duan, D.C. et al.; "Novel Dispersing Aids for Hydrofluoroalkane-Based Metered Dose Inhalers"; *1998 Conference of the American Association of Pharmaceutical Scientists*, San Francisco, California; Nov. 1998; 1 page.

Duan, D.C. et al., "Oligomeric Lactic Acids as Solubilizing Aids for HFA-Based Metered Dose Inhalers"; *1998 Conference of the American Association of Pharmaceutical Scientists*, San Francisco, California; Nov. 1998; 1 page.

Dunbar SA, Katz NP; "Chronic opioid therapy for nonmalignant pain in patients with a history of substance abuse: report of 20 cases." *Journal of Pain and Symptom Management*. 11(3); (1996) pp. 163-171.

Edimo, A., et al; "Capacity of Lipophilic Auxiliary Substances to Give Spheres by Extrusion—Spheronization"; *Drug Development and Industrial Pharmacy*, 19(7); (1993); pp. 827-842.

Eliasen, Helle, et al; "Effects of binder rheology on melt agglomeration in a high shear mixer"; *International Journal of Pharmaceutics* 176; (1998); pp. 73-83.

Fernandez, Sylvie, et al; "Lipolysis of the semi-solid self-emulsifying excipient Gelucire® 44/14 by digestive lipases"; *Biochimica et Biophysica Acta* 1781; (2008); pp. 367-375; available online Jun. 3, 2008.

Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season"; *Am. J. Vet. Res.*, vol. 54, No. 10; Oct. 1993; pp. 1746-1751.

Fleury, J., et al., "Evaluation of the Saber Delivery System for the Controlled Release of Deslorelin for Advancing Ovulation in the Mare: Effects of Formulation & Dose", *Proceed Int'l Symp. Control. Rel. Bioact. Mater.*, 25; (1998); Controlled Release Society, Inc.; pp. 657-658.

Friedmann N, Klutzaritz V, Webster L.; "Efficacy and safety of an extended-release oxycodone (Remoxy) formulation in patients with moderate to severe osteoarthritic pain"; *J. Opioid Manag.* 7(3); (2011); pp. 193-202.

Friedmann N, Klutzaritz V, Webster L.; "Long-term safety of Remoxy(R) (extended-release oxycodone) in patients with moderate to severe chronic osteoarthritis or low back pain"; *Pain Med.* 12(5); (2011); pp. 755-760.

Gad, Shayne C., et al; "Nonclinical Vehicle Use in Studies by Multiple Routes in Multiple Species"; *International Journal of Toxicology*, 25; Sep. 20, 2006; pp. 1-23.

Gattefossé Corporation (1989); "To Help With Your Impossible Formulations: A Guide to Gattefossé Liquid Excipients"; 6 pages.

Gattefossé (1998); "Oral Route Excipients"; 8 pages.

Gelucire® 44/14 brochure (1999); "Immediate Release and Enhanced Bioavailability"; pp. 1-16.

Gelucire® Technical Dossier; "Answering The Need for Enhanced Bioavailability"; Oct. 1996; 16 pages.

Gelucire® (1996); "Answering The Need for Enhanced Bioavailability"; 5 pages

"General Characteristics of Polymers"; Museum of Fine Arts, Boston; (2007); pp. 1-4.

Gibson, et al.; "Effects of Formulation Variables on Controlled Release of Paclitaxel and other Chemotherapeutic Agents from a Novel Delivery System" *AAPS* New Orleans, LA; (1999); Southern BioSystems, Inc. Birmingham AL, USA; 2 pages.

Gibson, et al.; "In Vitro and In Vivo Evaluation of a Novel In Situ-Forming Pareteral Delivery System"; *Meeting of Recent Advances in Drug Delivery Systems*, Salt Lake City, UT; (1999); Southern BioSystems, Inc. Birmingham AL, USA; 2 pages.

Gilderman L., et al; "Remoxy™: A New Opioid Drug With Effective Analgesia and Abuse-Resistance." *American Pain Society Annual Meeting*, San Antonio, TX, May 2006; 1 page.

Ginther, O.J.; "Follicles"; *Ultrasonic Imaging and Reproductive Events in the Mare EquiServices*, Chapter 4; Cross Plains, WI; (1986); pp. 43-72.

Ginther, O.J., "Effect of a Synthetic Gonadotropin-Releasing Hormone on Plasma Concentrations of Luteinizing Hormone in Ponies", *Am. J. Vet. Res.*, 1 vol. 35, No. X; Jan. 1974; pp. 79-78.

Ginther, O.J., "Reproductive Efficiency", *Reproductive Biology of the Mare Basic and Applied Aspects*, Second Ed., Chapter 12; (1992); pp. 499-509.

Glajchen, M.; "Chronic Pain: Treatment Barriers and Strategies for Clinical Practice."; *J AM Board Fam Pract.;* 14(3); (2001); pp. 212-218.

González et al; "Methylphenidate bioavailability from two extended-release formulations"; *International Journal of Clinical Pharmacology Therapeutics*, vol. 40, No. 4; (2002) pp. 175-184.

Gould, Phillip L.; "Salt selection for basic drugs"; *International Journal of Pharmaceutics*, 33 (1986); pp. 201-217.

Greydanus, D. E.; "Psychopharmacology for ADHD in Adolescents: Quo Vadis?"; *Psychiatric Times* vol. 20, No. 5; May 5, 2003; pp. 1-7.

Handbook of Pharmaceutical Excipients: Sixth Edition; "Medium-chain Triglycerides"; *Pharmaceutical Press and American Pharmacists Association* 2009; pp. 429-431.

Harrison, L.A., et al.; "Comaprison of HCG, Buserelin and Luprostiol for Induction of Ovulation in Cycling Mares"; *Equine Veterinary Science*, vol. II, No. 3; (1991); pp. 163-166.

Hatakeyama et al.; "Synthesis and physical properties of polyurethanes from saccharide-based polycaprolactones"; *Macromolecular Symposia*, vol. 130; (1998); pp. 127-138.

Hauss, David J., et al; "Lipid-Based Delivery Systems for Improving the Bioavailability and Lymphatic Transport of a Poorly Water-Soluble $LTB_4$ Inhibitor"; *Journal of Pharmaceutical Sciences*, vol. 87, No. 2; Feb. 1998; pp. 164-169; published online Jan. 7, 1998.

Hays Lon R.; "A profile of OxyContin addiction"; *Journal of Addictive Diseases* 23(4); (2004); pp. 1-9.

He, Y. et al. "Oral Formulation of a Novel Antiviral Agent, PG301029, in a Mixture of Gelucire 44/14 and DMA (2:1, wt/wt)"; *AAPS Pharm. Sci. Tech.* 6(1); (2005); pp. E1-E5.

Henry, C.; "Sucrose Acetate Isobutyrate Special Grade for Beverage Applications" *International Food Ingred;* (1995); pp. 47-49.

Hoskin PJ, et al; "The bioavailability and pharmacokinetics of morphine after intravenous, oral and buccal administration in healthy volunteers."; *Br J Clin Pharmacol;* 27 (4); (1989); pp. 499-505.

Hülsmann, S., et al; "Melt extrusion—an alternative method for enhancing the dissolution rate of 17β-estradiol hemihydrate"; *European Journal of Pharmaceutics and Biopharmaceutics* 49; (2000); pp. 237-242.

(56) References Cited

OTHER PUBLICATIONS

Hyland, J.H., et al.; "Infusion of Gonadotrophin-releasing hormone (GnRH) Induces Ovulation and Fertile Oestrus in Mares During Seasonal Anoestrus"; *J. Reprod. Fert., Suppl.* 35 (1987); pp. 211-220.
Inciardi James A, et al; "Mechanisms of prescription drug diversion among drug-involved club- and street-based populations"; *Pain Medicine.* 8(2), (2007); pp. 171-183.
Irvine, D.S., et al; "Duration of Oestrus and Time of Ovulation in Mares Treated with Synthetic GnRH (Ay24,031)"; *J. Reprod. Fert. Supp.* 23; (1975); pp. 279-283.
Irvine; "GnRH Clinical Application"; *In Equine Reproduction,* ; (eds) McKinon, A.O. and Voss, J.L., Chapter 36 , Lea & Febiger; (1993); pp. 41-45.
Ishida T, Oguri K, et al; "Isolation and identification of urinary metabolites of oxycodone in rabbits"; *Drug Metab Dispos;* 7(3); (1979); pp. 162-165.
Ishida T, Oguri K, Yoshimura H.; "Determination of oxycodone metabolites in urines and feces of several mammalian species"; *J Pharmacobiodyn;* 5(7); (1982); pp. 521-525.
Itoh, K., et al; "Improvement of physiochemical properties of N-4472 part I formulation design by using self-microemulsifying system"; *Int .J. Pharm.,* 238); (2002); pp. 153-160.
Iwanaga, Kazunori, et al; "Disposition of Lipid-Based Formulation in the Intestinal Tract Affects the Absorption of Poorly Water-Soluble Drugs"; *Biol. Pharm. Bull.* vol. 29, No. 3; (2006); pp. 508-512; published online Dec. 5, 2005.
Iyakuhin Tenkabutsu Kenkyykai Ed.; "Jitsuyo Iyakuhin Tenkabutsu (Practical Medical Additives)"; pub. Kagaku Kogyo-sha; Mar. 5, 1974; Tokyo; 6 pages.
Jannin, V., et al; "Systemes auto-émulsionnables et emulsions séches"; *STP Pharma Pratiques,* vol. 15, No. 3; May/Jun. 2005; pp. 246-255.
Jannin, V., et al; "Approaches for the development of solid and semi-solid lipid-based formulations"; *Advanced Drug Delivery Reviews* 60; (2008); pp. 734-746; available online Nov. 4, 2007.
Japanese Office Action for Japanese Application No. 2010-537128, dated Jun. 5, 2013.
Jöchle, W., et al.; "Control of Ovulation in the Mare with Ovuplant a Short-Term Release Implant (STI) Containing the GnRH Analogue Deslorelin Acetate: Studies from 1990 to 1994"; *Journal of Equine Veterinary Science,* vol. 14m No. 12; (1994); pp. 632-644.
Johnson, et al; "Biodegradable Delivery Systems for Estradiol: Comparison Between Poly(DL-Lactide) Microspheres and the Saber Delivery System"; *Proceed. Int'l Symp. Control. Rel. Bioact. Mater.,* 26; Controlled Release Society, Inc.; (1999); 1 page.
Johnson, R.M., et al; "Applications of Continuous Site-Directed Drug Delivery"; *Proc. West Pharmacol Soc.* vol. 45; (2002); pp. 219-222.
Johnston Lloyd D, et al; "Monitoring the future. National results on adolescent drug use: overview of key findings"; (NIH Publication No. 05-5726). Bethesda, MD: National Institute on Drug Abuse; (2004); pp. 1-66.
Kaiko; "Pharmacology of Tablets of Oxycontin the Development Process Thereof"; *Palliative Care Research* 7(1); (2005); pp. 3-13.
Kale, A., et al; "Design and Evaluation of Self-Emulsifying Drug Delivery Systems (SEDDS) of Nimodipine"; *AAPS Pharm. Sci. Tech.,* 9(1); (2008); pp. 191-196.
Kamel S., et al; "Pharmaceutical significance of cellulose: A review"; *eXPRESS Polymer Letters* vol. 2, No. 11; (2008); pp. 758-778.
Kane, Anil, et al; "A Statistical Mixture Design Approach for Formulating Poorly Soluble Compounds in Liquid Filled Hard Shell Capsules"; *Bulletin Technique Gattefosse* No. 99; (2006); pp. 43-49.
Karatas, A., et al; "Improved solubility and dissolution rate of piroxicam using gelucire 44/14 and labrasol"; *II Farmaco* 60(9); (2005); pp. 777-782; available online Aug. 9, 2005.
Katz NP, et al.; "Behavioral monitoring and urine toxicology testing in patients receiving long-term opioid therapy" *Anesth Analg.* 97(4); (2003); pp. 1097-1102.

Katz NP, et al; "Development and preliminary experience with an ease of extractability rating system for prescription opioids"; *Drug Development and Industrial Pharmacy.* 32(6); (2006); pp. 727-746.
Katz NP, et al; "Prescription monitoring of medical and non-medical Schedule II opioid abuse in Massachusetts: 1996-2005"; *Conference paper presented at the 69th College on Problems of Drug Dependence (CPDD),* Quebec, Canada; (2007); 1 page.
Katz NP, et al.; "Challenges in the development of prescription opioid abuse-deterrent formulations"; *Clin J Pain,;* 23(8); (2007); pp. 648-660.
King; "Tablets, Capsules, and Pills" Remington's Pharmaceutical Sciences, Ed. Arthur Osol, Chapter 89, (1980); pp. 1553-1584.
Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics* 54; (2002); pp. 311-318.
Kulkarni, et al., "Polyactic Acid for Surgical Implants," *Arch. Surg.* vol. 93; (1966); pp. 839-843.
Lacoste, D., et al.; "Reversible Inhibition of Testicular Androgen Secretion by 3-, 5- and 6- Month Controlled-Release Microsphere Formulations of the LH-RH Agonist [D-Trp.sup.6, des-Gly-NH.sub.2]LH-RH Ethylamide in the Dog"; *J. Seroid Biochem.* vol. 33, No. 5; (1989); pp. 1007-1011.
Laforet, Jean-Pierre, et al; "The Right Mix"; *Gattefosse,* vol. 7, No. 1; (1995); pp. 1-10.
Lalovic Bojan, et al; "Pharmacokinetics and pharmacodynamics of oral oxycodone in healthy human subjects: role of circulating active metabolites"; *Clin Pharmacol Ther* 79(5); (2006); pp. 461-479.
Larsen, A., et al; "In vitro evaluation of Pharmaceutical surfactants fate during lipolysis and its effects on solubilization of a poorly soluble model compound: Danazol"; *Conference on When Poor Solubility Becomes an Issue: From Early Stage to Proof of Principles;* (2006); Verona (Italy); 2 pages.
Larsen, Anne, et al; "Pharmaceutical Surfactants in Biorelevant Media: Impact on Lipolysis and Solubility of a Poorly Soluble Compound; Danazol"; *Conference, 5th World Meeting on Pharmaceutics Biopharmaceutics and Pharmaceutical Technology,* Geneva, Switzerland; (2006); 2 pages.
Lopez et a;. "Comparative efficacy of two once daily methylphenidate formulations (Ritalin LA and Concerta) and placebo in children with attention deficit hyperactivity disorder across the school day"; *Pediatr Drugs* 5(8); (2003); pp. 545-555.
Lowden, K.; "Filling hard gelatin capsules: experience in a new environment"; *Pharmaceutical Manufacturing Review,* vol. 10, No. 5; (1998); pp. 27-29.
Loy, R.G., et al; "The Effects of Human Chorionic Gonadotrophin on Ovulation, Length of Estrus, and Fertility in the Mare"; University of California, Davis, California, Jan. 30, 1965; pp. 41-50.
Malhotra Bimal K. et al; . "The pharmacokinetics of oxycodone and its metabolites following single oral doses of Remoxy®, an abuse-deterrent formulation of extended-release oxycodone, in patients with hepatic or renal impairment"; *Journal of Opioid Management* 11:2; Mar./Apr. 2015; pp. 157-169.
Markowitz et al; "Advances in the pharmacotherapy of attention-deficit-hyperactivity disorder: focus on methylphenidate formulations"; *Pharmacotherapy* 23(10); (2003); pp. 1281-1299.
Markowitz et al; "Pharmacokinetics of methylphenidate after oral administration of two modified-release formulations in healthy adults"; *Clin Pharmacokinet* 42(4); (2003); pp. 393-401.
Material Safety Data Sheet "Eastman: Cellulose Acetate Butyrate CAB-381-2 BP CAB381-20 BP: Coating Chemicals" Eastman Chemical Company, Publication E-296B, Aug. 1994.
Material Safety Data Sheet "Eastman: Cellulose Esters for Pharmaceutical Drug Delivery" Eastman Chemical Company, Publication PCI-105B, Jun. 2004.
Material Safety Data Sheet of Eastman Chemical Products, "SAIB" Sucrose Acetate Isobutyrate, pp. 1-24. Publication GN-311F (Jun. 2004).
Material Safety Data Sheet of Eastman Fine Chemical Pharmaceutical Ingredients, Sucrose Acetate Isobutyrate Special Grade (SAIB-SG), Publication No. EFC-211, (May 1991).

(56) References Cited

OTHER PUBLICATIONS

Material Safety Data Sheet of Eastman Products for the Food Industry, "Sucrose Acetate Isbutyrate (SAIB-SB) for Use in Fruit-Flavored Beverages," Publication No. ZM-90, (Sep. 1989); pp. 2-7.
McCabe SE, et al; "Motives, diversion and routes of administration associated with nonmedical use of prescription opioids"; *Addictive Behaviors.* 32; (2007); pp. 562-575.
McCarthy, P.F., et al.; "Management of Stallions on Large Breeding Farms"; *Veterinary Clinics of North America: Equine Practice,* vol. 8, No. 1; Apr. 1992; pp. 219-235.
McKinnon, A.O., et al.; "Effect of GnRH Analogue (Ovuplant), hCG and Dexamethasone on Time to Ovulation in Cycling Mares"; *World Equine Veterinary Review,* vol. 2: No. 3; (1997); pp. 16-18.
McKinnon, A.O., et al.; "Repeated Use of a GnRH Analogue Deslorelin (Ovuplant) for Hastening Ovulation in the Transitional Mare"; *Equine Veterinary Journal* 29 (2); (1996); pp. 153-155.
McLellan AT, et al; An improved diagnostic instrument for substance abuse patients—The Addiction Severity Index: *The Journal of Nervous and Mental Disease.* vol. 168, No. 1; (1980); pp. 26-33.
Mearns, D.; "Changing Seasons"; *The Blood-Horse;* Sep. 28, 1996; pp. 4794-4765.
Meehan, E., et al; "Monitoring the stability of excipients used in lipid matrix formulations"; (Poster Abstract), Conference "*33rd Annual Meeting of the Controlled Release Society*", Vienna, Austria. Jul. 22, 2006; 2 pages.
Mehuys, E., et al; "Human bioavailability of propranolol from a matrix-in-cylinder system with a HPMC-Gelucire® core"; *Journal of Controlled Release* 107; (2005); pp. 523-536; available online Aug. 1, 2005.
Merrifield, Bruce; "Solid Phase Synthesis"; *Science,* vol. 232; Apr. 18, 1986; pp. 341-347.
Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005; pp. 1-4.
Montovan, S.M., et al; "The Effect of a Potent GnRH Agonist on Gonadal and Sexual Activity in the Horse"; *Theriogenology,* vol. 33 No. 6; Jun. 1990; pp. 1305-1321.
Mumford, E.L.; "Use of Deslorelin Short-Term Implants to Induce Ovulation in Cycling Mares During Three Consecutive Estrous Cycles"; *Animal Reproduction Science,* vol. 39; (1995); pp. 129-140.
Murray Sally, et al; "Alcohol-associated rapid release of a long-acting opioid"; *CMAJ*;173(7); Sep. 27, 2005; pp. 756.
Nabors, et al; "Controlled Release of Diclofenac-Na from Cellulose Ester Microspheres"; *PDD Presentation 7481 at the 1994 Ninth Annual AAPS Meeting* in San Diego, CA; Nov. 6-10, 1994; 2 pages.
Nakagaki, Arita; "Seizai Butsuri Kagaku (Physical Chemistry of Medical Preparations)", pub. Asakura Shoten; Nov. 5, 1968; Tokyo; 6 pages.
Nally, J., et al.; "Induction of Mucosal IgA Specific for SeMF3 for *Streptococcus equi* with Intranasal Vaccination Using a Sucrose Acetate Isobutyrate Based Delivery System", *Proceed. Int'l. Symp. Control. Rel. Bioact. Mater.,* 26; (1999); Controlled Release Society, Inc. 2 pages.
"Natrosol® Hydroxyethylcellulose A Nonionic Water-Soluble Polymer"; Hercules Incorporated, Aqualon Division; (1999); pp. 1-24.
Nett, T.M., et al.; "Further Studies on the Radioimmunoassay of Gonadotropin-releasing Hormone: Effect of Radioiodination, Antiserum and Unextracted Serum on Levels of Immunoreactivity in Serum"; *Endocrinology* vol. 101, No. 4, (1977); pp. 1135-1144.
O'Driscoll, Caitriona M.; "Lipid-based formulations for intestinal lymphatic delivery"; *European Journal of Pharmaceutical Sciences* 15; (2002); pp. 405-415.
Okumu, et al; "Evaluation of Saber™ as a Local Delivery System for rhVEGF-Formulation Design and In Vitro Assessment" Genentech, Inc., South San Francisco, CA USA and Southern BioSystems, Inc. Birmingham AL, USA; (2000); 1 page.
Okumu, et al; "Evaluation of Saber™ as a Local Delivery System for rhVEGF-Formulation Design and In Vitro Assessment" Genentech, Inc., South San Francisco, CA USA and Southern BioSystems, Inc. Birmingham AL, USA. Poster; (2001); 1 page.
Office Action for U.S. Appl. No. 14/776,585, dated Mar. 17, 2016.
Office Action for U.S. Appl. No. 14/214,057, dated Oct. 5, 2015.
Patel, Pranav, et al; "Preparation, Evaluation and Comparison of Lipid Based Drug Delivery Systems of Tacrolimus"; *International Journal of Pharmacy and Pharmaceutical Sciences,* vol. 6 Suppl 2; (2014); pp. 588-591.
Patrick et al; "New methylphenidate formulations for the treatment of attention-deficit/hyperactivity disorder" *Expert Opin Drug Deliv* 2(1); (2005); pp. 121-143.
Pelham et al; "Once-a-day Concerta methylphenidate versus three-times-daily methylphenidate in laboratory and natural settings"; *Pediatrics* vol. 107, No. 6; Jun. 6, 2001; pp. 1-15.
Perissutti, B.; et al; "Solid dispersions of carbamazepine with Gelucire 44/14 and 50/13"; *S.T.P. Pharma Sciences* 10(6); (2000); pp. 479-484.
Pozzi, Franco, et al; "Formulations of Ubidecarenone with Improved Bioavailability"; *Eur. J. Pharm. Biopharm,* vol. 37, No. 4; (1991); pp. 243-246.
Pulido et al.; "Enzymatic Regioselective Acylation of Hexoses and Pentoses Using Oxime Esters"; *J. Chem. Soc. Perkin Trans.* 1, (21); (1992); pp. 2891-2898.
Rabb et al.; "Effects of Active Immunication Against GnRH on LH, FSH and Prolactin Storage, Sectretion and Response to Their Secretagogues in Pony Geldings"; *J. Anim. Sci.,* 68; (1990); pp. 3322-3329.
Ren, Shan, et al; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.
Reynolds, R.C. et al.; "Sucrose acetate isobutyrate (SAIB): historical aspects of its use in beverages and a review of toxicity studies prior to 1988"; *Food Chem. Toxicol.* 36(2), (1998); pp. 81-93.
Reynolds, R.C.; "Metabolism and pharmacokinetics of sucrose acetate isobutyrate (SAIB) and sucrose octaisobutyrate (SOIB) in rats, dogs, monkeys or humans: a review"; *Food Chem. Toxicol.,* 36 (2); (1998); pp. 95-99.
Robinson; "Coating of Pharmaceutical Dosage Forms" *Remington's Pharmaceutical Sciences,* Ed. Arthur Osol, Chapter 90; (1980); pp. 1585-1593.
Roser, J.J., et al.; "The Development of Antibodies to Human Chorionic Gonadotrpins Following its Repeated Injection in the Cyclic Mare";*J. Reprod. Fert Suppl.,* (1979); pp. 173-179.
Roussin, P. et al; Gelucire® 44/14; "A High-Performance System to Enhance Bioavailability of Poorly Water Soluble Drugs"; *Bulletin Technique Gattefosse,* No. 90; (1997); pp. 51-58.
Sachs-Barrable, K., et al; "Lipid Excipients Peceol and Gelucire 44/14 decrease P-glycoprotein mediated efflux of Rhodamine 123 partially due to modifying P-glycoprotein expression within Caco-2 Cells."; *J. Pharm. Pharm. Sci.,* 10(3); (2007); pp. 319-331.
Saeio, Kiattisak, et al; "Factors Influencing Drug Dissolution Characteristic From Hydrophilic Polymer Matrix Tablet"; *Scientia Pharmaceutica (Sci. Pharm.)* 75; (2007); pp. 147-163.
Saeki; "Progress of Orally Opiate Analgesics and Non-Steroidal Anti-Flammatory Agent" *Drug Deliv Syst* 20(5); (2005) pp. 521-529.
Santus et al.; "Osmotic Drug Delivery: A Review of the Patent Liter" *J Control Release* 35(1); (1995); pp. 1-21.
Schamp, Karen, et al; "Development of an in vitro/in vivo correlation for lipid formulations of EMD 50733, a poorly soluble, lipophilic drug substance"; *European Journal of Pharmaceutics and Biopharmaceutics* 62; (2006); pp. 227-234; available online Oct. 24, 2005.
Selimovic, Seila, and Hu Yue; "Aging Effects in Suspensions of Silica Particles"; *Mat. Res. Soc. Symp. Proc.,* vol. 790 Materials Research Society; (2004) pp. P7.11.1-P7.11.6.
Serajuddin, Abu T.M., et al; "Effect of Vehicle Amphiphilicity on the Dissolution and Bioavailability of a Poorly Water-Soluble Drug from Solid Dispersions"; *Journal of Pharmaceutical Sciences,* vol. 77, No. 5, May 1988; pp. 414-417.

(56) References Cited

OTHER PUBLICATIONS

Serajuddin, Abu T.M., et al; "Water Migration from Soft Gelatin Capsule Shell to Fill Material and Its Effect on Drug Solubility"; *Journal of Pharmaceutical Sciences*, vol. 75, No. 1; Jan. 1986; pp. 62-64.
Sethia, Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences*, vol. 91, No. 9; Sep. 2002; pp. 1948-1957.
Sethia, Sundeep, et al; "In Vitro-In Vivo Evaluation of Supercritical Processed Solid Dispersions: Permeability and Viability Assessment in Caco-2 Cells"; *Journal of Pharmaceutical Sciences*, vol. 93, No. 12; Dec. 2004; pp. 2985-2993; published online Oct. 1, 2004.
Setnik B, Roland CL, Cleveland JM, Webster L.; "The abuse potential of Remoxy((R)), an extended-release formulation of oxycodone, compared with immediate- and extended-release oxycodone"; *Pain Med.* 12(4); (2011); pp. 618-631.
Shah, N. H; et al; "Self-Emulsifying Drug Delivery Systems (SEDDS) for Improving In Vitro Dissolution and Oral Absorption of Lipophilic Drugs"; *Bulletin Technique. Gattefossé Report*, No. 85; (1992/93); pp. 45-54.
Sheen, Pai-Chang, et al; "Bioavailability of a Poorly Water-Soluble Drug from Tablet and Solid Dispersion in Humans"; *Journal of Pharmaceutical Sciences*, vol. 80, No. 7; Jul. 1991; pp. 712-714.
Shimpi, Shyam, et al; "Preparation and Evaluation of Diltiazem Hydrochloride—Gelucire 43/01 Floating Granules Prepared by Melt Granulation"; *AAPS PharmSciTech* 5(3), Article 43, (http://www.aapspharmscitech.org); (2004); pp. 1-6; published online Jul. 12, 2004.
Smith, Dawn A., et al; "A Novel Parental Delivery System" *AAPS Presentation PDD* 7270, Seattle, WA; (1996) Annual Meeting; 2 pages.
Soliman, M. S., et al; "Preparation and in vitro characterization of a semi-solid dispersion of flurbiprofen with Gelucire 44/14 and Labrasol"; *Pharmazie* 60(4); (2005); pp. 288-293.
Srinivas et al.; "Enantioselective pharmacokinetics and pharmacodynamics of dl-threo-methylphenidate in children with attention deficit hyperactivity disorder"; *Clin Pharmacal Ther* 52(5); (1992); pp. 561-568.
Stegemann. S., et al; "When Poor Solubility Becomes an Issue: From Early Stage to Proof of Concept"; *European Journal of Pharmaceutical Sciences* 31; (2007); pp. 249-261.
Strickley, Robert G; "An Overview of Lipid Excipients Currently Available: Strengths, Weaknesses and Opportunity Gaps: The Options for the Formulator"; *Bulletin Technique Gattefosse*, No. 100; (2007); pp. 31-37.
Strickley, Robert G.; "Solubilizing Excipients in Oral and Injectable Formulations"; *Pharmaceutical Research*, vol. 21, No. 2; Feb. 2004; pp. 201-230.
Subramanian, Ramaswamy, et al; "Effect of Lipid Excipients on In Vitro Pancreatic Lipase Activity"; *Drug Development and Industrial Pharmacy*, vol. 29, No. 8; (2003); pp. 885-890.
Sucrose Acetate Isobutyrate, 21 CFR 172.831 (1999).
Sullivan, et al; "Delivery of Taxol® and other Antineoplastic Agents from a Novel System Based on Sucrose Acetate Isobutyrate" *AAPS* Boston, MA. Southern BioSystems, Inc. Birmingham AL, USA (1997); 2 pages.
Sullivan, et al; "Sustained Release of Orally Administered Active Using Saber Delivery System Incorporated into Soft Gelatin Capsules"; *Proceed Int'l. Control. Rei. Bioact. Mater. Controlled Release Society.* vol. 25; Jun. 1998 Las Vegas NV; pp. 918-919.
Sullivan, et al; "Sustained Release of Progesterone and Estradiol from the Saber™ Delivery System: In Vitro and In Vivo Release Rates" *CRS* Las Vegas, NV. Southern BioSystems, Inc. Birmingham AL, USA; (1998); 2 pages.
Sullivan, et al; "Sustained Release of Lysozyme from the Saber™ Delivery System" *AAPS*, New Orleans, LA. Southern BioSystems, Inc. Birmingham AL, USA; (1999); 2 pages.

Sullivan, et al. (1998) "Sustained Release of Bupivacaine from the Saber™ Delivery System" *AAPS*, San Francisco, CA. Southern BioSystems, Inc. Birmingham AL, USA.
Sullivan, et al; "Incorporation of Polymer Microparticles Into Sucrose Acetate Isobutyrate Reduces Burst and Extends Release" *Proceed Int'l Symp. Control. Rel. Bioact. Mater.*, 27, Controlled Release Society, Inc. Paris, France; Jul. 7-13, 2000.
Sullivan, J. J., et al.; "Duration of Estrus and Ovulation Time in Nonlactating Mares Given Human Chorionic Gonadotropin During Three Successive Estrous Periods"; *J.A.V.M.A.*, vol. 162, No. X; May 15, 1973; pp. 895-898.
Svensson, A., et al; "Hydration of an amphiphilic excipient Gelucire® 44/14"; *Int. J. Pharm.* 281(1-2); (2004); pp. 107-118.
Swanson et al; "Objective and subjective measures of the pharmacodynamic effects of Adderall in the treatment of children with ADHD in a controlled laboratory classroom setting"; *Psychopharmacol Bull* 34(1); (1998); pp. 55-60.
Swanson et al; "Acute tolerance to methylphenidate in the treatment of attention deficit hyperactivity disorder in children" *Clin Pharmacal Ther* 66(3); (1999); pp. 295-305.
Swanson et al. Ritalin: Theory and Practice. 2nd Edition, Greenhill & Osman Ed., Mary Ann Liebert, Larchmont, NY; (1999) pp. 405-430.
Swanson et al; "Efficacy of a new pattern of delivery of methylphenidate for the treatment of ADHD: effects on activity level in the classroom and on the playground" *J Am Acad Child Adolesc Psychiatry* 41(11); (2002); pp. 1306-1314.
Swanson et al; "Pharmacokinetic and pharmacodynamic properties of stimulants: implications for the design of new treatments for ADHD"; *Behav Brain Res* 130(1-2); (2002); pp. 73-78.
Swanson et al; "Development of a new once-a-day formulation of methylphenidate for the treatment of attention-deficit/hyperactivity disorder: proof-of-concept and proof-of-product studies"; *Arch Gen Psychiatry* 60(2); (2003); pp. 204-211.
Swanson et al; "Serum and brain concentrations of methylphenidate: implications for use and abuse"; *Neurosci Biobehav Rev* 27(7); (2003); pp. 615-621.
Swanson et al; "A comparison of once-daily extended-release methylphenidate formulations in children with attention-deficit/hyperactivity disorder in the laboratory school (the Comacs Study)"; *Pediatrics* 113(3 Pt. 1); (2004); pp. e206-e216.
Swiderski et al.; "Application of 14C Isotope in Studies on the Lability of Sugar Substituents" *Nukleonika, Supl.*, vol. 10; (1966); pp. 347-352.
Tashtoush, Bassam M., et al; "In Vitro and In Vivo Evaluation of Glibenclamide in Solid Dispersion Systems"; *Drug Development and Industrial Pharmacy*, vol. 30, No. 6; (2004); pp. 601-607.
Thompson, D. L., et al., "Effects of Melatonin and Thyrotropin Releasing Hormone on Mares During the Nonbreeding Season", Journal of Animal Science, vol. 56, No. 3, (1983), pp. 668-677.
Thompson, D. L., et al., "Testosterone Effects on Mares During Synchronization with Altrenogest: FHS, LH, Estrous Duration and Pregnancy Rate"; *Journal of Animal Science*, vol 56, No. 3; (1983); pp. 678-686.
Tipton; "Peptide Delivery from an In Situ Gelling System Based 1on Sucrose Acetate Isobutyrate" *AAPS J Abstract.* Southern BioSystems, Inc. Birmingham AL, USA; (1999); 1 page.
Tipton, "In Situ Gelling Systems"; Sustained-Release Injectable Products, Ed. Senior & Radomsky, Interpharm Press, Denver, CO; (2000); pp. 258-259.
Tipton, et al; "Local Delivery from a Novel Biodegradable in Situ Delivery System"; *Sixth World Biomaterials Congress*, Kamuela, HI,. Southern BioSystems, Inc. Birmingham AL, USA, May 15-20, 2000; 1 page.
Tran, Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics* 72; (2009); pp. 83-90; available online Dec. 25, 2008.
Trescot AM, et al; "Opioid Guidelines in the Management of Chronic Non-Cancer Pain." *Pain Physician*, vol. 9; (2006), pp. 1-40.

(56) References Cited

OTHER PUBLICATIONS

U.S. Department of Health and Human Services "Guidance for Industry: Food-Effect Bioavailability and Fed Bioequivalence Studies" FDA, Center for Drug Evaluation and Research (CDER), Dec. 2002.
U.S. Appl. No. 12/754,486, filed Apr. 5, 2010, 103 pages; with Preliminary Amendment filed Nov. 23, 2010, 13 pages.
U.S. Appl. No. 60/434,839, filed Dec. 18, 2002, 111 pages.
Vega-Rios Aracelly, et al; "Acid-catalyzed hydrolysis of triacylglycerols obeys monoexponential kinetics."; *International Journal of Chemical Kinetics,* vol. 24; (1992); pp. 887-894.
Venkatesan, N. et al; "Gelucire® 44/14 and Labrasol® in Enhancing Oral Absorption of Poorly Absorbable Drugs"; *Bulletin Technique Gattefosse,* No. 99; (2006); pp. 79-88.
Vila Jato, J.L., et al; "Influence of melting point and HLB on the release of amoxicillin from granulates containing Gelucire as excipients"; *S.T.P. Pharma,* vol. 6, No. 5; (1990); pp. 287-292.
Voss, J.L., et al; "The Effect of HCG on Duration of Oestrus, Ovulation Time and Fertility in Mares"; *Journal of Reprod. Fert., Suppl.* 23; (1975); pp. 297-301.
Volkow et al; "Relationship between psychostimulant-induced "high" and dopamine transporter occupancy"; *Proc Natl Acad Sci USA* 93(19); (1996); pp. 10388-10392.
Volkow et al. "Temporal relationships between the pharmacokinetics of methylphenidate in the human brain and its behavioral and cardiovascular effects"; *Psychopharmacology* 123; (1996) pp. 26-33.
Volkow et al; "Methylphenidate and cocaine have a similar in vivo potency to block dopamine transporters in the human brain"; *Life Sciences* vol. 65, No. 1; (1999); PL7-PL12.
Volkow et al; "Relationship between blockade of dopamine transporters by oral methylphenidate and the increases in extracellular dopamine: therapeutic implications"; *Synapse* 43(3); (2002); pp. 181-187.
Volkow, et al; "Dopamine transporter occupancies in the human brain induced by therapeutic doses of oral methylphenidate"; *Am J Psychiatry* 155(10); (1998); pp. 1325-1331.
Webster LR.; "PTI-821: sustained-release oxycodone using gel-cap technology"; *Expert Opin Investig Drugs.* 16(3); (2007); pp. 359-366.
Wigal et al; "Reliability and validity of the SKAMP rating scale in a laboratory school setting" *Psychopharmacol Bulletin,* vol. 34, No. 1; (1998); pp. 47-53.
Wigal et al; "Selection of the Optimal Dose Ratio for a Controlled-Delivery Formulation of Methylphenidate"; *The Journal of Applied Research* 3; (2003); pp. 46-63.
Wightman et al; "Transient changes in mesolimbic dopamine and their association with 'reward'"; *Journal of Neurochemistry* 82(4); (2002); pp. 721-735.
Wolraich et al; "Randomized, controlled trial of oros methylphenidate once a day in children with attention-deficit/hyperactivity disorder"; *Pediatrics* 108(4); (2001); pp. 883-892.
Yüksel, Nilüfer, et al; "Enhanced bioavailability of piroxicam using Gelucire 44/14 and Labrasol: in vitro and in vivo evaluation"; *European Journal of Pharmaceutics and Biopharmaceutics* 56; (2003); pp. 453-459.
Webster LR. PTI-821: sustained-release oxycodone using gel-cap technology. Expert Opin Investig Drugs. 2007; 16(3):359-366.
Zamloot M, et al.; "Remoxy®: a novel formulation of extended-release oxycodone developed using the Oradur® technology"; *J Appl Res.* 10(3) (2010); pp. 88-96.
U.S. Appl. No. 15/342,956, filed Nov. 3, 2016, Yum et al.
U.S. Appl. No. 15/102,519, filed Jun. 7, 2016, Sekar et al.
U.S. Appl. No. 15/398,426, filed Jan. 4, 2017, Yum et al.
U.S. Appl. No. 15/435,142, filed Feb. 16, 2017, Scicinski et al.
U.S. Appl. No. 15/486,119, filed Apr. 12, 2017, Yum, et al.

Panel A

Panel B

Process Flow Chart for Oxycodone Compounded Mass

Process Flow Chart for Encapsulation

Panel A (Reference A ~ 15% IPM)

Panel B (Formulation 10 ~ 8% IPM)

Panel C (Formulation 11, 0% IPM)

Panel A (Reference A ~ 2% SiO$_2$)

Panel B (Formulation 12 ~ 1% SiO$_2$)

Panel C (Formulation 13, 0% SiO$_2$)

Panel A

Panel B

Panel A

Panel B

Panel C

Panel A

Panel B

Panel C

Panel A

Panel B

Panel C

Panel A

Panel B

Panel C

Panel A

Panel B

Panel C

Panel A

Panel B

Panel C

Panel A

Panel B

Panel C

Panel A

Panel B

Panel C

Sample Variation for 5 mg Oxycodone Formulations with Increasing SiO$_2$

Panel A

Panel B

Panel C

Panel D

Panel E

Sample Variation for 40 mg Oxycodone Formulations with Increasing SiO$_2$

Panel A

Panel B

Panel C

Panel D

Panel E

Panel A

Panel B

Panel A

Panel B

COMPOSITIONS WITH A RHEOLOGICAL MODIFIER TO REDUCE DISSOLUTION VARIABILITY

CROSS-REFERENCE TO RELATED APPLICATIONS

This application is a continuation of U.S. patent application Ser. No. 14/214,057, filed Mar. 14, 2014, now U.S. Pat. No. 9,555,113, which application claims the benefit of and expressly incorporates by reference herein the entire disclosure of U.S. Provisional Patent Application No. 61/801,110, filed Mar. 15, 2013.

INTRODUCTION

Extended release pharmaceutical compositions, including extended release oxycodone compositions, may include various pharmaceutically inactive components which contribute to the desired pharmacokinetic parameters of the active agent in the composition. Such compositions may also include pharmaceutically inactive components which contribute to one or more abuse-deterrent characteristics of the composition. In some such cases, extended release pharmaceutical compositions may be provided which are viscoelastic in nature with a combination of hydrophilic and hydrophobic components. In addition to solubility of the active agent in the composition, the release of the active agent may be controlled, at least in part, by balancing the viscoelastic and hydrophilic nature of the composition. However, in some cases, the viscoelastic and/or hydrophilic nature of the composition may also contribute to undesirable sample variability during dissolution of the active agent from the composition. This undesirable sample variability may be evidenced by inter-capsule variability at a particular time point and/or as a storage-time dependent change in mean release of the active agent from the composition. The present disclosure addresses these issues and provides related advantages.

SUMMARY

The present disclosure provides compositions (e.g., extended release compositions) which exhibit a desirable pharmacokinetic profile of an active agent while providing reduced dissolution sample variability, e.g., in the form of reduced inter-capsule variability and/or a reduction in storage-time dependent change in mean release of the active agent from the composition. Related methods of making and administering the disclosed compositions are also provided.

DEFINITIONS

Figure 1A:
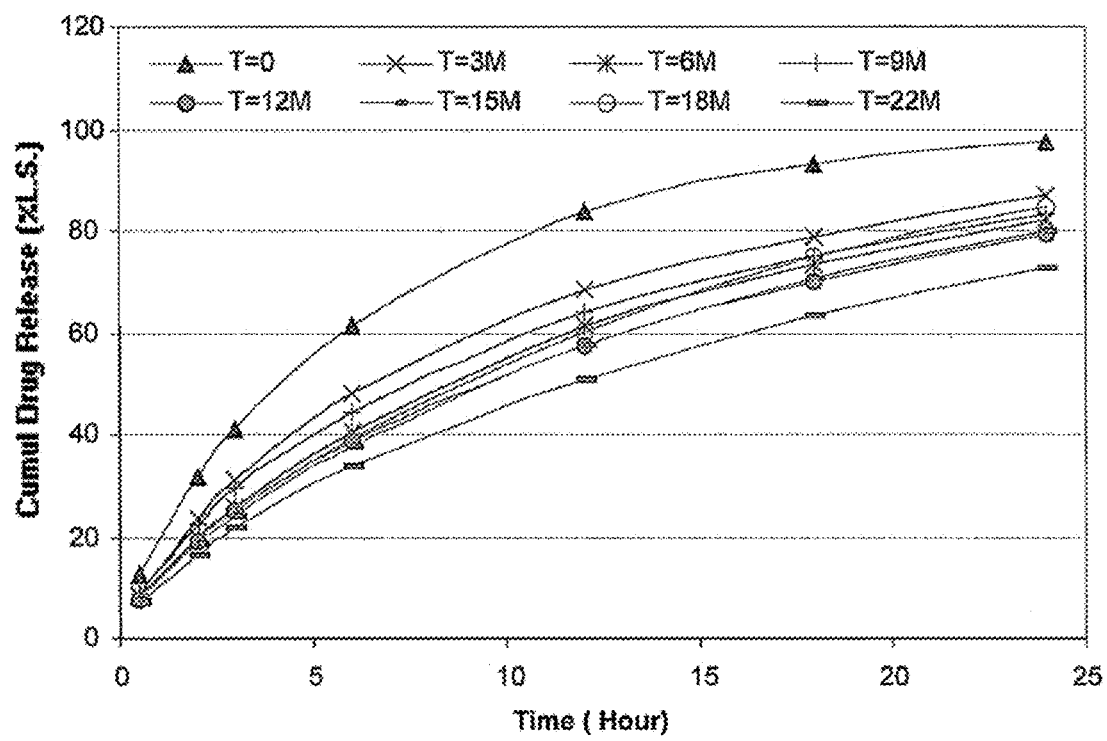
FIG. 1A is a graph showing a storage-time dependent change in the release of oxycodone from a reference composition (Reference Formulation A (with BHT)).

As used interchangeably herein, the terms "active agent", "pharmacologically active agent" and "beneficial agent" refer to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology.

As used herein, the term "high viscosity liquid carrier material (HVLCM)" refers to a non-polymeric, non-water soluble liquid material having a viscosity of at least 5000 cP at 37° C. that does not crystallize neat at 25° C. and 1 atmosphere.

As used herein, the term "rheology modifier" refers to a substance that possesses both a hydrophobic and a hydrophilic moiety. Rheology modifiers suitable for use in the disclosed compositions and methods generally have a logarithm of octanol-water partition coefficient ("Log P") of between about −7 and +15, e.g., between −5 and +10, e.g., between −1 and +7.

As used herein, the term "network former" refers to a material or compound that forms a network structure when introduced into a liquid medium (such as a HVLCM).

As used herein, the term "hydrophilic agent" means a compound or material having a natural affinity for aqueous systems. A material may be regarded as a hydrophilic agent for the purposes of this disclosure if the material displays a water sorption between about 10 to 100% (w/w). Hydrophilic agents will have a low Log P value.

As used herein, the term "hydrophilic solvent" means a solvent meeting the definition of a hydrophilic agent as described above.

The term "solvent", as used herein, refers to any substance that dissolves another substance (solute).

As used herein, the term "treatment", "treat" and "treating" pain refers to eliminating, reducing, suppressing or ameliorating, either temporarily or permanently, either partially or completely, a clinical symptom, manifestation or progression of pain. In addition, or alternatively, the terms "treatment", "treat" and "treating" as used herein with respect to the methods as described refer to inhibiting, delaying, suppressing, reducing, eliminating or ameliorating, either temporarily or permanently, either partially or completely, pain. In some embodiments the treating is effective to reduce a symptom, sign, and/or condition of pain in a subject by at least about 10% (e.g., 15%, 20%, 25%, 30%, 35%, 40%, 45%, 50%, 55%, 60%, 65%, 70%, 75%, 80%, 85%, 90%, 95%, or 100%) including, as compared to a baseline measurement of the symptom, sign, and/or condition made prior to the treatment. In some embodiments, the treating is effective to improve an assessment used to diagnose pain in a subject including, as compared to a baseline assessment made prior to the treatment. Such treating as provided herein need not be absolute to be useful.

The term "pharmaceutically acceptable salt," as used herein, intends those salts that retain the biological effectiveness and properties of neutral active agents and are not otherwise unacceptable for pharmaceutical use.

As used herein, the term "viscosity enhancing agent" refers to a compound or material that can be added to an extended release composition in order to increase the viscosity of the resulting composition.

As used herein, the term "stabilizer" refers to any substance used to inhibit or reduce degradation (e.g., chemical) of other substances with which the stabilizer is mixed.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a composition" includes a plurality of such compositions and reference to "the capsule" includes reference to one or more capsules and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

To the extent the definition or usage of any term herein conflicts with a definition or usage of a term in an application or reference incorporated by reference herein, the instant application shall control.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

The present disclosure provides compositions (e.g., extended release compositions) which exhibit a desirable pharmacokinetic profile of an active agent while providing reduced dissolution sample variability, e.g., in the form of reduced in vitro inter-capsule variability and/or a reduction in storage-time dependent change in mean in vitro release of the active agent from the composition. Related methods of making and administering the disclosed compositions are also provided. The compositions of the present disclosure generally include a pharmacologically active agent, a high viscosity liquid carrier material (HVLCM) and a solvent. In some embodiments, the compositions also include one or more of a rheology modifier, a network former, a hydrophilic agent, a viscosity enhancing agent and a stabilizing agent.
Pharmacologically Active Agent The pharmacologically active agents that may be included in the compositions of the present disclosure may include any type of biologically active compound or composition of matter which, when administered to an organism (human or animal subject) induces a desired pharmacologic and/or physiologic effect by local and/or systemic action.

Examples of such biologically active compounds or compositions of matter useful in the disclosed compositions include, but are not limited to, opioids, CNS depressants and stimulants.

Opioids are a class of potent narcotics that includes, for example, morphine, codeine, oxycodone and fentanyl and related drugs. Morphine is often used to alleviate severe pain. Codeine is used for milder pain. Other examples of opioids that can be prescribed to alleviate pain include oxycodone (e.g. OxyContin®—an oral, controlled release form of the drug); propoxyphene (e.g. Darvon™); hydrocodone (e.g. Vicodin™); hydromorphone (e.g. Dilaudid™); and meperidine (e.g. Demerol™).

In addition to relieving pain, opioids can also produce a sensation of euphoria, and when taken in large doses, can cause severe respiratory depression which can be fatal.

CNS depressants slow down normal brain function by increasing GABA activity, thereby producing a drowsy or calming effect. In higher doses, some CNS depressants can become general anesthetics, and in very high doses may cause respiratory failure and death. CNS depressants are frequently abused, and often the abuse of CNS depressants occurs in conjunction with the abuse of another substance or drug, such as alcohol or cocaine. Many deaths occur yearly through such drug abuse. CNS depressants can be divided into two groups, based on their chemistry and pharmacology: (1) Barbiturates, such as mephobarbital (e.g. Mebaral™) and pentobarbital sodium (e.g. Nembutal™) which are used to treat anxiety, tension, and sleep disorders. (2) Benzodiazepines, such as diazepam (e.g. Valium™), chlordiazepoxide HCl (e.g. Librium™), and alprazolam (e.g. Xanax™), which can be prescribed to treat anxiety, acute stress reactions, and panic attacks. Benzodiazepines that have a more sedating effect, such as triazolam (e.g. Halcion™) and estazolam (e.g. ProSom™) can be prescribed for short-term treatment of sleep disorders.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma. Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system. In addition, the increase in dopamine is associated with a sense of euphoria that can accompany the use of these drugs.

Taking high doses of a stimulant can result in an irregular heartbeat, dangerously high body temperatures, and/or the potential for cardiovascular failure or lethal seizures. Taking high doses of some stimulants repeatedly over a short period of time can lead to hostility or feelings of paranoia in some individuals.

One class of biologically active compounds that may be included in the compositions of the present disclosure is the opioids class, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dextromethorphan, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, levomethorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), tapentadol, beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69,593, spiradoline, DPDPE, [D-Ala2,Glu4] deltorphin, DSLET, Met-enkephalin, Leu-enkephalin, β-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

In some embodiments, opioids for use in the compositions of the present disclosure are selected from morphine, hydrocodone, oxycodone, codeine, fentanyl (and its relatives), hydromorphone, meperidine, methadone, oxymorphone, propoxyphene or tramadol, or mixtures thereof. In some embodiments, opioids for use in the compositions of the present disclosure are selected from oxycodone, oxymorphone, hydrocodone and hydromorphone. In some embodiments, the opioids for use in the compositions of the present disclosure may be micronized. With respect to the opioid oxycodone, it may be beneficial to provide compositions that have a reduced level of peroxide degradation products such as alpha beta unsaturated ketones (ABUK). In such cases, the compositions of the present disclosure can be subjected to peroxide contaminant reduction and/or removal techniques in accordance with known methods.

Other pharmacologically active compounds or compositions of matter useful in the disclosed compositions include prochlorperazine edisylate, ferrous sulfate, aminocaproic acid, potassium chloride, mecamylamine, procainamide, amphetamine (all forms including dexamphetamine, dextroamphetamine, d-S-amphetamine, and levoamphetamine), benzphetamine, isoproternol, methamphetamine, dexmethamphetamine, phenmetrazine, bethanechol, metacholine, pilocarpine, atropine, methascopolamine, isopropamide, tridihexethyl, phenformin, methylphenidate (all forms including dexmethylphenidate, d-threo methylphenidate, and dl-threo methylphenidate), oxprenolol, metroprolol, cimetidine, diphenidol, meclizine, prochlorperazine, phenoxybenzamine, thiethylperazine, anisindone, diphenadione erythrityl, digoxin, isofurophate, reserpine, acetazolamide, methazolamide, bendroflumethiazide, chlorpropamide, tolazamide, chlormadinone, phenaglycodol, allopurinol, aluminum aspirin, methotrexate, acetyl sulfisoxazole, erythromycin, progestins, estrogenic progrestational, corticosteroids, hydrocortisone, hydrocorticosterone acetate, cortisone acetate, triamcinolone, methyltesterone, 17 beta.-estradiol, ethinyl estradiol, ethinyl estradiol 3-methyl ether, prednisolone, 17-hydroxyprogesterone acetate, 19-nor-progesterone, norgestrel, orethindone, norethiderone, progesterone, norgestrone, norethynodrel, aspirin, indomethacin, naproxen, fenoprofen, sulindac, diclofenac, indoprofen, nitroglycerin, propranolol, metroprolol, sodium valproate, valproic acid, taxanes such as paclitaxel, camptothecins such as 9-aminocamptothecin, oxprenolol, timolol, atenolol, alprenolol, cimetidine, clonidine, imipramine, levodopa, chloropromazine, resperine, methyldopa, dihydroxyphenylalanine, pivaloyloxyethyl ester of .alpha.-methyldopa hydrochloride, theophylline, calcium gluconate ferrous lactate, ketoprofen, ibuprofen, cephalexin, haloperidol, zomepirac, vincamine, diazepam, phenoxybenzamine, .beta.-blocking agents, calcium-channel blocking drugs such as nifedipine, diltiazen, verapamil, lisinopril, captopril, ramipril, fosimopril, benazepril, libenzapril, cilazapril cilazaprilat, perindopril, zofenopril, enalapril, indalapril, qumapril, and the like.

The active agent can be present in the compositions of the present disclosure in a neutral form, as a free base form, or in the form of a pharmaceutically acceptable salt. Pharmaceutically acceptable salts include salts of acidic or basic groups, which groups may be present in the active agents. Those active agents that are basic in nature are capable of forming a wide variety of salts with various inorganic and organic acids. Pharmaceutically acceptable acid addition salts of basic active agents suitable for use herein are those that form acid addition salts, i.e., salts including pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Active agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) *J. Pharm. Sci.* 66:1-19, the disclosure of which is incorporated by reference herein.

In the compositions of the present disclosure, the pharmacologically active agent will be dissolved (fully or partially) in one or more components of the composition or dispersed within one or more components of the composition. The phrase "dissolved or dispersed" is intended to encompass all means of establishing a presence of the active agent in the subject compositions and includes dissolution, dispersion, partial dissolution and dispersion, and/or suspension and the like. In addition, in certain embodiments of the present disclosure wherein the active agent is in a solid particulate form suspended within one or more other components of the composition, the active agent particulate may be pre-treated with a micronization process such as those described in U.S. Application Publication No. 2009/

0215808, the disclosure of which is incorporated by reference herein, to provide a particle population having a substantially homogeneous particle size the bulk of which fall within the micron (μm) range.

The pharmacologically active agent, which can include one or more suitable active agent, may be present in the disclosed compositions in an amount of from about 50 to about 0.1 percent by weight relative to the total weight of the composition (wt %), e.g., in an amount of from about 40 to about 0.1 wt %, in an amount of from about 30 to about 0.1 wt %, in an amount of from about 20 to about 0.1 wt %, in an amount of from about 10 to about 0.1 wt %, in an amount of from about 9 to about 0.1 wt %, in an amount of from about 8 to about 0.1 wt %, in an amount of from about 7 to about 0.1 wt %, in an amount of from about 6 to about 0.1 wt %, in an amount of from about 5 to about 0.1 wt %, in an amount of from about 4 to about 0.1 wt %, in an amount of from about 3 to about 0.1 wt %, in an amount of from about 2 to about 0.1 wt %, or in an amount of from about 1 to about 0.1 wt %, depending upon the identity of the active agent, the desired dose required for the dosage form, and the intended use thereof. In some embodiments, the pharmacologically active agent may be present in the disclosed compositions in an amount from about 0.1 to about 5 w %, in an amount from about 5 to about 10 w %, in an amount from about 10 to about 20 w %, in an amount from about 20 to about 30 w %, in an amount from about 30 to about 40 w %, or in an amount from about 40 to about 50 w %, depending upon the identity of the active agent, the desired dose required for the dosage form, and the intended use thereof. In some embodiments, the active agent is present in the composition in an amount of about 1 to about 10 wt %, and can thus be loaded into a suitable dosage form to provide single dosages ranging from about 0.01 mg to 1000 mg, or from about 0.1 mg to 500 mg, or from about 2 mg to 250 mg, or from about 2 mg to 250 mg, or from about 2 mg to 150 mg, or from about 5 mg to 100 mg, or from about 5 mg to 80 mg. For some embodiments that include an opioid active agent, exemplary single dosages include, but are not limited to, 1, 2, 3, 5, 10, 15, 20, 30, 40, 60, 80 100, and 160 mg. In other embodiments that include a CNS depressant or CNS stimulant, exemplary single dosages include, but are not limited to, 5, 10, 15, 18, 20, 25, 27, 30, 36, 40, 50, 54, 60, 70, 80 and 100 mg. The precise amount of active agent desired can be determined by routine methods well known to pharmacological arts, and will depend on the type of agent, and the pharmacokinetics and pharmacodynamics of that agent.

High Viscosity Liquid Carrier Material (HVLCM)

An HVLCM is a non-polymeric, non-water soluble liquid material having a viscosity of at least 5000 cP at 37° C. that does not crystallize neat at 25° C. and 1 atmosphere. The term "non-water soluble" refers to a material that is soluble in water to a degree of less than one percent by weight at 25° C. and 1 atmosphere. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "non-polymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein. HVLCMs may be carbohydrate-based, and may include one or more cyclic carbohydrates chemically combined with one or more carboxylic acids. HVLCMs also include non-polymeric esters or mixed esters of one or more carboxylic acids, having a viscosity of at least 5,000 cP at 37° C., that do not crystallize neat at 25° C. and 1 atmosphere, wherein when the ester contains an alcohol moiety (e.g., glycerol). The ester may, for example include from about 2 to about 20 hydroxy acid moieties. Various HVLCMs, which may be used be included in disclosed compositions are described in U.S. Pat. Nos. 5,747,058; 5,968,542; and 6,413,536; the disclosures of each of which are incorporated by reference herein. The presently disclosed compositions may employ any HVLCM described in these patents but is not limited to any specifically described materials.

The HVLCM may be present in the composition at from about 35% by weight to about 45% by weight, based on total weight of the composition. For example, the HVLCM may be present in the composition at from about 36% by weight to about 45% by weight, from about 37% by weight to about 45% by weight, from about 38% by weight to about 45% by weight, from about 39% by weight to about 45% by weight, from about 40% by weight to about 45% by weight, from about 41% by weight to about 45% by weight, from about 42% by weight to about 45% by weight, from about 43% by weight to about 45% by weight, or from about 44% by weight to about 45% by weight relative to the total weight of the composition. In some embodiments, the HVLCM may be present in the composition at from about 35% by weight to about 37% by weight, from about 37% by weight to about 39% by weight, from about 39% by weight to about 41% by weight, from about 41% by weight to about 43% by weight, or from about 43% by weight to about 45% by weight relative to the total weight of the composition. In some embodiments, the HVLCM may be present in the composition at about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

In some embodiments, the amount of the HVLCM present in the composition is provided relative to the amount of the solvent present in the composition. For example, the HVLCM and the solvent may be provided in the composition at a ratio of about 1.3:1 to about 1:1, e.g., about 1.20:1 to about 1:1, about 1.15:1 to about 1:1, about 1.10:1 to about 1:1, or about 1:1. In some embodiments, the HVLCM and the solvent may be provided in the composition at a ratio of about 0.6:1 to about 1.6:1, e.g., about 0.8:1 to about 1.5:1, or about 0.9:1 to about 1.5:1.

In some embodiments, Sucrose Acetate Isobutyrate ("SAIB") may be included in the composition as the HVLCM. SAIB is a non-polymeric highly viscous liquid at temperatures ranging from −80° C. to over 100° C., it is a fully esterified sucrose derivative, at a nominal ratio of six isobutyrates to two acetates. The chemical structure of SAIB is provided in U.S. Application Publication No. 2009/0215808, the disclosure of which is incorporated by reference herein. The SAIB material is available from a variety of commercial sources including Eastman Chemical Company, where it is available as a mixed ester that does not crystallize but exists as a very highly viscous liquid. It is a hydrophobic, non-crystalline, low molecular weight molecule that is water insoluble and has a viscosity that varies with temperature. For example, pure SAIB exhibits a viscosity of approximately 2,000,000 centipoise (cP) at ambient temperature (RT) and approximately 600 cP at 80° C. The SAIB material has unique solution-viscosity relationship in that a SAIB solution established in a number of organic solvents has a significantly lower viscosity value than the pure SAIB material, and therefore the SAIB-organic solvent solutions render themselves capable of processing using conventional equipment such as mixers, liquid pumps and capsule production machines. SAIB also has applications in drug formulation and delivery, for example as described in U.S. Pat. Nos. 5,747,058; 5,968,542; 6,413,536; and 6,498,153, the disclosure of which are incorporated by reference herein.

In the compositions of the present disclosure, SAIB may be used as the HVLCM and may be present at from about 35% by weight to about 45% by weight, based on total weight of the composition. For example, the SAIB may be present in the composition at from about 36% by weight to about 45% by weight, from about 37% by weight to about 45% by weight, from about 38% by weight to about 45% by weight, from about 39% by weight to about 45% by weight, from about 40% by weight to about 45% by weight, from about 41% by weight to about 45% by weight, from about 42% by weight to about 45% by weight, from about 43% by weight to about 45% by weight, or from about 44% by weight to about 45% by weight relative to the total weight of the composition. In some embodiments, the SAIB may be present in the composition at from about 35% by weight to about 37% by weight, from about 37% by weight to about 39% by weight, from about 39% by weight to about 41% by weight, from about 41% by weight to about 43% by weight, or from about 43% by weight to about 45% by weight relative to the total weight of the composition. In some embodiments, the SAIB may be present in the composition at about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

In some embodiments, the amount of SAIB present in the composition is provided relative to the amount of the solvent present in the composition. For example, the SAIB and the solvent may be provided in the composition at a ratio of about 1.3:1 to about 1:1, e.g., about 1.20:1 to about 1:1, about 1.15:1 to about 1:1, about 1.10:1 to about 1:1, or about 1:1. In some embodiments, the HVLCM and the solvent may be provided in the composition at a ratio of about 0.6:1 to about 1.6:1, e.g., about 0.8:1 to about 1.5:1, or about 0.9:1 to about 1.5:1.

In some embodiments, it may be beneficial to provide a SAIB carrier material having a lower peroxide level to avoid peroxide-based degradation of various components of the composition and/or active agent. See, e.g., U.S. Patent Application Publication Number US 2007/0027105, "Peroxide Removal From Drug Delivery Vehicle", the disclosure of which is incorporated by reference herein.

Solvent

Solvents may be used in the compositions of the present disclosure to dissolve one or more of the following constituents: HVCLMs; active agents; network formers; rheology modifiers; viscosity enhancing agents; hydrophilic agents; and stabilizing agents. In some embodiments, the solvent can dissolve both the HVLCM and the network former. In some embodiments of the compositions of the present disclosure, a composition may include both a hydrophilic solvent and a hydrophobic solvent. Organic solvents suitable for use with the compositions of the present disclosure include, but are not limited to: substituted heterocyclic compounds such as N-methyl-2-pyrrolidone (NMP) and 2-pyrrolidone (2-pyrol); triacetin; esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as benzyl alcohol, ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ϵ-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof.

In some embodiments, the solvent is selected from triacetin, N-methyl-2-pyrrolidone, 2-pyrrolidone, dimethylsulfoxide, ethyl lactate, propylene carbonate, and glycofurol. In some embodiments, the solvent is triacetin which is a hydrophilic solvent. In some embodiments, the hydrophilic triacetin solvent can be combined with a hydrophobic solvent to provide a hydrophobic/hydrophilic solvent system within the composition.

The solvent, which can include one or more suitable solvent materials, can be present in the compositions at from about 31% by weight to about 45% by weight, based on total weight of the composition. For example, the solvent may be present in the composition at from about 32% by weight to about 45% by weight, at from about 33% by weight to about 45% by weight, at from about 34% by weight to about 45% by weight, at from about 35% by weight to about 45% by weight, at from about 36% by weight to about 45% by weight, at from about 37% by weight to about 45% by weight, at from about 38% by weight to about 45% by weight, at from about 39% by weight to about 45% by weight, at from about 40% by weight to about 45% by weight, at from about 41% by weight to about 45% by weight, at from about 42% by weight to about 45% by weight, at from about 43% by weight to about 45% by weight, or at from about 44% by weight to about 45% by weight relative to the total weight of the composition. In some embodiments, the solvent may be present in the composition at from about 31% by weight to about 33% by weight, at from about 33% by weight to about 35% by weight, at from about 35% by weight to about 37% by weight, at from about 37% by weight to about 39% by weight, at from about 39% by weight to about 41% by weight, at from about 41% by weight to about 43% by weight, or at from about 43% by weight to about 45% by weight relative to the total weight of the composition. In some embodiments, the solvent may be present in the composition at about 31% by weight, about 32% by weight, about 33% by weight, about 34% by weight about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

Rheology Modifier

Rheology refers to the property of deformation and/or flow of a liquid, and rheology modifiers are used to modify viscosity and flow of a liquid composition. Rheology modifiers, which may be used in the compositions of the present disclosure include, for example, caprylic/capric triglyceride (e.g., Miglyol 810), isopropyl myristate (IM or IPM), ethyl oleate, triethyl citrate, dimethyl phthalate, and benzyl benzoate.

In some embodiments, the rheology modifier is IPM. The rheology modifier, which can include one or more suitable rheology modifier materials, can be present in the compositions at from about 2 to about 10 percent by weight relative to the total weight of the composition (wt %), e.g., at from about 2 to about 8 wt %, at from about 2 to about 6 wt %, or at from about 2 to about 4 wt %. In some embodiments, the rheology modifier is preset in the compositions at from about 2 to about 4 wt %, at from about 4 to about 6 wt %, at from about 6 to about 8 wt %, or at from about 8 to about 10 wt %.

In some embodiments, the rheology modifier is present in the compositions of the present disclosure in an amount relative to the amount of solvent in the compositions. For example, in some embodiments the solvent and the rheology modifier are present in the compositions at a ratio of about 1:0.3 to about 1.0:0.05, e.g., about 1:0.2 to about 1:0.06, about 1:0.1 to about 1:0.07, or about 1:0.09 to about 1:0.08.

Network Former

Network formers may be added to a composition such that, upon exposure to an aqueous environment, they form a three dimensional network within the composition. While not intending to be bound by any particular theory, it is believed that the network former allows the formation of a micro-network within the composition upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the composition and the aqueous environment of the GI tract, as well as the formation of a three-dimensional micro-network of precipitated network former within the composition. The network former is selected so as to have good solubility in the selected solvent used in the compositions, for example a solubility of between about 0.1 and 20 wt %. Additionally, good network formers will typically have a Log P between about −1 to 7. Suitable network formers include, for example, cellulose acetate butyrate ("CAB"), carbohydrate polymers, organic acids of carbohydrate polymers and other polymers, hydrogels, cellulose acetate phthalate, ethyl cellulose, Pluronic, Eudragit, Carbomer, hydroxyl propyl methyl cellulose, other cellulose acetates such as cellulose triacetate, PMMA, as well as any other material capable of associating, aligning or congealing to form three-dimensional networks in an aqueous environment.

In some embodiments, the network former used in the compositions of the present disclosure is a CAB having a number average molecular weight ranging from 50,000 Daltons to 100,000 Daltons, e.g., from about 60,000 Daltons to 100,000 Daltons, from about 70,000 Daltons to 100,000 Daltons, from about 80,000 Daltons to 100,000 Daltons, or from about 90,000 Daltons to 100,000 Daltons. In some embodiments, the network former used in the compositions of the present disclosure is a CAB having a number average molecular weight ranging from about 60,000 Daltons to about 90,000 Daltons, or from about 70,000 Daltons to about 80,000 Daltons.

In some embodiments, the network former used in the compositions of the present disclosure is a CAB having at least one feature selected from a butyryl content ranging from about 17% to about 41%, an acetyl content ranging from about 13% to about 30%, and a hydroxyl content ranging from about 0.5% to about 1.7%.

In some embodiments, the network former used in the compositions of the present disclosure is cellulose acetate butyrate grade 381-20BP ("CAB 381-20BP" available from Eastman Chemicals). In some embodiments, the network former used in the compositions of the present disclosure is a CAB, wherein the CAB is a non-biodegradable polymer material that has the following chemical and physical characteristics: butyryl content of about 36 wt %, acetyl content of about 15.5 wt %, hydroxyl content of about 0.8%, a melting point of from about 185-196° C., a glass transition temperature of about 128° C., and a number average of from about 66,000 to 83,000, e.g., about 70,000. In some embodiments, if a CAB material is used in the composition, it may be subjected to an ethanol washing step (and subsequent drying step) prior to addition to the composition in order to remove potential contaminants there from.

The network former, which can include one or more suitable network former materials, can be present in the compositions at from about 0.1 to about 20 percent by weight relative to the total weight of the composition (wt %), e.g., at from about 1 to about 18 wt %, from about 2 to about 10 wt %, from about 4 to about 6 wt %, or at about 5 wt %.

Hydrophilic Agent

Materials that can be used as "hydrophilic agents" in the compositions of the present disclosure include those that have natural affinity for aqueous systems. A material may be regarded as a hydrophilic agent for the purposes of this disclosure if the material displays a water sorption between about 10 to 100% (w/w). Hydrophilic agents will have a low Log P value. As discussed herein above, there are a number of constituents which may be used to produce the compositions of the present disclosure that can be classed as a hydrophilic material (e.g., a hydrophilic solvent), or at least a material having a hydrophilic portion (e.g., a rheology modifier). Since the HVLCM material used in the compositions is hydrophobic, it may be useful to include other materials in the composition that are hydrophilic in order to provide a carrier system that is balanced to have both hydrophobic and hydrophilic characteristics. For example, it is believed that the inclusion of one or more hydrophilic agents in the compositions of the present disclosure may participate in the control of active agent diffusion from the compositions. Accordingly, suitable hydrophilic agents include, but are not limited to, sugars such as sorbitol, lactose, mannitol, fructose, sucrose and dextrose, salts such as sodium chloride and sodium carbonate, starches, hyaluronic acid, glycine, fibrin, collagen, polymers such as hydroxylpropylcellulose ("HPC"), carboxymethylcellulose, hydroxyethyl cellulose ("HEC"); polyethylene glycol and polyvinylpyrrolidone, and the like. In some embodiments, a controlled release carrier system is provided that includes HEC as a hydrophilic agent.

The hydrophilic agent, which can include one or more suitable hydrophilic agent material, can be present in the compositions at from about 0.1 to about 10 percent by weight relative to the total weight of the composition (wt %), e.g., from about 1 to about 8 wt %, from about 2 to about 7 wt %, from about 3 to about 6 wt %, or from about 4 to about 5 wt %.

Viscosity Enhancing Agent

Viscosity enhancing agents can be selected to have good hydrogen bonding capability, such as a bonding capability greater than or equal to one per molecule. In certain cases, the viscosity enhancing agent has very low to no significant solubility in the composition. If the agent is soluble, then, in some embodiments, the solubility is less than 50 wt %. For inorganic or mineral viscosity enhancing agents, it is preferable if the material has a specific surface area greater than or equal to about 100 $m^2/g$. Suitable viscosity enhancing agents include biodegradable and non-biodegradable polymer materials. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, hydroxyethyl cellulose, or combinations or mixtures of the above materials. Suitable non-biodegradable polymers include: polyacrylates, ethylene-vinyl acetate polymers, cellulose and cellulose derivatives, acyl substituted cellulose acetates and derivatives thereof including cellulose acetate butyrate (CAB), which is also used herein as a network former, non-erodible polyurethanes, polystyrenes, polyvinyl chloride, polyvinyl fluoride, polyvinyl (imidazole), chlorosulphonated polyolefins, polyethylene oxide, and polyethylene.

Other suitable viscosity enhancing materials include mineral particles such as clay compounds, including, talc, bentonite and kaolin; metal oxides including silicon dioxide, zinc oxide, magnesium oxide, titanium oxide, and calcium oxide; and fumed silica, reagent grade sand, precipitated silica, amorphous silica, colloidal silicon dioxide, fused silica, silica gel, and quartz. In some embodiments of the present disclosure, a colloidal silicon dioxide (Cab-O-Sil) is used in the compositions as a viscosity enhancing agent.

The viscosity enhancing agent, e.g., mineral particle, which can include one or more suitable viscosity enhancing materials, can be present in the compositions at from about 2.4 to about 6.0 percent by weight relative to the total weight of the composition (wt %), e.g., at from about 2.5 to about 6.0 wt %, at from about 2.6 to about 6.0 wt %, at from about 2.7 to about 6.0 wt %, at from about 2.8 to about 6.0 wt %, at from about 2.9 to about 6.0 wt %, at from about 3.0 to about 6.0 wt %, at from about 3.1 to about 6.0 wt %, at from about 3.2 to about 6.0 wt %, at from about 3.3 to about 6.0 wt %, at from about 3.4 to about 6.0 wt %, at from about 3.5 to about 6.0 wt %, at from about 3.6 to about 6.0 wt %, at from about 3.7 to about 6.0 wt %, at from about 3.8 to about 6.0 wt %, at from about 3.9 to about 6.0 wt %, at from about 4.0 to about 6.0 wt %, at from about 4.1 to about 6.0 wt %, at from about 4.2 to about 6.0 wt %, at from about 4.3 to about 6.0 wt %, at from about 4.4 to about 6.0 wt %, at from about 4.5 to about 6.0 wt %, at from about 4.6 to about 6.0 wt %, at from about 4.7 to about 6.0 wt %, at from about 4.8 to about 6.0 wt %, at from about 4.9 to about 6.0 wt %, at from about 5.0 to about 6.0 wt %, at from about 5.1 to about 6.0 wt %, at from about 5.2 to about 6.0 wt %, at from about 5.3 to about 6.0 wt %, at from about 5.4 to about 6.0 wt %, at from about 5.5 to about 6.0 wt %, at from about 5.6 to about 6.0 wt %, at from about 5.7 to about 6.0 wt %, at from about 5.8 to about 6.0 wt %, or at from about 5.9 to about 6.0 wt %.

In some embodiments, a composition according to the present disclosure includes a viscosity enhancing agent, e.g., mineral particle, at from about 2.4 to about 2.6 wt %, at from about 2.6 wt % to about 2.8 wt %, at from about 2.8 wt % to about 3.0 wt %, at from about 3.0 wt % to about 3.2 wt %, at from about 3.2 wt % to about 3.4 wt %, at from about 3.4 wt % to about 3.6 wt %, at from about 3.6 wt % to about 3.8 wt %, at from about 3.8 wt % to about 4.0 wt %, at from about 4.0 wt % to about 4.2 wt %, at from about 4.2 wt % to about 4.4 wt %, at from about 4.4 wt % to about 4.6 wt %, at from about 4.6 wt % to about 4.8 wt %, at from about 4.8 wt % to about 5.0 wt %, at from about 5.0 wt % to about 5.2 wt %, at from about 5.2 wt % to about 5.4 wt %, at from about 5.4 wt % to about 5.6 wt %, at from about 5.6 wt % to about 5.8 wt %, or at from about 5.8 wt % to about 6.0 wt %.

As discussed in the Examples below, providing a viscosity enhancing agent, e.g., a mineral particle such as silicon dioxide, in an amount outside of one or more of the ranges specified above may result in undesirable composition characteristics. For example, variability in a dissolution profile of the active agent from the composition, e.g., as evidenced by increased inter-capsule variability, may be seen at relatively low silicon dioxide levels. On the other hand, reduced processability may be seen at relatively high silicon dioxide levels due to an increase in the rigidity and/or viscosity of the composition. Accordingly, in some embodiments, the compositions of the present disclosure specifically exclude viscosity enhancing agents, e.g., mineral particles, in an amount outside of one or more of the ranges specified above.

In some embodiments an unexpected, beneficial balance between dissolution variability and processability may be achieved by including the viscosity enhancing agent, e.g., mineral particle such as silicon dioxide, at from about 2.4 to about 5.4 percent by weight relative to the total weight of the composition (wt %), e.g., at from about 2.4 to about 2.6 wt %, at from about 2.6 to about 2.8 wt %, at from about 2.8 to about 3.0 wt %, at from about 3.0 to about 3.2 wt %, at from about 3.2 to about 3.4 wt %, at from about 3.4 to about 3.6 wt %, at from about 3.6 to about 3.8 wt %, at from about 3.8 to about 4.0 wt %, at from about 4.0 to about 4.2 wt %, at from about 4.2 to about 4.4 wt %, at from about 4.4 to about 4.6 wt %, at from about 4.6 to about 4.8 wt %, at from about 4.8 to about 5.0 wt %, at from about 5.0 to about 5.2 wt %, or at from about 5.2 to about 5.4 wt %. Similarly, a beneficial balance between dissolution variability and processability may be achieved by including the viscosity enhancing agent, e.g., mineral particle such as silicon dioxide, at from about 2.6 to about 5.4 wt %, e.g., at from about 2.8 to about 5.4 wt %, at from about 3.0 to about 5.4 wt %, at from about 3.2 to about 5.4 wt %, at from about 3.4 to about 5.4 wt %, at from about 3.6 to about 5.4 wt %, at from about 3.8 to about 5.4 wt %, at from about 4.0 to about 5.4 wt %, at from about 4.2 to about 5.4 wt %, at from about 4.4 to about 5.4 wt %, at from about 4.6 to about 5.4 wt %, at from about 4.8 to about 5.4 wt %, at from about 5.0 to about 5.4 wt %, or at from about 5.2 to about 5.4 wt %.

As discussed above, a viscosity enhancing agent, e.g., mineral particle, such as silicon dioxide, when included at specific concentration ranges in the compositions of the present disclosure, may reduce dissolution variability of the composition, e.g., inter-capsule dissolution variability as determined using a USP Apparatus 2 dissolution tester and method as described below in the Examples. See also, USP-NF, Dissolution <711>. Rockville, Md.: US Pharmacopeial Convention; 2008, the disclosure of which is incorporated by reference herein.

Stabilizing Agent

Materials that can be used as stabilizing agents in the compositions of the present disclosure include any material or substance that can inhibit or reduce degradation (e.g., by chemical reactions) of other substances or substances in the composition with which the stabilizer is mixed. Exemplary stabilizers typically are antioxidants that prevent oxidative damage and degradation, e.g., sodium citrate, ascorbyl palmitate, vitamin A, and propyl gallate and/or reducing agents. Other examples include ascorbic acid, vitamin E, sodium bisulfite, butylhydroxyl toluene (BHT), BHA, acetylcysteine, monothioglycerol, phenyl-alpha-nathylamine, lecithin, and EDTA. These stabilizing materials, which can include one or more of such suitable materials, can be present in the compositions at from about 0.001 to about 2 percent by weight relative to the total weight of the composition (wt %), e.g., at from about 0.01 to about 0.1 wt %, or at from about 0.01 to about 0.02 wt %. In some embodiments, the compositions of the present disclosure specifically exclude a stabilizing agent, such as those listed above.

Surfactants

In some embodiments, a composition according to the present disclosure may include one or more surfactants. Materials that can be used as surfactants in the practice of the present disclosure include neutral and/or anionic/cationic excipients. Accordingly, suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof; ampiphilic surfactants (glycerides, etc.); Gelucires (saturated polyglycolized glyceride (e.g., Gattefosse brand); and like materials. Surfactants, which can include one or more suitable surfactant material, can be present in the compositions of the present disclosure at from about 0.01 to about 5 percent by weight relative to the total weight of the composition (wt %), e.g., at from about 0.1 to about 5 wt %, or at from about 0.1 to about 3 wt %.

Exemplary Compositions

With reference to the various components discussed above, exemplary compositions are now described.

In some embodiments a composition is provided which includes a pharmacologically active agent; about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere; about 31% by weight to about 45% by weight, based on total weight of the composition, of a solvent; about 2% by weight to about 10% by weight, based on total weight of the composition, of a rheology modifier; and a cellulose acetate butyrate.

In some embodiments, a composition is provided which includes a pharmacologically active agent; about 35% by weight to about 45% by weight, based on total weight of the composition, of sucrose acetate isobutyrate (SAM); about 31% by weight to about 45% by weight, based on total weight of the composition, of triacetin; about 2% by weight to about 10% by weight, based on total weight of the composition, of isopropyl myristate (IPM); and about 4% to about 6% of a cellulose acetate butyrate (CAB), based on total weight of the composition.

In some embodiments, a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; about 2% by weight to about 10% by weight, based on total weight of the composition, of a rheology modifier; and a cellulose acetate butyrate (CAB), wherein the HVLCM and the solvent are present in the composition at a ratio of about 1.3:1 to about 1:1.

In some embodiments, a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio of about 1.3:1.0:0.3 to about 1.0:1.0:0.05.

In some embodiments, compositions are provided which provide specific advantages relative to a reference composition, e.g., Reference Formulation A as described in Example 1 below. Accordingly, in some embodiments a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition.

In some embodiments, an increase in the reproducibility of release may refer to a reduction or decrease in a storage time-dependent change in an in vitro release profile of a composition. In such embodiments, the reproducibility of release for the composition may be determined relative to Reference Formulation A, which exhibits more than 10% mean drug release decline, a similarity factor ($f_2$) of less than 50, when stored at 40° C./75% RH for a one month period of time relative to its initial release profile.

"Similarity factor" ($f_2$) as used herein refers to a logarithmic reciprocal square root transformation of one plus the mean squared (the average sum of squares) differences of drug percent dissolved between the test and the reference products. In other words, the similarity factor ($f_2$) is a logarithmic transformation of the sum-squared error of differences between the test $T_t$ and reference products $R_t$ over all time points. It represents the closeness of two comparative compositions. Generally similarity factor in the range of 50-100 is acceptable according to the US FDA. $f_2$ may be calculated as follows: $f_2 = 50 \cdot \log\{[1+(1/n)\Sigma_{t=1}^{n}(R_t-T_t)^2]^{-0.5} \cdot 100\}$, where $R_t$ and $T_t$ are the cumulative percentage dissolved at each of the selected n time points of the reference and test product respectively.

In some embodiments, an increase in the reproducibility of release may refer to a reduction or decrease in inter-capsule variability at a particular time point. In such embodiments, a decrease in inter-capsule variability may be evidenced by a % RSD of less than about 15%, e.g., less than about 10%, or less than about 5% at the particular time point, e.g., t=2 hr or t=3 hr. % RSD may be calculated as follows: % RSD=((SD/mean)×100). In some embodiments, a decrease in inter-capsule variability may be evidenced by a % RSD of from about 15% to about 1%, e.g., from about 10% to about 1%, or from about 5% to about 1%.

Suitable in vitro dissolution test conditions for determining a time-dependent change in an in vitro release profile of a composition or inter-capsule variability of a composition, e.g., an oxycodone or hydrocodone containing composition are as follows: a USP Apparatus 2 dissolution tester modified to include a 20 mesh screen hanging basket to hold the test article is utilized with dissolution medium containing 1000 ml 0.1 N HCl with 0.5% (w/w) SDS. The dissolution medium is maintained at 37° C. with stirring with 100 rpm paddle speed over the course of a 24 hour dissolution test. Standard sampling time points of 0.5, 2, 3, 6, 12 and 24 hours are utilized. A 1 mL sample is taken at each time point and assayed using reverse-phase HPLC at 240 nm wavelength with a mobile phase including 0.35% (w/v) SDS/ 0.7% (w/v) acetic acid/44% (w/v) acetonitrile in water. Where the dissolution test is used to determining a time-dependent change in an in vitro release profile of a composition, the composition may be stored for a suitable period of time prior to testing, e.g., the composition may be stored at 25° C./60% relative humidity (RH) for from 1 to 6 months or at 40° C./75% RH for from 1 to 6 months. A suitable number of capsules per composition tested may be, e.g., 12 capsules.

For compositions including amphetamine, the following dissolution testing protocol may be utilized: 2-phase dissolution medium is utilized in a USP Apparatus 2. Capsules are placed in stainless steel (316SS) wire spiral capsule sinkers for dissolution testing. The dissolution parameters are as follows: Dissolution medium: 750 ml 0.1N HCl for the first 2 hours, with the addition of 200 ml 0.19M phosphate buffer to achieve a final pH of 6.0; Paddle speed: 50 rpm; Vessel temperature: 37° C. Sampling time points: 0.25, 0.5, 1, 1.5, 2, 3, 6, 9, 12 and 24 hours. Sampling volume: 1 mL. Suitable HPLC parameters are as follows: Mobile phase A: 5 mM 1-Decanesulfonic acid, sodium salt, 5 mM sodium phosphate monobasic, pH 2.5; Mobile phase B: 100% acetonitrile; Mobile phase: 67% Mobile phase A and 33% Mobile phase B; 210 nm wavelength. A suitable number of capsules per composition tested may be, e.g., 6 capsules.

For compositions including methylphenidate, the following dissolution testing protocol may be utilized: 2-phase dissolution medium is utilized in a USP Apparatus 2. Capsules are placed in stainless steel (316SS) wire spiral capsule sinkers for dissolution testing. The dissolution parameters are as follows: Dissolution medium: 750 ml 0.1N HCl for the first 2 hours, with the addition of 200 ml 0.19M phosphate buffer to achieve a final pH of 6.0; Paddle speed: 50 rpm; Vessel temperature: 37° C. Sampling time points: 0.25, 0.5, 1, 1.5, 2, 3, 6, 9, 12 and 24 hours. Sampling volume: 1 mL. Suitable HPLC parameters are as follows: Mobile phase A: 5 mM 1-Decanesulfonic acid, sodium salt, 5 mM sodium phosphate monobasic, pH 2.5; Mobile phase B: 100% acetonitrile; Mobile phase: 71% Mobile phase A and 29% Mobile phase B; 210 nm wavelength.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate, wherein the composition is encapsulated within a hydroxypropylmethylcellulose capsule, and wherein the composition within the capsule includes less than 5% water by weight, based on total weight of the composition within the capsule.

In some embodiments, a composition is provided which includes: a pharmacologically active agent; and means for reducing a storage time-dependent change in an in vitro release profile of a composition relative to Reference Formulation A.

In some embodiments, a composition is provided which includes: oxycodone at about 5% by weight relative to the total weight of the composition; and means for reducing a storage time-dependent change in an in vitro release profile of the composition Relative to Ref. Formulation A.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the mineral particle is present in the composition in an amount from about 2.4% by weight to about 5.4% by weight relative to the total weight of the composition.

In some embodiments, a composition is provided which includes: an opioid; sucrose acetate isobutyrate (SAIB); triacetin; isopropyl myristate (IPM); cellulose acetate butyrate (CAB); hydroxyethyl cellulose (HEC); and silicon dioxide, wherein the silicon dioxide is present in the composition in an amount from about 2.4% by weight to about 5.4% by weight relative to the total weight of the composition.

In some embodiments, a composition is provided which includes: oxycodone; about 35% by weight to about 45% sucrose acetate isobutyrate (SAIB) relative to the total weight of the composition; about 31% by weight to about 45% of triacetin relative to the total weight of the composition; about 2% by weight to about 10% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.4% by weight to about 5.4% by weight of silicon dioxide relative to the total weight of the composition.

In some embodiments, a composition is provided which includes: oxycodone; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition.

In some embodiments, a composition is provided which includes: about 5% by weight of oxycodone relative to the total weight of the composition; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition.

In some embodiments, a composition is provided which includes: oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide at about 2.9% by weight relative to the total weight of the composition.

In some embodiments, a composition is provided which includes: oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide at about 2.9% by weight relative to the total weight of the composition, wherein the composition is encapsulated in a hydroxypropylmethylcellulose (HPMC) capsule.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to reduce a storage time-dependent change in an in vitro release profile of a composition relative to Reference Formulation A.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to reduce inter-capsule variability in an in vitro release profile of the composition relative to Reference Formulation A, when assayed in a USP Apparatus 2 dissolution tester modified to have a 20-mesh basket for containing the composition.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce a storage time-dependent change in an in vitro release profile of the composition relative to Reference Formulation A.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce inter-capsule variability relative to Formulation A when assayed in a USP Apparatus 2 dissolution tester modified to have a 20-mesh basket for containing the composition.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

In some embodiments, a composition is provided which includes: a pharmacologically active agent; and combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to inter-capsule variability relative to Reference Formulation A when assayed in a USP Apparatus 2 dissolution tester modified to have a 20-mesh basket for containing the composition.

In some embodiments, a composition is provided which includes: a pharmacologically active agent; and combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

In some embodiments, a composition is provided which includes: a pharmacologically active agent; and combined amounts of a high viscosity liquid carrier material (HV-LCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to storage time relative to Reference Formulation A when assayed in a USP Apparatus 2 dissolution tester modified to have a 20-mesh basket for containing the composition.

Methods of Making, Encapsulating and Administering

Once constituents have been selected to produce a composition (e.g., an extended release composition) in accordance with the present disclosure, a liquid pharmaceutical composition can be prepared by simply mixing, for example a HVLCM, a rheology modifier, a network former, the active agent, a solvent and any additional additives. The compositions of the present disclosure are produced as liquid mixtures, and have a number of excipient ingredients that are in solution, suspension, or in partial solution within the final composition. Suitable methods for compounding or manufacturing the compositions make use of typical pharmaceutical/chemical mixing and handling apparatus and techniques. Since the liquid compositions of the present disclosure are formed from a number of highly viscous liquids and solids, they may have high final viscosities. Accordingly, the specific equipment and techniques employed in the manufacture of such compositions may be selected so as to accommodate such material demands. In particular, various excipients, such as network formers, may be added to the composition mixture in the solid or semi-solid state, and as such they may be screened or otherwise size-reduced prior to addition to a composition mixing apparatus. Other solid excipients may require melting prior to addition to the liquid mixture. The HVLCM materials are very high viscosity liquid materials, however they tend to exhibit a dramatic reduction in viscosity with increases in heat, and as such the mixing apparatus may be heated to accommodate the addition of the HVLCM material or other similar materials. However, the mixing and processing conditions should take into account the final integrity of the composition and accordingly the mixing conditions may be selected so as to have a low-sheer effect on the composition, and/or to avoid any extended or pronounced excursions into high or low heat conditions. Once the composition has been properly combined, an appropriate amount of the resulting liquid mixture can be placed into a suitable capsule, such as a gelatin or HPMC capsule to provide an oral pharmaceutical dosage form. Alternative liquid compositions may include emulsifying the mixture in water, and introducing this emulsion into a capsule.

Figure 2:
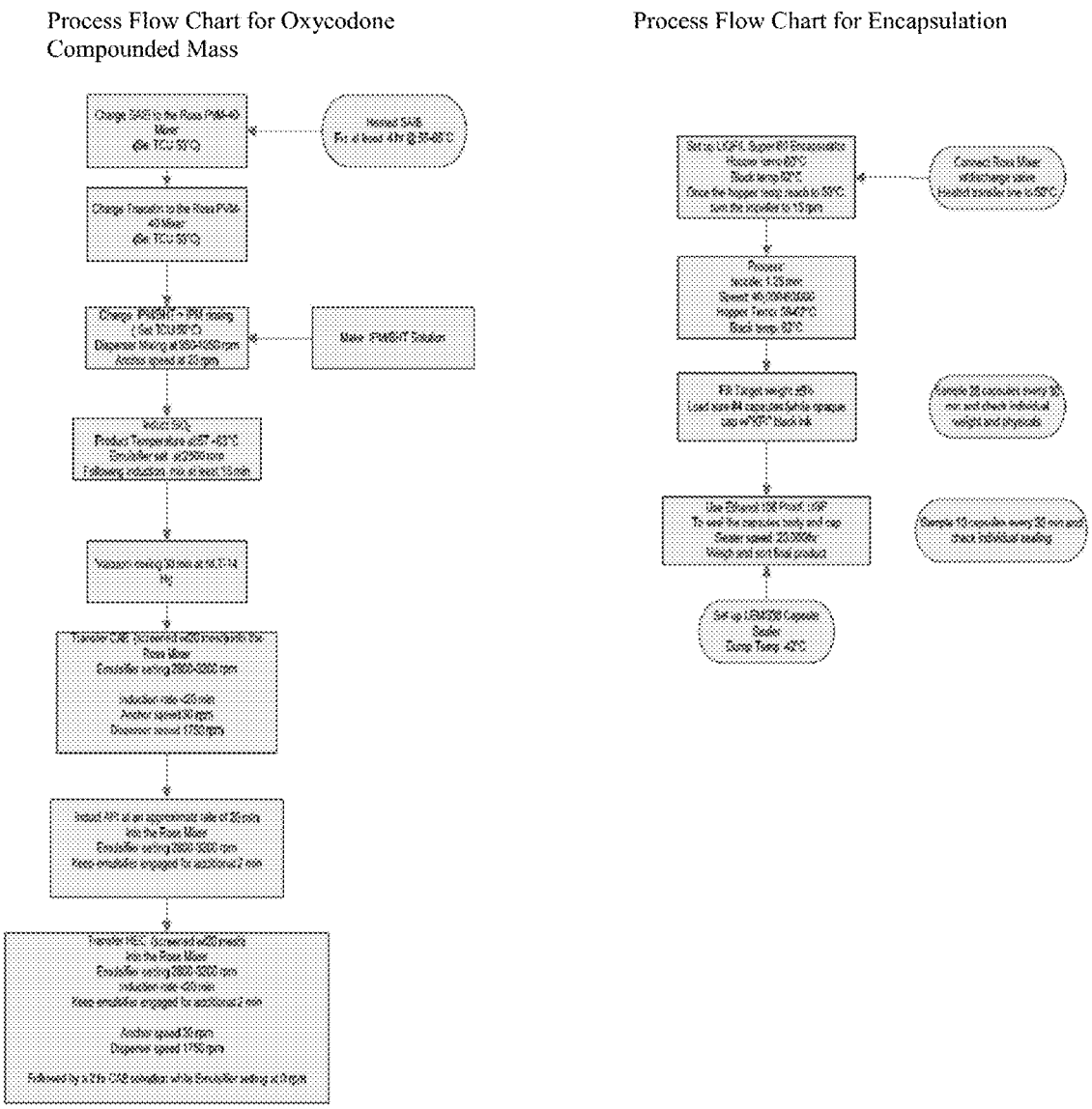
FIG. 2 shows a flow diagram of an exemplary composition preparation and encapsulation method.

An additional, exemplary composition preparation and encapsulation scheme is provided in FIG. 2.

In some embodiments, an oral dosage form is provided which is composed of a liquid composition containing the active agent and any additional components within an enclosure or capsule, e.g., a biodegradable enclosure or capsule, such as a capsule or a gelatin capsule ("gelcap"), wherein the capsule is made of a substance that degrades or otherwise dissociates when exposed to conditions present in the gastrointestinal tract of a mammal. Capsules and gelcaps are well known in drug delivery technology and one of skill could select such a capsule as appropriate for delivery of a particular active agent. Once the capsule has dissolved or dissociated from the composition, the disclosed compositions generally remains intact, especially for hydrophobic compositions, and passes through the GI tract without emulsification or fragmentation.

In some embodiments a suitable capsule includes gelatin or synthetic polymers such as hydroxyl ethyl cellulose and hydroxyl propylmethyl cellulose. Gelcaps can be of the hard or soft variety, including, for example, polysaccharide or hypromellose acetate succinate based caps (e.g., Vegicaps brand, available from Catalent). The capsule can also be coated with an enteric coating material such as AQIAT (Shin-Etsu) to delay release.

As discussed in the Examples below, certain time-dependent changes in drug release performance have been observed for Reference Formulation A. Without intending to be bound by any particular theory, it is believed that reducing the amount of water available to the compositions of the present disclosure may minimize these effects. For example, by utilizing HPMC capsules (~4-6% w/w water) instead of gelatin capsules (~13-16% w/w water) the amount of water available to the compositions may be reduced. Accordingly, in some embodiments, the compositions of the present disclosure are specifically encapsulated in capsules having lower water content than gelatin capsules, e.g., water content of less than 15% w/w, less than 14% w/w, less than 13% w/w, less than 12% w/w, less than 11% w/w, or less than 10% w/w. In some embodiments, the compositions of the present disclosure are encapsulated in capsules having a water content of from about 1% w/w to about 10% w/w, from about 1% w/w to about 9% w/w, from about 1% w/w to about 8% w/w, from about 1% w/w to about 7% w/w, from about 1% w/w to about 6% w/w, from about 1% w/w to about 5% w/w, from about 1% w/w to about 4% w/w, from about 1% w/w to about 3% w/w, or from about 1% w/w to about 2% w/w. Suitable HPMC capsules may include, for example, V-Caps™, V-caps Plus™, Quali-V™, Vegi-Caps™, Embo Caps-Vg™, and HMPC capsules provided by Baotou Capstech Co., Ltd, and Zhejiang LinFeng Capsules Co. Ltd.

In some embodiments, a composition according to the present disclosure is one which has relatively low water content. For example, in some embodiments, a composition according to the present disclosure does not include more than 5% water by weight, based on total weight of the composition. For example, the composition may include water at less than 5% by weight, less than less than 4% by weight, less than 3% by weight, or less than 2% by weight, based on the total weight of the composition. In some embodiments, a composition according to the present disclosure includes water at from about 1.0 to about 5.0% by weight, based on total weight of the composition, e.g., at from about 1.0 to about 4.5% by weight, at from about 1.0 to about 3.0% by weight, at from about 1.0 to about 2.5% by weight, at from about 1.0 to about 2.0% by weight, or at from about 1.0 to about 1.5% by weight, based on total weight of the composition.

In some embodiments, the water content of the composition and the capsule combined is less than about 5% by weight based on the total weight of the composition and the capsule combined, e.g., less than about 4% by weight, less than about 3% by weight, or less than about 2% by weight based on the total weight of the composition and the capsule combined. In some embodiments, the water content of the composition and the capsule combined is from about 5% by weight to about 4% by weight, from about 4% by weight to about 3% by weight, from about 3% by weight to about 2% by weight based on the total weight of the composition and the capsule combined, or from about 2% by weight to about 1% by weight based on the total weight of the composition and the capsule combined.

The time-dependent change in release performance may also be addressed by formulating the various components of the composition in specific concentration ranges and/or at specific ratios for oral dosage forms. Accordingly, the present disclosure provides a method of orally administering a composition, including: reducing a time-dependent change in an in vitro release profile of a composition by formulating the composition to include, in addition to a pharmacologically active agent, about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere, about 31% by weight to about 45% by weight, based on total weight of the composition, of a solvent, about 2% by weight to about 10% by weight, based on total weight of the composition, of a rheology modifier, and a cellulose acetate butyrate; and orally administering the composition.

In some embodiments, the present disclosure provides a method of reducing a time-dependent change in an in vitro release profile of a pharmacologically active agent from a composition, wherein the method includes formulating the pharmacologically active agent with (a) a high viscosity liquid carrier material (HVLCM) having a viscosity of at least 5000 cP at 37 C that does not crystallize neat at 25 C and 1 atmosphere, (b) a solvent, (c) a rheology modifier and (d) cellulose acetate butyrate, such that the composition includes about 35% by weight to about 45% by weight, based on total weight of the composition, of the high viscosity liquid carrier material (HVLCM) having a viscosity of at least 5000 cP at 37 C that does not crystallize neat at 25 C and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate.

In some embodiments, the present disclosure provides a use of (a) a high viscosity liquid carrier material (HVLCM) having a viscosity of at least 5000 cP at 37 C that does not crystallize neat at 25 C and 1 atmosphere, (b) a solvent, (c) a rheology modifier and (d) cellulose acetate butyrate, for reducing a time-dependent change in an in vitro release profile of a pharmacologically active agent from a composition, wherein the use includes formulating the pharmacologically active agent with (a) the high viscosity liquid carrier material (HVLCM) having a viscosity of at least 5000 cP at 37 C that does not crystallize neat at 25 C and 1 atmosphere, (b) the solvent, (c) the rheology modifier and (d) cellulose acetate butyrate, thereby providing a composition that includes about 35% by weight to about 45% by weight, based on total weight of the composition, of the high viscosity liquid carrier material (HVLCM) having a viscosity of at least 5000 cP at 37 C that does not crystallize neat at 25 C and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere, a solvent; about 2% by weight to about 10% by weight, based on total weight of the composition, of a rheology modifier, and a cellulose acetate butyrate (CAB), wherein the HVLCM and the solvent are present in the composition at a ratio of about 1.3:1.0 to about 1.0:1.0; and orally administering the composition.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio of about 1.3:1.0:0.3 to about 1.0:1.0:0.05; and orally administering the composition.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition; and orally administering the composition.

In some embodiments, the present disclosure provides a method of orally administering a composition, including: reducing a storage time-dependent change in a release profile of a composition by formulating the composition to include, in addition to a pharmacologically active agent, means for the reducing a storage time-dependent change in a release profile of the composition relative to Reference Formulation A.

In some embodiments, the present disclosure provides a method for treating pain in a subject, the method including: orally administering to the subject a composition including an opioid; a high viscosity liquid carrier material (HVLCM) having a viscosity of at least 5000 cP at 37° C. that does not crystallize neat at 25° C. and 1 atmosphere; a solvent; a network former; and silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated.

In some embodiments, the present disclosure provides a method for treating pain in a subject, the method including: orally administering to the subject a composition including an opioid; sucrose acetate isobutyrate (SAIB); triacetin; isopropyl myristate (IPM); cellulose acetate butyrate (CAB); hydroxyethyl cellulose (HEC); and silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated.

In some embodiments, the present disclosure provides a method for treating pain in a subject, the method including: orally administering to the subject a composition including oxycodone; about 35% by weight to about 45% sucrose acetate isobutyrate (SAIB) relative to the total weight of the composition; about 31% by weight to about 45% of triacetin relative to the total weight of the composition; about 2% by weight to about 10% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.4% by weight to about 5.4% by weight of silicon dioxide relative to the total weight of the composition, wherein one or more symptoms or signs associated with the subject's pain is alleviated.

In some embodiments, the present disclosure provides a method for treating pain in a subject, the method including: orally administering to the subject a composition including oxycodone; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition, wherein one or more symptoms or signs associated with the subject's pain is alleviated.

In some embodiments, the present disclosure provides a method for treating pain in a subject, the method including: orally administering to the subject a composition including about 5% by weight of oxycodone relative to the total weight of the composition; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition, wherein one or more symptoms or signs associated with the subject's pain is alleviated.

In some embodiments, the present disclosure provides a method for treating pain in a subject, the method including: orally administering to the subject a composition including oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide, wherein the silicon dioxide is present in the composition at about 2.9% by weight relative to the total weight of the composition, wherein the composition is formulated for oral administration, and one or more symptoms or signs associated with the subject's pain is alleviated.

In some embodiments, the present disclosure provides a method of orally administering a composition, including: improving reproducibility of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and orally administering the composition.

In some embodiments, the present disclosure provides a method of orally administering a composition, including: decreasing the variability of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and orally administering the composition.

In some embodiments, the present disclosure provides a method of orally administering an encapsulated composition, including: forming a composition including: a pharmacologically active agent, a high viscosity liquid carrier material (HVLCM) having a viscosity of at least 5000 cP at 37° C. that does not crystallize neat at 25° C. and 1 atmosphere, a solvent, a network former, and a mineral particle, wherein the mineral particle is present in the composition in an amount from about 2.4% by weight to about 5.4% by weight relative to the total weight of the composition; improving an in vitro release profile of the composition by encapsulating the composition in a capsule including hydroxypropyl methylcellulose to form an encapsulated composition; and orally administering the encapsulated composition.

In some embodiments, the present disclosure provides a method of orally administering an encapsulated composition, including: forming a composition including: a pharmacologically active agent, a high viscosity liquid carrier material (HVLCM) having a viscosity of at least 5000 cP at 37° C. that does not crystallize neat at 25° C. and 1 atmosphere, a solvent, a network former, and a mineral particle, wherein the mineral particle is present in the composition in an amount from about 2.4% by weight to about 5.4% by weight relative to the total weight of the composition; reducing exposure of the composition to water by encapsulating the composition in a capsule including hydroxypropyl methylcellulose to form an encapsulated composition; and orally administering the encapsulated composition.

In certain embodiments, the compositions of the present disclosure may be formulated so as to produce particular controlled plasma levels of an active agent over a particular period, e.g., to maintain a plasma level within an appropriate therapeutic range. An appropriate therapeutic range will vary depending on the active agent, but can range from femtogram/mL levels up to above microgram/mL levels for a desired period of time. For example, a single dose of a composition disclosed herein may result in maintenance of plasma levels of greater than 5 ng/mL for a period of greater than 8 hours. In other embodiments, the plasma level achieved using a single dose may be greater than 5 ng/mL for a period of greater than 10 hours, greater than 12 hours, greater than 14 hours, greater than 16 hours, greater than 18 hours, or greater than 20 hours. In yet other embodiments, the plasma level achieved using a single dose may be greater than 5 ng/mL, greater than 10 ng/mL, greater than 15 ng/mL, greater than 20 ng/mL, greater than 30 ng/mL, greater than 40 ng/mL, or greater than 50 ng/mL for a period of 4, 8, 10, 12, 14, 16, 18, 20 or 24 hours. The maximum plasma concentration of an active agent may be reached at a time following administration from between 0.1 hr to about 24 hr, or from about 0.25 hr to 10 hr, or from about 0.25 hr to 8 hr, or from about 0.5 hr to 6 hr, or from about 0.5 hr to 4 hr, or from about 0.5 hr to 2 hr, or from about 0.5 hr to 1 hr. The time to maximum plasma concentration may be adjusted by adjusting various components of the controlled release carrier system as taught herein.

The plasma levels obtained may be adjusted by adjusting the dose of the active agent, and/or by adjusting the components of the composition, and desirable plasma levels will depend on the therapeutic range or its index for any particular active agent. It is readily within the skill of one in the art to determine the desired therapeutic index.

The rate of active agent release from the composition may be varied depending on the agent used and the dosage required. Release rates may be different in different parts of the GI tract, and release rates may be averaged over the time of transit through the GI tract (approximately 8-24 hrs). Typical average release rates may vary substantially. For many active agents, they may range from about 0.01 to 500 mg/hr, from 0.5 to 250 mg/hr, 0.75 to 100 mg/hr, 1.0 to 100 mg/hr, 2.0 to 100 mg/hr, 5 to 100 mg/hr, 10 to 100 mg/hr, 10 to 80 mg/hr, 20 to 50 mg/hr, or about 20 to 40 mg/hr.

Dosage regimens for a particular active agent of interest may be determined by the physician in accordance with standard practices. Once per day (QD) or twice per day (BID) dosing may be used to maintain a sufficient clinical effect, e.g., to maintain pain relief.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near one atmosphere. Standard abbreviations may be used, e.g., s or sec, second(s); min, minute(s); h or hr, hour(s); and the like.

Example 1: Time-Dependent Changes in Drug Release Performance of Reference Formulation Reference Formulation A is a capsule product that provides extended release of oral oxycodone. The product is formulated to resist tampering and abuse. Although the product is a semi-solid matrix, the composition is manufactured by a standard liquid-fill manufacturing process. A common viscous composition of the active pharmaceutical ingredient (API), colloidal silicon dioxide (CSD) and hydroxyethyl cellulose (HEC) suspended in a cellulose acetate butyrate (CAB)/sucrose acetate isobutyrate (SAIB)/triacetin (TA)/isopropyl myristate (IPM)/Butylated hydroxytoluene (BHT) solution is filled into a range of capsule sizes to accommodate various dosage strengths.

The composition of Reference Formulation A is as provided below in Table 1.

TABLE 1

| Component | Function | % w/w |
|---|---|---|
| Micronized oxycodone base | Active Pharmaceutical Ingredient | 5.13 |
| Sucrose acetate isobutyrate (SAIB) | An esterified sucrose derivative, that is a high viscosity, hydrophobic carrier molecule, which is the base component in the extended release matrix | 40.98 |
| Triacetin (TA) | Hydrophilic solvent that participates in the dissolution or suspension of other components in the extended release matrix | 27.32 |
| Isopropyl Myristate (IPM) | Rheology modifier that participates in the control of drug diffusion from the extended release matrix | 14.23 |
| Cellulose acetate butyrate (CAB) | Polymer additive for abuse deterrence and extended release | 4.74 |
| Hydroxyethyl cellulose (HEC) | Non-ionic, water soluble polymer that participates in the control of drug diffusion from the extended release matrix | 5.69 |
| Colloidal silicon dioxide (CSD) | Suspending agent, viscosity modifier | 1.90 |
| Butylated hydroxytoluene (BHT) | Antioxidant | 0.02 |
| Hard shell capsule | Dosage form encapsulation | Gelatin |

In vitro analysis of Reference Formulation A has shown that it may exhibit time-dependent changes in drug release performance. This is shown, for example, in FIG. 1A, wherein Reference Formulation A (with BHT) stored at 25° C./60% RH for a 22 months period exhibited a decrease in the mean release profile for oxycodone.

Example 2: Gelatin vs. HPMC Capsules

It was hypothesized that phase immiscibility could be responsible for the time dependent changes in drug release performance observed for Reference Formulation A. It was further hypothesized that reducing the amount of available water by changing the capsule shell from gelatin (~13-16% w/w water) to HPMC (~4-6% w/w water) could minimize these effects.

Materials and Methods

Figure 1B:
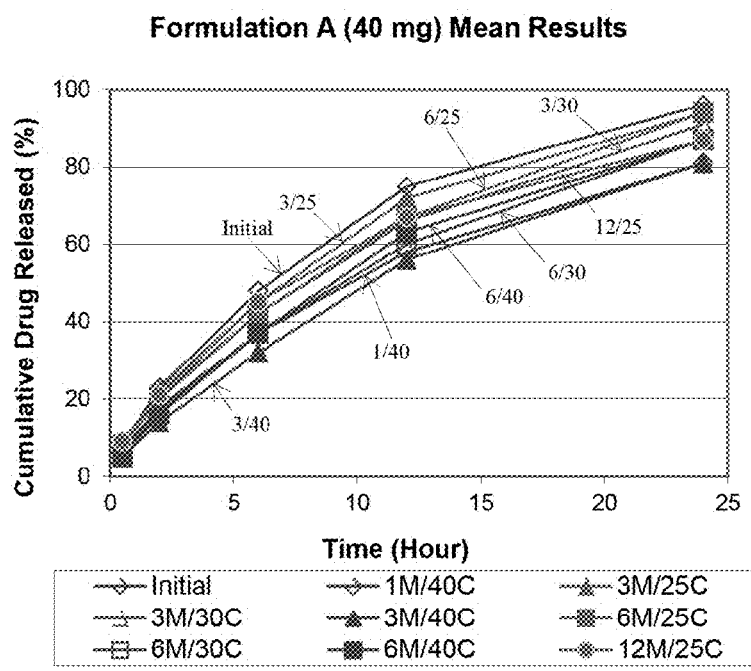
FIG. 1B provides graphs showing the effect of formulating Reference Formulation A in gelatin (Panel A) vs. HPMC (Panel B) capsules.
Figure 1B:
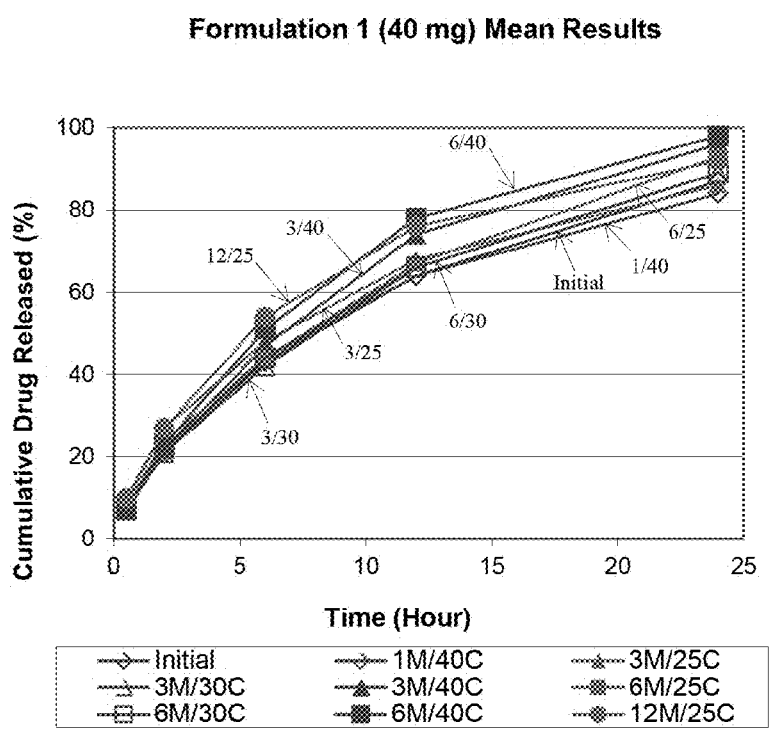

Dissolution data utilizing the Apparatus 2 method (described below) for Reference Formulation A (without BHT) in gelatin or HPMC capsules stored up to 12 months at 25° C./60% RH, 30° C./65% RH and 40° C./75% RH are shown in FIG. 1B, Panels A and B.

Twelve capsules from each formulation were tested with USP Apparatus 2 to evaluate the effect on inter-capsule dissolution variability. The release rate of oxycodone base was determined using a USP Apparatus 2 dissolution tester.

Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12 and 24 hours. A 1 mL sample was taken at each time point and assayed using reverse-phase HPLC at 240 nm wavelength. The mobile phase included 0.35% (w/v) SDS/0.7% (w/v) acetic acid/44% (v/v) acetonitrile in water.

Separately, the total water content of a freshly prepared Reference Formulation A formulation in gelatin vs. HPMC capsules was determined. Two preparations were tested for each formulation. The % water (or moisture) was determined by Karl Fischer Coulometric Apparatus and each preparation utilized 5 capsules.

Results

The results for the dissolution experiments are provided in FIG. 1B, Panels A and B. As shown in Panel A, Reference Formulation A in gelatin capsules exhibits a decrease in the mean release profile following storage for 12 months at 25° C., 6 months at 30° C., 6 months at 40° C. and 3 months at 40° C. relative to the initial release profile. In contrast, Reference Formulation A in HPMC capsules exhibited a more stable dissolution profile following storage under the above conditions, with the exception of the 40° C. storage conditions. Inter-capsule dissolution variability was not significantly reduced for Formulation A in HPMC relative to Formulation A in gelatin under the above testing conditions.

The total average water content of Reference Formulation A in gelatin vs. HPMC capsules was found to be 2.2% w/w vs. 1.4% w/w respectively.

Example 3: Preparation of Extended Release Oxycodone Compositions for PK and BA Analysis Compositions were prepared, for example, as follows to provide the compositions indicated in Table 2 (below). Sucrose Acetate Isobutyrate (SAIB) was transferred into a Ross mixer at an elevated temperature (50° C.) and dissolved in triacetin (TA) and isopropyl myristate (IPM) and uniformly mixed. When present in the composition, butylated hydroxytoluene (BHT) was added prior to uniformly mixing with TA and IPM. Colloidal silicon dioxide (CSD) particles were added into the SAIB solution in the Ross mixer and were dispersed uniformly. Cellulose acetate butyrate (CAB) particles were sieved and fed into the Ross mixer and dispersed and dissolved in the content of the mixer at the elevated temperature. The oxycodone particles were introduced into the Ross mixer and dispersed in the content of the mixer, keeping the same process temperature. Hydroxyethyl cellulose (HEC) was then added into the Ross mixer and dispersed. In order to assure complete dispersion of all particles (oxycodone, $SiO_2$, HEC), high shear mixers (dispenser and emulsifier) may be used for pre-set time periods after the introduction of these solid particles into the Ross mixer.

For the capsule filling operation, the compositions were transferred from the Ross mixer via a temperature controlled (or insulated) (at 50-60° C.) pump and hoses to the capsule filling equipment. The temperature of the compositions was maintained at 50-60° C. during the capsule filling operations.

Individual compositions were encapsulated in size 4 (5 mg dose) or size 00 (40 mg dose) gelatin or HPMC capsules. Encapsulation was achieved using a Capsugel CFS 1000™ apparatus. It was observed that increasing the temperature of the composition and the filling pump, e.g., from about 60° C. to about 75° C., reduced the stringiness of the composition, thereby facilitating the separation of the composition from the nozzle into the capsule shell and allowing clean movement to the next capsule station. The reduced stringiness of the composition also allowed the motor speed setting (fill rate) to be increased, e.g., to a motor speed set point range of about 50% to about 60% (500-600 capsules per hour). Size 00 capsules were successfully filled using, e.g., a 1.8 mm filling nozzle. Size 4 capsules were successfully filled using, e.g., a 2.0-2.2 mm nozzle. An exemplary composition preparation and encapsulation method is depicted graphically in FIG. 2.

The compositions indicated in Table 2 (below) were prepared for use in Examples 4-6 below. Composition components were blended and individual compositions were encapsulated in gelatin or HPMC capsules as described above.

TABLE 2

| | % w/w of component of each formulation Formulation Identification | | | | | | | | | |
|---|---|---|---|---|---|---|---|---|---|---|
| Composition | Reference Formulation A in Gelatin without BHT | 1 (Reference Formulation A in HPMC without BHT) | 2 | 3 | 4 | 5 | 6 | 7 | 8 | 9 |
| Micronized oxycodone base | 5.13 | 5.13 | 5.13 | 5.13 | 5.13 | 5.13 | 5.13 | 5.13 | 5.13 | 5.13 |
| Sucrose acetate isobutyrate (SAIB) | 40.99 | 40.99 | 46.69 | 48.11 | 40.98 | 40.98 | 36.74 | 38.98 | 40.38 | 39.98 |
| Triacetin (TA) | 27.32 | 27.32 | 27.32 | 27.31 | 32.55 | 39.08 | 37.56 | 39.08 | 39.08 | 39.08 |
| Isopropyl Myristate (IPM) | 14.23 | 14.23 | 14.23 | 7.12 | 9.00 | 2.48 | 8.25 | 2.48 | 2.48 | 2.48 |
| Cellulose acetate butyrate (CAB) | 4.74 | 4.74 | 4.74 | 4.74 | 4.74 | 4.74 | 4.74 | 4.74 | 4.74 | 4.74 |
| Hydroxyethyl cellulose (HEC) | 5.69 | 5.69 | 0.00 | 5.69 | 5.69 | 5.69 | 5.69 | 5.69 | 5.69 | 5.69 |
| Colloidal silicon dioxide (CSD) | 1.90 | 1.90 | 1.90 | 1.90 | 1.90 | 1.90 | 1.90 | 3.90 | 2.50 | 2.90 |
| Capsule Shell | Gelatin | HPMC | HPMC | HPMC | HPMC | HPMC | HPMC | HPMC | HPMC | HPMC |

Example 4: PK Analysis of Extended Release Oxycodone Compositions (Ref. Formulation A and Formulations 2, 3 and 4)

Materials and Methods

This study was an open-label, single-dose, randomized, crossover study of the pharmacokinetics and bioavailability of oxycodone after administration of 40 mg doses of four extended release oxycodone compositions and oxycodone in solution in fed state to healthy volunteers.

The study was intended to evaluate the in vivo performance of several variants of Reference Formulation A (primarily HEC, IPM, and SAIB) and the effect of changing the capsule shell from gelatin to hydroxylpropyl methylcellulose (HPMC).

The study was conducted as an open-label, single-dose, 5-way crossover study in 16 healthy adult volunteers. The treatments (Reference Formulation A, three modified oxycodone compositions Formulation 1 (Reference Formulation A in HPMC), Formulation 2 and Formulation 3, and an oral oxycodone solution; see Table 3) were administered under naltrexone blockade and following ingestion of an intermediate-size breakfast (~450 calories). The primary objective was to estimate the pharmacokinetics and bioavailability of oxycodone following single oral 40 mg doses of three modified compositions relative to the Reference Formulation A. The oral solution was included for the purpose of exploratory in vitro in vivo correlation analysis.

TABLE 3

| Reference Formulation A (without BHT) | Gelatin capsule shell, 40 mg oxycodone | Reference |
|---|---|---|

TABLE 3-continued

| Formulation 1 (Reference Formulation A in HPMC) | HPMC capsule shell, 40 mg oxycodone | Test |
|---|---|---|
| Formulation 2 | HPMC capsule shell without HEC, 40 mg oxycodone | Test |
| Formulation 3 | HPMC capsule shell with 50% reduced IPM content and increase in SAIB, 40 mg oxycodone | Test |
| Oral solution | Oral solution of oxycodone 40 mg | Oral solution |

Results

Figure 3:
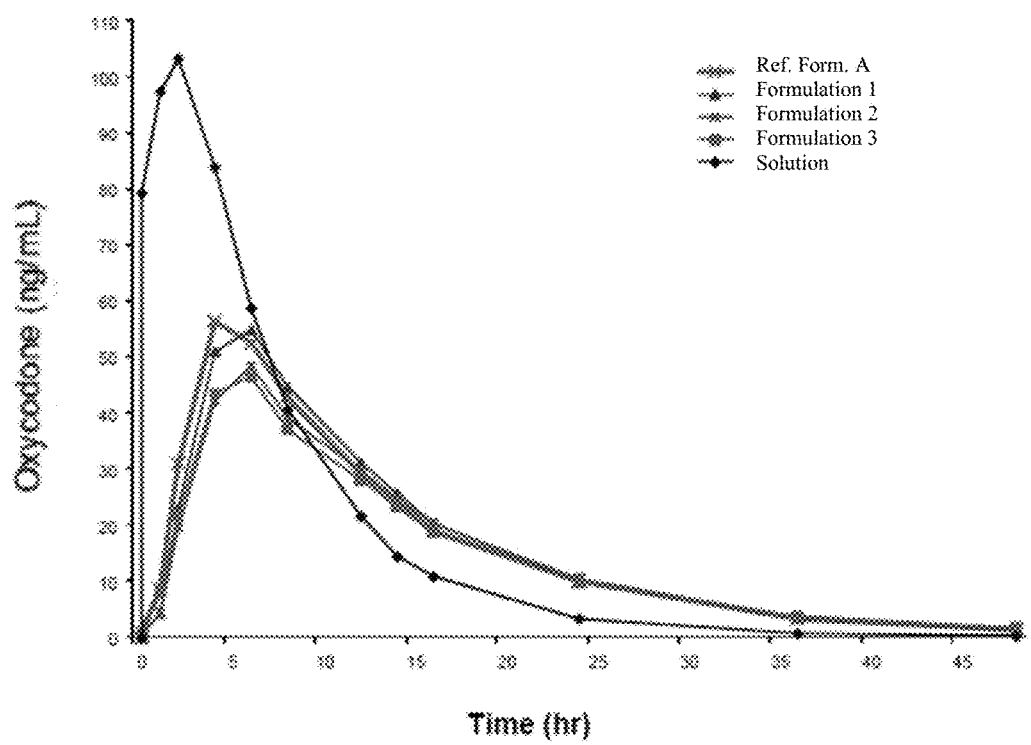
FIG. 3 is a graph showing mean plasma oxycodone concentration profiles following administration of Reference Formulation A (without BHT) and Formulations 1-3.

The mean plasma oxycodone concentration profiles are shown in FIG. 3. The mean (CV %) values for the oxycodone PK parameters are summarized in Table 4, below, along with the geometric mean ratios and 90% confidence intervals for each test composition relative to the Reference Formulation A. Compared with the rapid oral absorption characteristics of the oral solution, Reference Formulation A and the 3 modified oxycodone compositions demonstrated drug delivery characteristics consistent with extended release of the Reference Formulation A. The results demonstrated that changing the capsule shell from gelatin to HPMC did not significantly affect the controlled-release characteristics of the composition based on the geometric mean ratios for $C_{max}$ and AUC. In contrast, the $C_{max}$ and AUC values for the test Formulations 2 and 3, which involved significant changes in excipients—either a removal of HEC (Formulation 2) or a 50% reduction in IPM and corresponding increase in SAM—the key hydrophobic constituent of Reference Formulation A—(Formulation 3), were generally slightly lower on $C_{max}$ (by approx. 15-20%) than those for Reference Formulation A even though their controlled-release characteristics were retained as compared with the oral solution (Table 4). However, AUC point estimates were similar to the Reference Formulation A (within approx. 90-100% of Reference Formulation A).

TABLE 4

PK Summary

| Parameter (Units) | Reference Formulation A (without BHT) (N = 14) | Formulation 1 (N = 16) | Formulation 2 (N = 14) | Formulation 3 (N = 13) | Oral Solution (N = 14) |
|---|---|---|---|---|---|
| Cmax (ng/mL) | 62.8 (34) | 58.5 (26) | 51.1 (26) | 55.0 (36) | 116 (20) |
| Tmax (hr) | 5.0 (2.0-6.0) | 6.0 (2.0-6.0) | 6.0 (4.0-6.1) | 4.0 (2.0-8.0) | 2.0 (0.5-6.0) |
| AUClast (ng * hr/mL) | 752 (12) | 745 (21) | 691 (27) | 676 (24) | 817 (17) |
| AUCinf (ng * hr/mL) | 772 (13) | 764 (22) | 712 (28) | 708 (23) | 818 (17) |
| t½ (hr) | 7.88 (3.01) | 8.01 (3.03) | 8.56 (2.66) | 9.72 (3.86) | 5.83 (0.58) |

BA Assessment

Bioavailability (%) Relative to Formulation A [90% Confidence Interval]

| Parameter | Formulation 1 | Formulation 2 | Formulation 3 |
|---|---|---|---|
| Cmax | 92.8 [77.5, 111.0] | 80.1 [66.5, 96.4] | 87.5 [72.5, 105.6] |
| AUCinf | 100.5 [91.4, 110.5] | 92.1 [83.5, 101.5] | 91.6 [83.0, 101.1] |

Geometric mean (% CV) for AUC, Cmax; median (range) for Tmax; arithmetic mean (±SD) for t½.

Example 5: PK and BA Analysis of Extended Release Oxycodone Compositions (Ref. Formulation A and Formulations 4, 5, 6, 7 and $5^a$)

Materials and Methods

This study was intended to evaluate the in vivo performance of several variants of Reference Formulation A (primarily changes in the relative amounts of TA and IPM). In addition, Formulation 7—a slight variant of Formulation 5, differing only with respect to silicon dioxide (CSD) content—was evaluated as an add-on treatment arm to complete the study. Likewise, the pharmacokinetics and dose proportionality of a 5 mg dose of the 40 mg test Formulation 5 after the initial 4-way crossover portion of the study with Reference Formulation A, 4, 5, and 6 was completed. HPMC capsule shells were used in each modified oxycodone composition, while gelatin capsule shells were used for Reference Formulation A.

This was an open-label, single-dose, randomized, crossover study in healthy adult (18-55 years) male and female volunteers. Twenty (N=20) subjects who met study eligibility criteria were enrolled. The study occurred in three parts. In Part I, three modified oxycodone compositions (Formulations 4, 5, and 6) were compared with Reference Formulation A using a standard single-dose, 4-period, crossover study design, with at least a one-week washout period between doses. Following the completion of Part I, the pharmacokinetic results were reviewed and the test composition that had the PK profile closest to that of Reference Formulation A was selected for Part II (Period 5) to evaluate dose proportionality of the 5 mg strength. After completion of Part II, the protocol was amended to estimate the relative bioavailability of an additional composition (Formulation 7), as part of an add-on, fixed-sequence study design (Part III, Period 6), in the same study population.

All compositions were administered under naltrexone blockade and following ingestion of an intermediate-size breakfast (~450 calories).

Results

Figure 4:
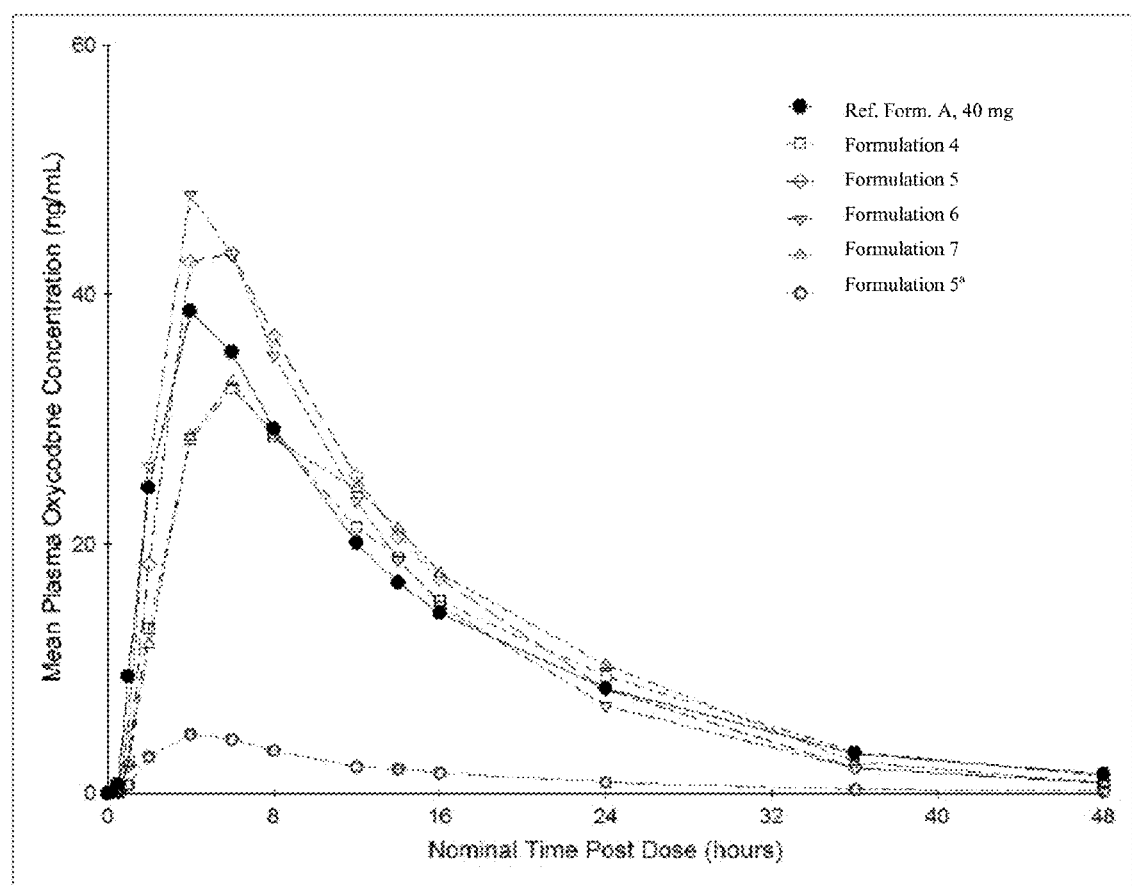
FIG. 4 is a graph showing mean plasma oxycodone concentration profiles following administration of Reference Formulation A (without BHT) and Formulations 4-7 and Formulation $5^a$.

The mean plasma oxycodone concentration profiles and summary statistics for oxycodone PK parameters following single oral doses of each composition tested in this study are shown in FIG. 4 and Table 5, respectively. The initial study results indicated that Formulation 5 had the oxycodone PK and BA characteristics closest to Reference Formulation A with respect to in vivo performance. Therefore, Formulation 5 was selected to establish the dose-proportionality relationship between the 5 mg and 40 mg dosage strengths. The statistical analysis results for relative bioavailability of Formulations 4, 5, 6, and 7 vs. Reference Formulation A, and for the dose proportionality relationship with the 5 mg dosage form (Formulation 5) are also shown in Table 5.

TABLE 5

| PK Summary | | | | | | |
|---|---|---|---|---|---|---|
| Parameter (Units) | Reference Formulation A (without BHT) (N = 19) | Formulation 4 (N = 20) | Formulation 5 (N = 20) | Formulation 6 (N = 20) | Formulation 7 (N = 18) | Formulation $5^a$ (N = 19) |
| Dose | 40 mg | 40 mg | 40 mg | 40 mg | 40 mg | 5 mg |
| Cmax (ng/mL) | 41.3 (41) | 32.6 (29) | 46.4 (39) | 52.1 (35) | 35.5 (37) | 4.88 (29) |
| Tmax (hr) | 4.0 (2.0-8.0) | 6.0 (4.0-12.0) | 6.0 (4.0-8.0) | 4.0 (2.0-12.0) | 6.0 (4.0-14.0) | 4.0 (2.0-8.0) |
| AUClast (ng*hr/mL) | 581 (23) | 523 (25) | 592 (22) | 587 (19) | 571 (19) | 62.8 (27) |
| AUCinf (ng*hr/mL) | 605 (23) | 544 (24) | 600 (22) | 596 (19) | 580 (19) | 66.4 (26) |
| $t_{1/2}$ (hr) | 9.20 + 2.91 | 8.95 + 2.83 | 6.70 + 1.14 | 7.07 + 1.81 | 6.36 + 1.74 | 8.65 + 2.74 |

| BA Assessment | | | | | |
|---|---|---|---|---|---|
| Parameter | Bioavailability (%) Relative to Formulation A [90% Confidence Interval] | | | | |
| Formulation | 4 | 5 | 6 | 7 | $5^b$ |
| Dose | 40 mg | 40 mg | 40 mg | 40 mg | 5 mg |
| Cmax | 79.5 [68.6, 92.1] | 113.3 [97.7, 131.3] | 127.2 [109.7, 147.3] | 85.1 [73.4, 98.6] | 84.1 [72.0, 98.2] |
| AUCinf | 89.2 [84.4, 94.2] | 98.4 [93.1, 104.0] | 97.8 [92.6, 103.3] | 93.5 [87.2, 100.2] | 88.7 [81.1, 97.1] |

Geometric mean (% CV) for AUC, Cmax; median (range) for Tmax; arithmetic mean (±SD) for $t_{1/2}$.
$^a$similar in composition to Formulation 5 except for drug content (5 mg)
$^b$dose-normalized comparison relative to Formulation 5

The above results indicate that each modified composition tested behaved like a controlled-release composition similar to the Reference Formulation A, with median $T_{max}$ values ranging between 4 and 6 hours (compared with 1-hour when oxycodone is administered as an immediate-release composition; data not shown). The study also revealed that changing the ratio of certain excipients in the Reference Formulation A can result in varying degrees of changes in oxycodone $C_{max}$ (approx. −21% to +27%), with similar extent of bioavailability.

Of the three compositions tested, Formulation 5, with a $C_{max}$ ratio of approximately 113% and 90% CI of 97.7-131.3%, was considered closest to the Reference Formulation A and, therefore, was selected for evaluation at the 5 mg dose in Part II to assess the dose proportionality relationship. In general, there was a dose-related increase in oxycodone $C_{max}$ (4.9 ng/mL vs. 46.4 ng/mL) and $AUC_{inf}$ (66.4 ng·h/mL vs. 600 ng·h/mL) as shown in Table 5.

After completing the PK evaluations for Reference Formulation A and Formulations 4, 5, and 6, an additional treatment arm was added to the study to determine the bioavailability of Formulation 7 (a slight variant of Formulation 5 with increased CSD content). The results of this study suggest that increasing CSD in the composition from 1.9% to 3.9% can potentially decrease $C_{max}$ by approximately 15% relative to Reference Formulation A, without substantially impacting the extent of absorption.

Example 6: PK Analysis of Extended Release Oxycodone Compositions (Ref. Formulation A and Formulations 8 and 9)

Materials and Methods

This study was an open-label, single-dose, randomized crossover study to evaluate the pharmacokinetics and relative bioavailability of oxycodone following oral administration of 40 mg doses.

The test compositions in this study were prepared based on the results from Example 5 above, which suggested that making intermediate adjustments to the CSD content—i.e., relative to the 1.9% CSD content in Formulation 5 and the 3.9% CSD content in Formulation 7—had the potential to provide in vivo drug delivery characteristics of the modified oxycodone composition similar to Reference Formulation A. This study was designed to evaluate the PK and bioavailability of single oral 40 mg doses of modified compositions (Formulations 8 and 9) compared with Reference Formulation A.

This was a randomized, open-label, single-dose, 4-treatment, 4-period, crossover study in healthy volunteers. Eighteen (18) subjects aged 18-55 years who met inclusion and exclusion criteria were enrolled. Two test modified oxycodone compositions (i.e., Formulations 8 and 9,) and the Reference Formulation A were evaluated under fed conditions.

All subjects were to be administered 50 mg of naltrexone HCl by mouth at the following times: 12 hours before, 30 minutes before, and 12 hours after study drug administration to minimize the risk of opioid-related AEs. The results are shown below.

Results

Figure 5:
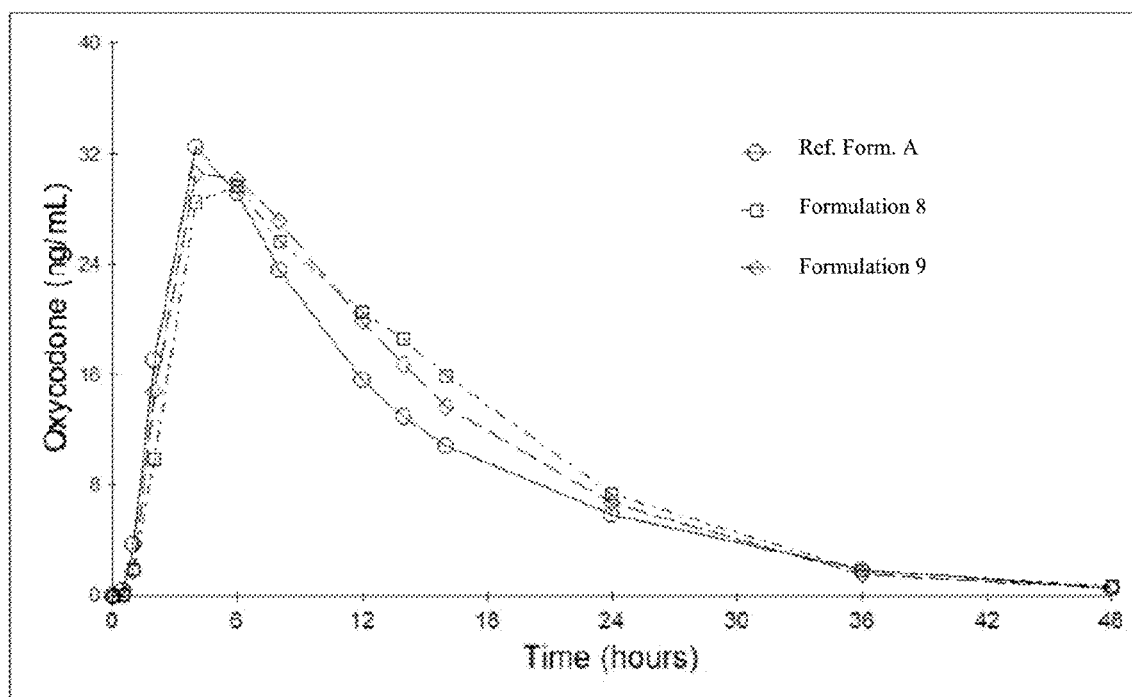
FIG. 5 is a graph showing mean plasma oxycodone concentration profiles following administration of Reference Formulation A (without BHT) and Formulations 8 and 9.

The mean plasma oxycodone concentration profiles for oxycodone PK parameters following single oral doses of each composition tested in the study are shown in FIG. 5. The summary statistics and statistical analysis are given in Table 6, below.

TABLE 6

PK Sumary

| Parameter (Units) | Reference Formulation A (without BHT) | Formulation 8 | Formulation 9 |
|---|---|---|---|
| N | 18 | 18 | 18 |
| $C_{max}$ (ng/mL) | 31.2 (50) | 32.8 (36) | 34.8 (34) |
| $T_{max}$ (hr) | 4.0 (4.0-8.0) | 6.0 (4.0-16.0) | 6.0 (4.0-12.0) |
| $AUC_{last}$ (ng*hr/mL) | 396 (37) | 454 (29) | 447 (28) |
| $AUC_{inf}$ (ng*hr/mL) | 403 (37) | 461 (29) | 453 (28) |
| $t_{1/2}$ (hr) | 7.4 ± 1.7 | 7.1 ± 1.4 | 6.7 ± 1.9 |

TABLE 6-continued

BA Assessment

| Parameter | Bioavailability (%) Relative to Formulation A [90% Confidence Interval] | |
|---|---|---|
| Formulation | 8 | 9 |
| $C_{max}$ | 105.2 [87.6, 126.3] | 111.7 [93.0, 134.1] |
| $AUC_{inf}$ | 114.5 [104.6, 125.4] | 112.4 [102.7, 123.1] |

Geometric mean (% CV) for AUC, Cmax; median (range) for Tmax; arithmetic mean (±SD) for $t_{1/2}$.

The results of the relative BA study indicate that the two modified oxycodone compositions (Formulations 8 and 9) had similar in vivo characteristics with respect to the rate and extent of oxycodone absorption. Each test composition had qualitatively similar PK profiles and bioavailability values, consistent with the desired controlled-release characteristics for a modified oxycodone composition. The $C_{max}$ and AUC ratios for Formulations 8 and 9 were both slightly higher compared to Reference Formulation A, which seemed to underperform slightly with respect to oxycodone exposure parameters ($C_{max}$ and AUC). Nevertheless, there was no apparent difference in oxycodone bioavailability ($C_{max}$ or AUC) with the CSD content used in this study for Formulation 8 (2.5%) and Formulation 9 (2.9%) based on similar point estimates and overlapping 90% confidence intervals of Test/Reference ratios. Overall, the preliminary study results indicated that Formulation 8 and 9 were indistinguishable with respect to PK and bioavailability.

Example 7: Dissolution Performance for Reference Formulation A and Formulations 1-6

Materials and Methods

Dissolution data utilizing the Apparatus 2 method (described below) for Reference Formulation A (without BHT) and Formulations 1 to 3 stored up to 12 months and Formulations 4 to 6 stored up to 6 months at accelerated conditions (40° C./75% RH) and long term storage conditions (25° C./60% RH) are shown in Table 7 and Table 8.

Twelve capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

The results of the in vitro dissolution analysis are shown in Table 7 and Table 8 below.

TABLE 7

| | | Ref. Formulation A | | | Formulation 1 | | | Formulation 2 | | | Formulation 3 | | |
|---|---|---|---|---|---|---|---|---|---|---|---|---|---|
| Storage Conditions | Check Point | Hours | Mean (%) | Range (%) | Hours | Mean (%) | Range (%) | Hours | Mean (%) | Range (%) | Hours | Mean (%) | Range (%) |
| Initial | 0 | 2 | 23 | 20-31 | 2 | 22 | 18-31 | 2 | 24 | 18-30 | 2 | 18 | 15-27 |
| | | 6 | 48 | 42-56 | 6 | 43 | 33-58 | 6 | 38 | 28-48 | 6 | 34 | 28-46 |
| | | 24 | 96 | 86-104 | 24 | 87 | 68-100 | 24 | 59 | 46-74 | 24 | 64 | 50-80 |

TABLE 7-continued

| Storage Conditions | Check Point | Ref. Formulation A | | | Formulation 1 | | | Formulation 2 | | | Formulation 3 | | |
|---|---|---|---|---|---|---|---|---|---|---|---|---|---|
| | | Hours | Mean (%) | Range (%) | Hours | Mean (%) | Range (%) | Hours | Mean (%) | Range (%) | Hours | Mean (%) | Range (%) |
| 25° C./60% RH | 3 months | 2 | 22 | 17-28 | 2 | 27 | 22-30 | 2 | 18 | 15-21 | 2 | 17 | 12-24 |
| | | 6 | 44 | 37-52 | 6 | 48 | 37-55 | 6 | 31 | 25-37 | 6 | 29 | 23-41 |
| | | 24 | 94 | 85-100 | 24 | 86 | 75-94 | 24 | 56 | 44-69 | 24 | 56 | 42-71 |
| | 6 months | 2 | 21 | 16-28 | 2 | 24 | 19-28 | 2 | 21 | 17-24 | 2 | 18 | 13-25 |
| | | 6 | 42 | 36-54 | 6 | 44 | 36-49 | 6 | 39 | 34-42 | 6 | 32 | 25-43 |
| | | 24 | 94 | 80-101 | 24 | 93 | 90-108 | 24 | 66 | 58-72 | 24 | 60 | 53-72 |
| | 12 months | 2 | 21 | 17-25 | 2 | 27 | 21-30 | 2 | 25 | 19-32 | 2 | 20 | 16-25 |
| | | 6 | 45 | 38-53 | 6 | 54 | 44-63 | 6 | 40 | 30-52 | 6 | 35 | 29-45 |
| | | 24 | 87 | 79-92 | 24 | 92 | 84-97 | 24 | 60 | 45-75 | 24 | 64 | 51-72 |
| 40° C./75% RH | 1 month | 2 | 18 | 14-28 | 2 | 21 | 17-25 | Not Evaluated | | | | | |
| | | 6 | 37 | 29-50 | 6 | 44 | 36-52 | | | | | | |
| | | 24 | 81 | 71-92 | 24 | 84 | 78-92 | | | | | | |
| | 3 months | 2 | 14 | 11-16 | 2 | 22 | 19-26 | | | | | | |
| | | 6 | 31 | 27-36 | 6 | 47 | 41-54 | | | | | | |
| | | 24 | 81 | 68-90 | 24 | 96 | 90-102 | | | | | | |
| | 6 months | 2 | 16 | 12-24 | 2 | 23 | 19-30 | | | | | | |
| | | 6 | 37 | 29-48 | 6 | 51 | 45-58 | | | | | | |
| | | 24 | 87 | 75-98 | 24 | 98 | 95-103 | | | | | | |

TABLE 8

| Storage Conditions | Check Point | Formulation 4 | | | Formulation 5 | | | Formulation 6 | | |
|---|---|---|---|---|---|---|---|---|---|---|
| | | Hours | Mean (%) | Range (%) | Hours | Mean (%) | Range (%) | Hours | Mean (%) | Range (%) |
| Initial | 0 | 2 | 25 | 18-31 | 2 | 29 | 23-35 | 2 | 28 | 24-32 |
| | | 6 | 48 | 37-59 | 6 | 61 | 53-74 | 6 | 55 | 50-63 |
| | | 24 | 85 | 72-95 | 24 | 98 | 93-103 | 24 | 95 | 90-102 |
| 25° C./60% RH | 3 months | 2 | 24 | 19-33 | 2 | 29 | 24-37 | 2 | 29 | 26-38 |
| | | 6 | 47 | 34-62 | 6 | 63 | 56-74 | 6 | 60 | 53-72 |
| | | 24 | 86 | 57-98 | 24 | 103 | 95-100 | 24 | 103 | 95-106 |
| | 6 months | 2 | 25 | 18-29 | 2 | 28 | 22-34 | 2 | 30 | 26-37 |
| | | 6 | 51 | 36-63 | 6 | 60 | 50-74 | 6 | 60 | 53-71 |
| | | 24 | 85 | 66-97 | 24 | 94 | 90-100 | 24 | 96 | 90-102 |
| 40° C./75% RH | 1 month | 2 | 21 | 18-26 | 2 | 22 | 18-28 | 2 | 28 | 26-32 |
| | | 6 | 45 | 34-54 | 6 | 54 | 45-63 | 6 | 57 | 51-65 |
| | | 24 | 89 | 74-99 | 24 | 100 | 95-106 | 24 | 88 | 85-91 |
| | 3 months | 2 | 23 | 18-29 | 2 | 27 | 23-32 | 2 | 32 | 26-37 |
| | | 6 | 45 | 29-58 | 6 | 60 | 52-68 | 6 | 64 | 55-75 |
| | | 24 | 84 | 61-95 | 24 | 100 | 93-106 | 24 | 103 | 99-110 |
| | 6 months | 2 | 25 | 21-32 | 2 | 32 | 28-37 | 2 | 33 | 27-41 |
| | | 6 | 52 | 42-67 | 6 | 63 | 55-69 | 6 | 63 | 46-76 |
| | | 24 | 86 | 74-100 | 24 | 95 | 91-98 | 24 | 98 | 93-102 |

All compositions showed extended release. Formulations 2 and 3 showed incomplete dissolution release relative to the other compositions. No significant change was observed in mean dissolution performance for Formulations 1, 4, 5 and 6 when stored up to 6 months at accelerated or long term storage conditions when compared to initial data. The inter-capsule dissolution variability was not significantly reduced for Formulations 1, 4, 5 and 6 when compared to Reference Formulation A.

The observation that the mean dissolution performance for Formulations 1, 4, 5 and 6 following storage for varying time periods and conditions did not significantly change supports the conclusion that adjusting the composition components as indicated for Formulations 4, 5 and 6 and changing the capsule shell to HPMC may decrease or eliminate the time dependent changes in drug release performance seen for Reference Formulation A.

Example 8: Preparation and Analysis of Extended Release Oxycodone Compositions (Reference Formulation A and Formulations 10-13)

Additional compositions (Formulations 10-13) with varying concentrations of isopropyl myristate (IPM) and silicon dioxide ($SiO_2$) were prepared and compared with Reference Formulation A (with BHT) to determine the effect of these components on inter-capsule dissolution variability and rheology as indicated below.

Materials and Methods

The compositions were prepared as described above for Example 3 to provide the compositions indicated in Table 9 (below).

TABLE 9

| ID | Vehicle Composition (% w/w) | | | | | | | Oxy-codone (mg) |
|---|---|---|---|---|---|---|---|---|
| | SAIB | TA | IPM | CAB | HEC | $SiO_2$ | BHT | |
| Reference Formulation A | 43 | 29 | 15 | 5 | 6 | 2 | 0.02 | 40 |
| Formulation 10 | 47 | 32 | 8 | 5 | 6 | 2 | 0.02 | 40 |
| Formulation 11 | 52 | 35 | 0 | 5 | 6 | 2 | 0.02 | 40 |
| Formulation 12 | 44 | 29 | 15 | 5 | 6 | 1 | 0.02 | 40 |
| Formulation 13 | 44 | 30 | 15 | 5 | 6 | 0 | 0.02 | 40 |

Dissolution Testing

Four capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. over the course of the 24 hour dissolution test. A 20 mesh screen hanging basket was incorporated to hold the test article and the paddle speed was set to 100 rpm. The standard sampling time points were 0.5, 2, 3, 6, 12, 18 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Rheology Testing

Samples of the above compositions (Table 9) were analyzed for rheological properties using an Anton Paar MCR301 Rheometer. The samples were exposed to increasing dynamic strain (0.1 to 100%) at a constant angular frequency (10 $s^{-1}$) at 25° C.

Results

Dissolution Testing Results

Figure 6:
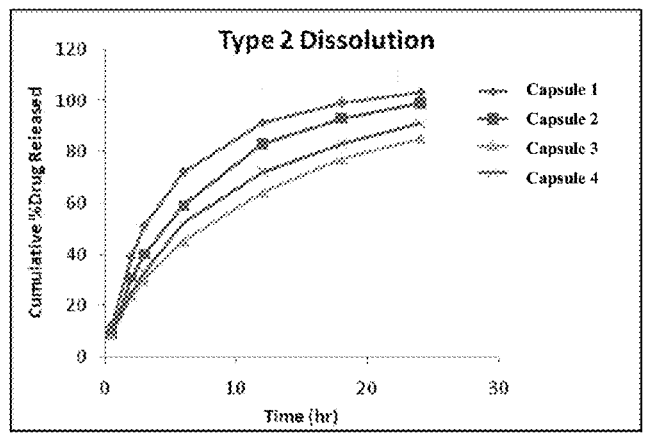
FIG. 6 provides graphs showing the results of in vitro dissolution experiments for Reference Formulation A (with BHT) (Panel A) and Formulations 10 (Panel B) and 11 (Panel C).
Figure 6:
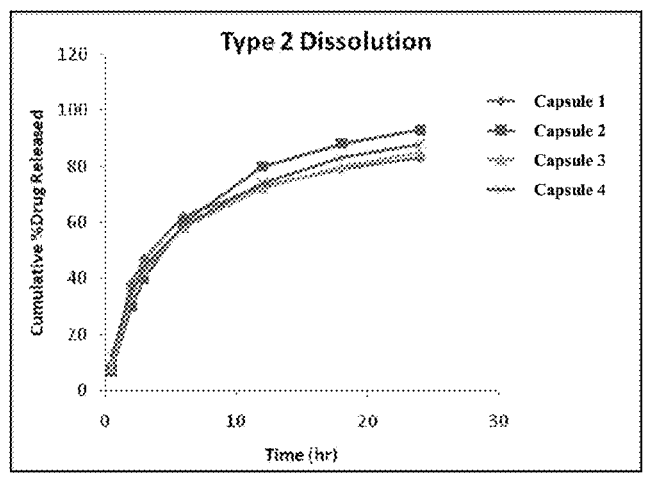
Figure 6:
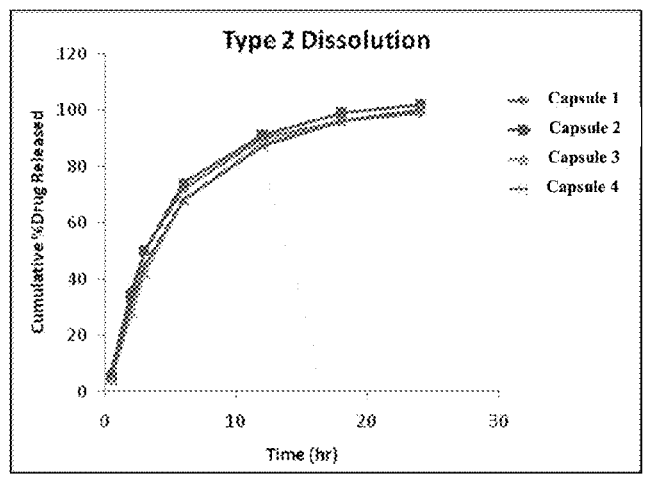
Figure 7:
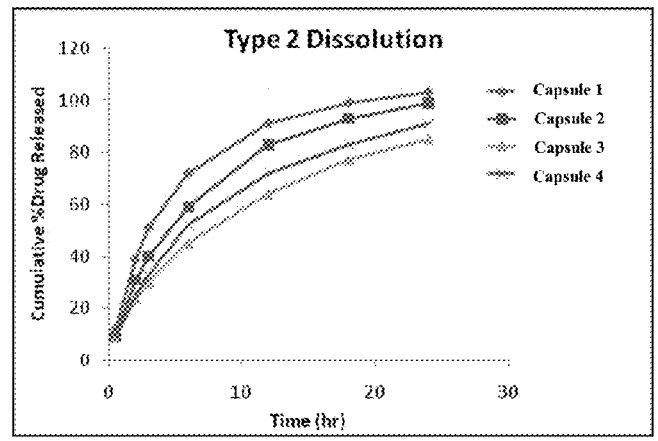
FIG. 7 provides graphs showing the results of in vitro dissolution experiments for Reference Formulation A (with BHT) (Panel A) and Formulations 12 (Panel B) and 13 (Panel C).
Figure 7:
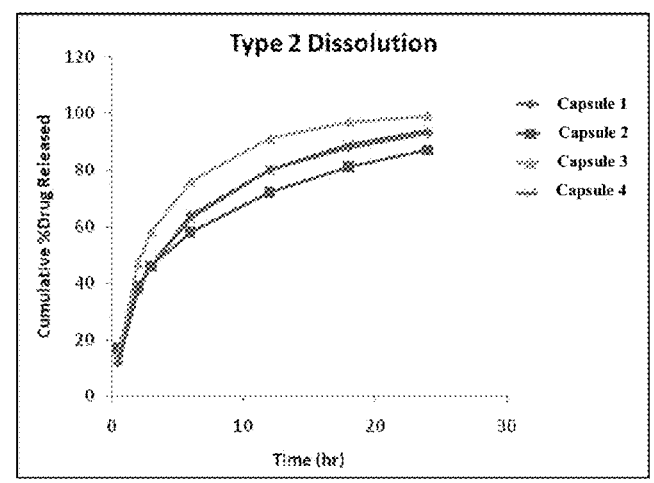
Figure 7:
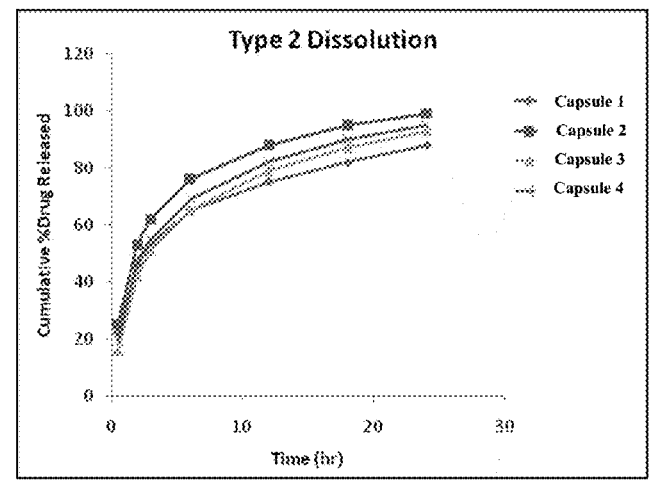
Figure 8:
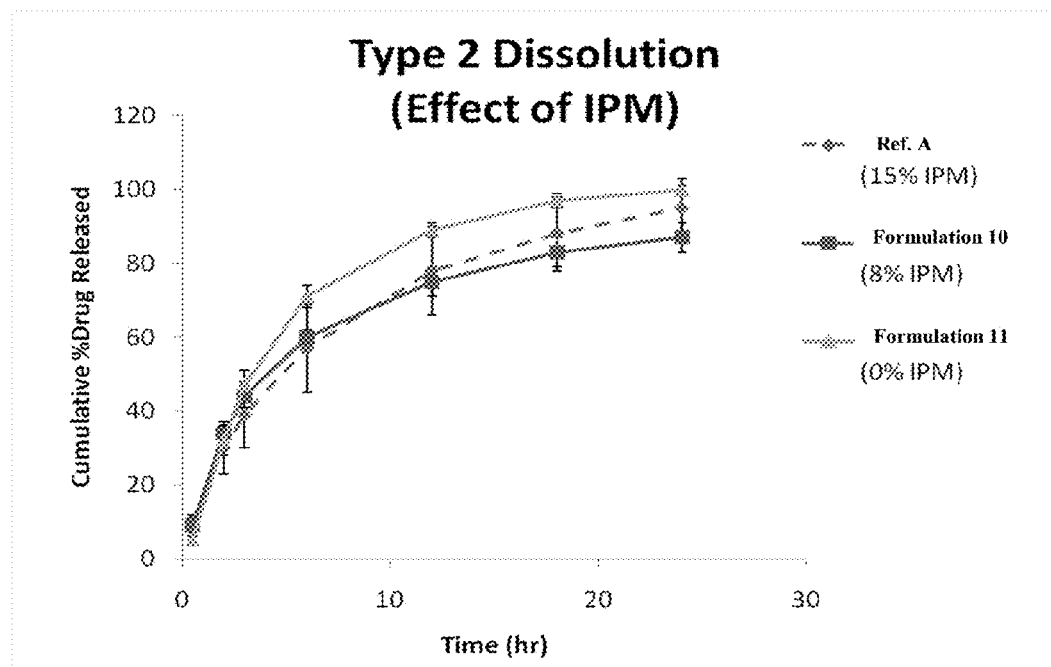
FIG. 8 provides graphs showing the effects of IPM (Panel A) and $SiO_2$ (Panel B) on mean release of oxycodone relative to Reference Formulation A (with BHT).
Figure 8:
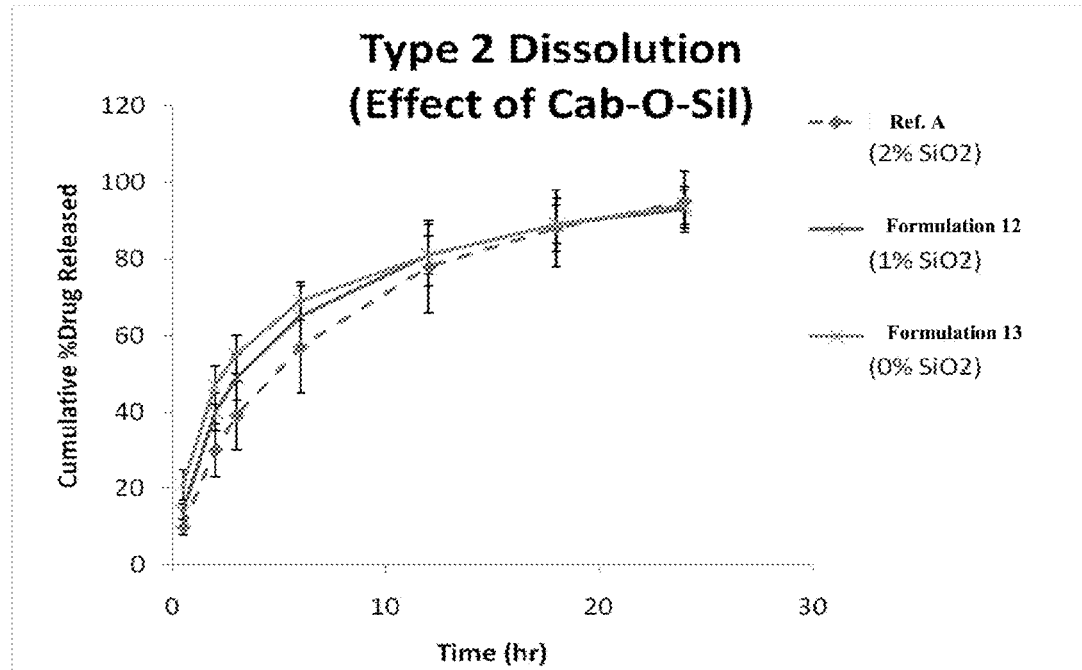

The results of the dissolution experiments are shown in FIGS. 6 and 7. The in vitro dissolution results showed a reduction in the inter-capsule dissolution variability with a reduction in the concentration of IPM in the composition (see FIG. 6, Panels A-C). Sample variability was significant when the level of $SiO_2$ in the composition was less than 2% as shown in FIG. 7, Panels A-C. The effects of adjusting the concentration of IPM and $SiO_2$ on the dissolution profiles of the compositions are shown in FIG. 8, Panels A and B, respectively, wherein the 0% IPM composition exhibited increased mean release at later time points, and the 0% $SiO_2$ composition exhibited increased mean release at earlier time points.

Rheology Testing Results

Table 10 (below) summarizes the viscoelastic outputs at the linear viscoelastic range for the rheology analysis.

TABLE 10

| ID | Description | Complex Viscosity (Pa · s) | Storage Modulus (G') (Pa) | Loss Modulus (G'') (Pa) | Damping Factor (G''/G') |
|---|---|---|---|---|---|
| Reference Formulation A | (15% IPM, 2% $SiO_2$) | 53.3 | 239 | 476 | 1.99 |
| Formulation 10 | (8% IPM) | 90.3 | 473 | 769 | 1.63 |
| Formulation 11 | (0% IPM) | 158 | 993 | 1230 | 1.24 |
| Formulation 12 | (1% $SiO_2$) | 51.8 | 229 | 464 | 2.02 |
| Formulation 13 | (0% $SiO_2$) | 41.1 | 173 | 373 | 2.16 |

Compositions with lower % IPM (as compared to Reference Formulation A) had higher complex viscosity and higher elastic property (higher G' and lower G''/G'). Without intending to be bound by any particular theory, these properties may have resulted in the observed decrease in inter-capsule dissolution variability. Compositions with lower concentrations of $SiO_2$ had lower viscosity and lower elastic property (lower G' and high G''/G') similar to Reference Formulation A. Without intending to be bound by any particular theory, the lower elastic property could relate to an increase in the deformation of the composition structure due to hydrodynamic forces in the dissolution media.

Example 9: Preparation and Analysis of Extended Release Oxycodone Compositions (Formulations 14 and 15)

Additional compositions (Formulations 14 and 15) and Formulation 1 (Reference Formulation A without BHT in HPMC capsule) were prepared and characterized with respect to inter-capsule dissolution variability, rheology and abuse deterrence characteristics as indicated below.

Materials and Methods

The compositions were prepared to provide the compositions indicated in Table 11 (below). Composition components were blended and individual compositions were encapsulated as described above, with the exception that HPMC capsules were used in place of gelatin capsules.

TABLE 11

| Composition (% w/w) | Formulation 1 | Formulation 14 | Formulation 15 |
|---|---|---|---|
| SAIB | 40.99 | 40.42 | 39.85 |
| TA | 27.32 | 26.94 | 26.56 |
| IPM | 14.23 | 14.23 | 14.23 |
| CAB | 4.74 | 4.74 | 4.74 |
| HEC | 5.69 | 5.69 | 5.69 |
| Colloidal $SiO_2$ | 1.90 | 2.85 | 3.79 |
| Micronized oxycodone base | 5.13 | 5.13 | 5.13 |
| Capsule shell | HPMC | HPMC | HPMC |

Dissolution Testing

Six capsules from each composition lot were tested according to the testing conditions discussed above to evaluate the effect on mean release and inter-capsule dissolution variability.

Rheology Testing

Triplicate samples for each composition were subjected to rheology testing as discussed above.

Abuse Deterrence

Four capsules from each composition were tested for abuse deterrence characteristics. The release rate of oxycodone base was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5, 1, and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing Results

Figure 9:
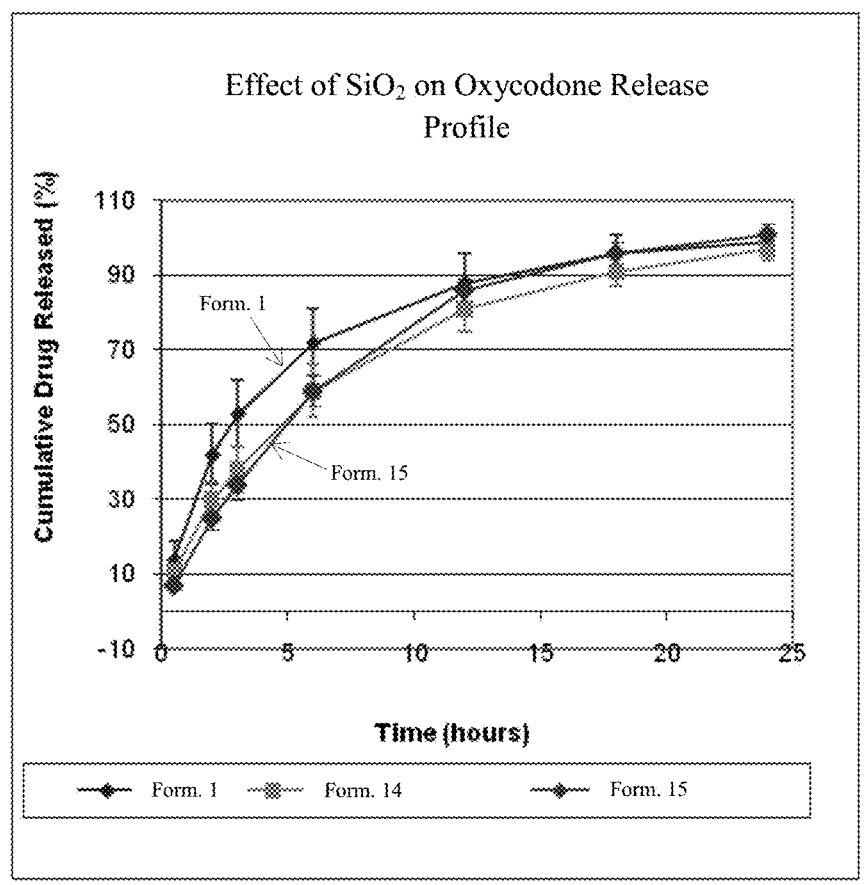
FIG. 9 is a graph showing the effect of $SiO_2$ on an oxycodone mean release profile. Results for Formulation 1, and Formulations 14 and 15 are shown.
Figure 10:
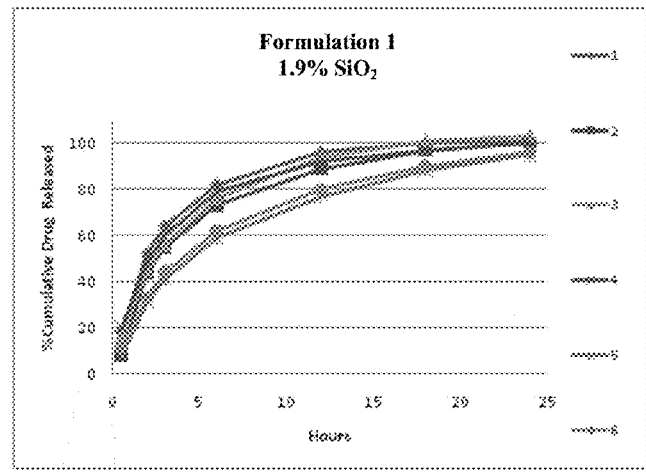
FIG. 10 provides graphs showing the effect of increased amounts of $SiO_2$ on inter-capsule variability during dissolution. Results for Formulation 1 (Panel A), and Formulations 14 (Panel B) and 15 (Panel C) are shown.
Figure 10:
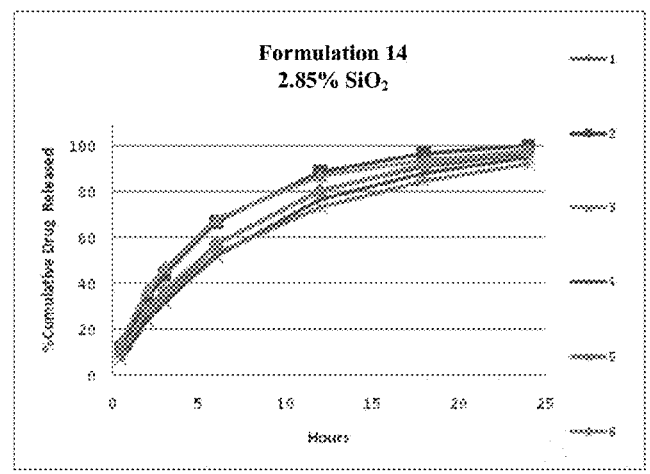
Figure 10:
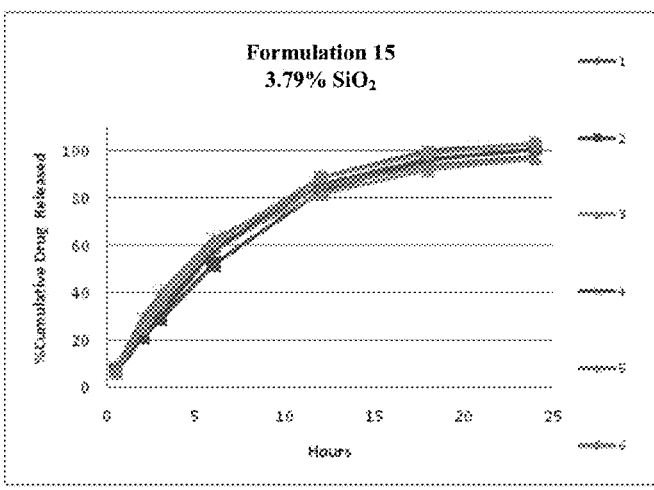

The results of the dissolution experiments are provided in FIG. 9; FIG. 10, Panels A-C; and Table 12 (below). The results demonstrate a) a reduction in the mean release prior to 12 hours with increasing $SiO_2$ concentration as shown in FIG. 9, and b) a reduction in the inter-capsule dissolution variability with increasing $SiO_2$ concentration as shown in FIG. 10, Panels A-C, and Table 12.

TABLE 12

| ID | $SiO_2$ (% w/w) | Sample No. | Time Point (hrs) | 0.5 | 2 | 3 | 6 | 12 | 18 | 24 | Sp* |
|---|---|---|---|---|---|---|---|---|---|---|---|
| Formulation 1 | 1.90 | 6 | Mean | 14 | 42 | 53 | 72 | 88 | 96 | 99 | 7 |
| | | | SD | 5 | 8 | 9 | 9 | 8 | 5 | 3 | |
| Formulation 14 | 2.85 | 6 | Mean | 11 | 30 | 38 | 59 | 81 | 91 | 97 | 5 |
| | | | SD | 3 | 5 | 6 | 7 | 6 | 4 | 3 | |
| Formulation 15 | 3.79 | 6 | Mean | 7 | 25 | 34 | 59 | 86 | 96 | 101 | 3 |
| | | | SD | 1 | 3 | 4 | 4 | 3 | 3 | 3 | |

*Sp as used herein = Pooled standard deviation which is calculated as provided below:

$$s_p = \left( \frac{(n_1 - 1)s_1^2 + (n_2 - 1)s_2^2 + \ldots (n_k - 1)s_k^2}{n_1 + n_2 + \ldots n_k - k} \right)^{1/2}$$

wherein, n=sample number and the suffixes 1, 2, . . . k refer to the different series of measurements.

Rheology Testing Results

Figure 11:
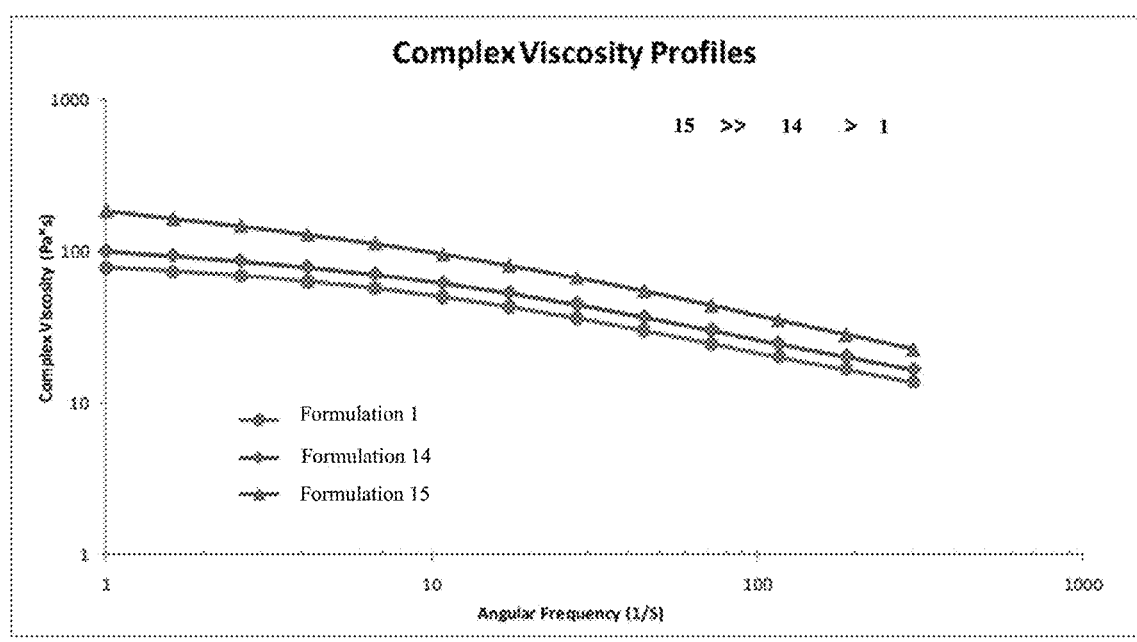
FIG. 11 is a graph showing the complex viscosity profiles for Formulations 1, 14 and 15. Increasing $SiO_2$ concentration above about 2% increases complex viscosity which may lead to decreasing reproducible deformation and therefore low inter-capsule variability during dissolution testing.

Table 13 (below) summarizes the results measured at angular frequency of 10 s$^{-1}$. Complex viscosity profiles with angular frequency sweep are shown in FIG. 11.

TABLE 13

| ID | SAIB (% w/w) | TA (% w/w) | IPM (% w/w) | $SiO_2$ (% w/w) | Complex Viscosity (Pa · s) | Storage Modulus (Pa) (G') | Loss Modulus (Pa) (G") | Damping Factor (G"/G') |
|---|---|---|---|---|---|---|---|---|
| Formulation 1 | 40.98 | 27.32 | 14.23 | 1.90 | 49.53 | 245.00 | 474.33 | 1.93 |
| Formulation 14 | 40.41 | 26.64 | 14.23 | 2.85 | 61.63 | 311.00 | 586.67 | 1.89 |
| Formulation 15 | 39.85 | 26.56 | 14.23 | 3.79 | 95.50 | 540.67 | 874.67 | 1.62 |

As shown, increasing $SiO_2$ concentration above about 2% increases complex viscosity which may lead to decreasing matrix deformation and therefore low inter-capsule variability during dissolution testing. In addition to increase of the Loss Modulus, it is surprising that the extent of increase of Storage Modulus (G') is even higher which results in lower damping factor (G"/G') for Formulations 14 and 15 as compared with Formulation 1 (Reference Formulation A without BHT in HPMC capsule). In other word, increasing of $SiO_2$ does not only increase viscosity but also increase elasticity. Without intending to be bound by any particular theory, a lower damping factor may indicate a more stable microstructure which may lead to more stable dissolution stability.

Abuse Deterrence Results

The % of oxycodone released from each composition at sampling time points 0.5, 1, and 3 hours as determined by reverse-phase HPLC is provided in Table 14 below.

TABLE 14

| ID | $SiO_2$ (%) | Sample # | | Time point (hrs) 0.5 | 1 | 3 |
|---|---|---|---|---|---|---|
| Formulation 1 | 1.9 | 4 | Mean | 22 | 29 | 46 |
| | | | SD | 3 | 3 | 5 |
| Formulation 14 | 2.85 | 4 | Mean | 18 | 25 | 41 |
| | | | SD | 3 | 4 | 5 |
| Formulation 15 | 3.79 | 4 | Mean | 17 | 23 | 36 |
| | | | SD | 3 | 4 | 7 |

As shown above, the % release of oxycodone decreased at each time point with increased $SiO_2$ concentration, suggesting an improvement in this abuse deterrence characteristic with increased $SiO_2$ in the tested range.

Example 10: One Month Stability Analysis of Extended Release Oxycodone Compositions (Formulations 14 and 15)

Materials and Methods

Formulation 1 (Reference Formulation A without BHT in HPMC capsule) and Formulations 14 and 15 were stored at 25° C./60% RH or 40° C./75% RH for a one-month period of time. Six capsules from each composition lot were tested according to the testing conditions discussed above to evaluate the effect on mean release and inter-capsule dissolution variability.

Results

Figure 12:
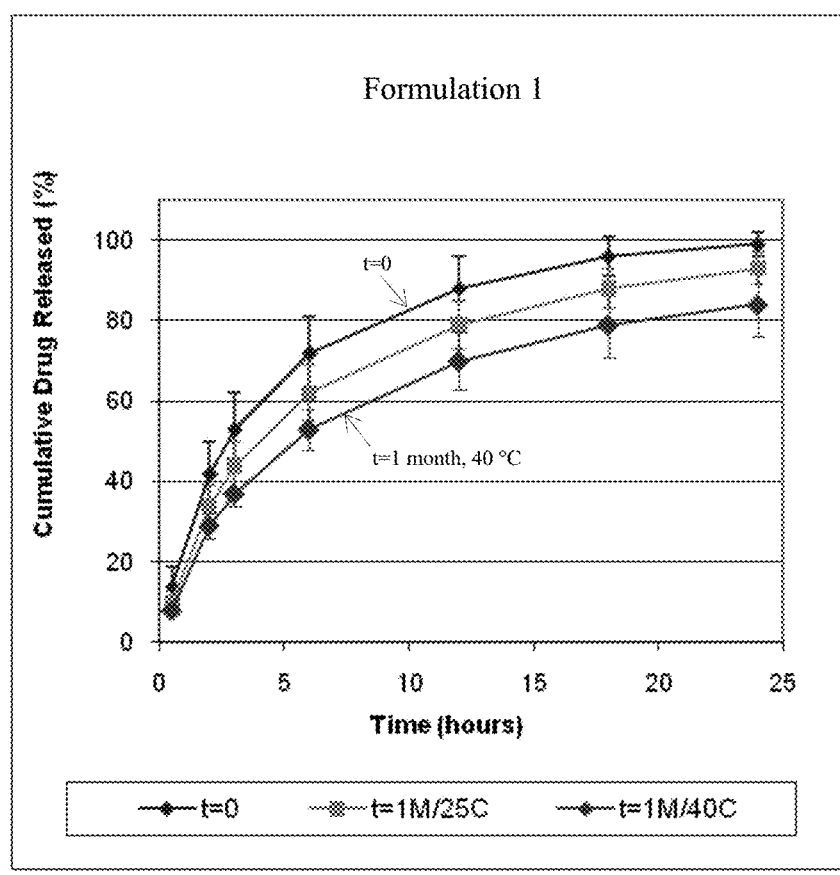
FIG. 12 is a graph showing mean release of oxycodone from Formulation 1 following storage for 1 month at 25° C. or 40° C.
Figure 13:
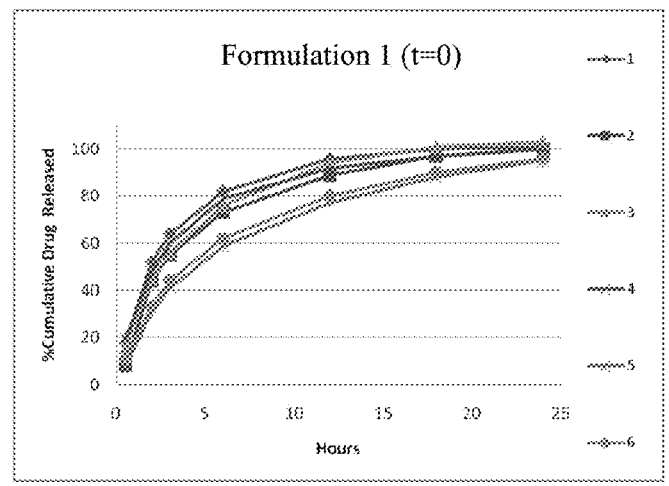
FIG. 13 provides graphs showing inter-capsule variability during dissolution testing of Formulation 1 following storage for 1 month at 25° C. or 40° C.
Figure 13:
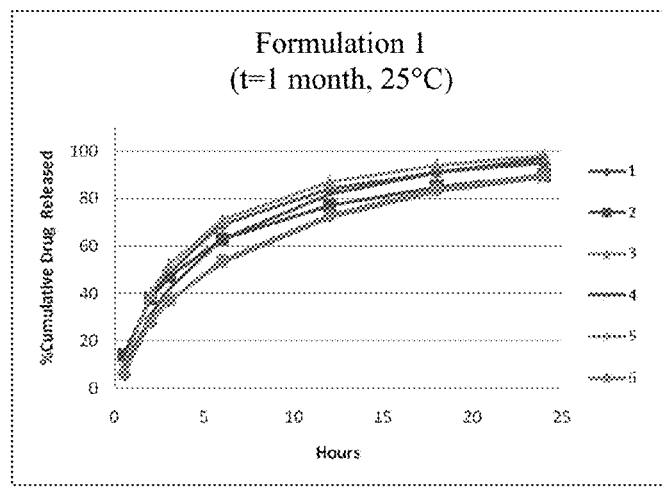
Figure 13:
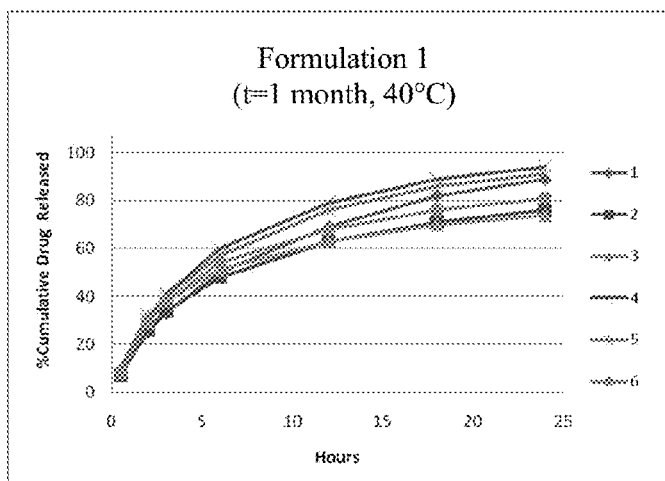

The results for Formulation 1 are provided in FIG. 12; FIG. 13, Panels A-C; and Table 15 below. Mean release is decreased for the stored Formulation 1 capsule samples relative to the T=0 samples as shown in FIG. 12. Inter-capsule variation was similar for the stored Formulation 1 samples and the T=0 samples as shown in FIG. 13, Panels A-C and Table 15.

TABLE 15

| ID | $SiO_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| Formulation 1 | 1.90 | 0 | NA | 6 | Mean | 14 | 42 | 53 | 72 | 88 | 96 | 99 | 7 |
| | | | | | SD | 5 | 8 | 9 | 9 | 8 | 5 | 3 | |
| | | 1 | 25° C./60% RH | 6 | Mean | 10 | 34 | 44 | 62 | 79 | 88 | 93 | 5 |
| | | | | | SD | 3 | 5 | 6 | 7 | 6 | 5 | 4 | |
| | | | 40° C./75% RH | 6 | Mean | 8 | 29 | 37 | 53 | 70 | 79 | 84 | 6 |
| | | | | | SD | 1 | 3 | 3 | 5 | 7 | 8 | 8 | |

Figure 14:
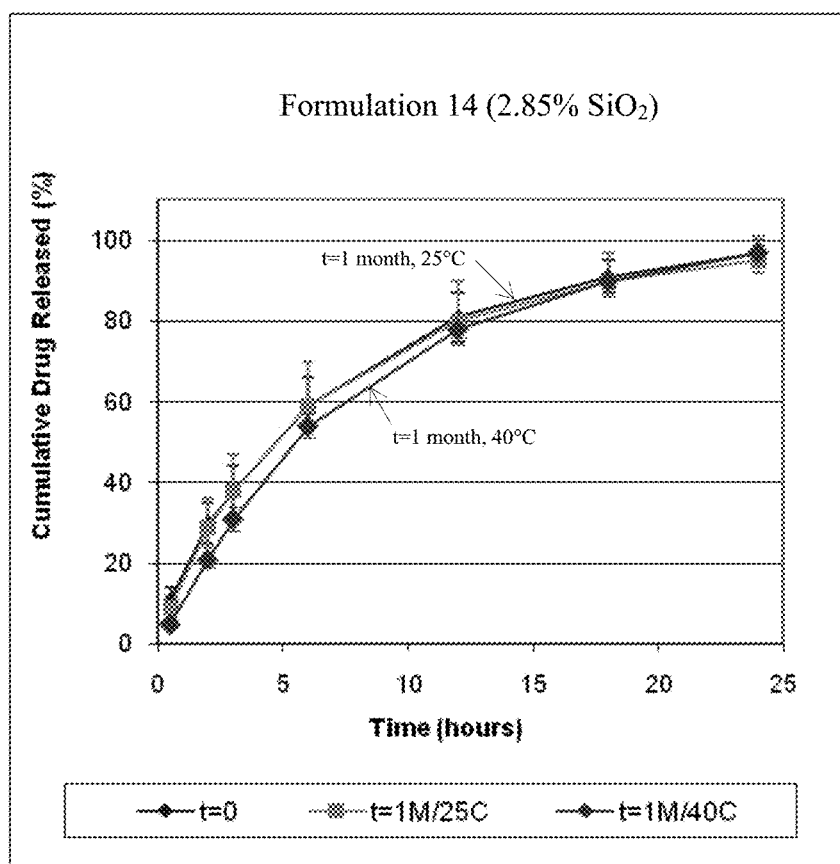
FIG. 14 is a graph showing mean release of oxycodone from Formulation 14 following storage for 1 month at 25° C. or 40° C.
Figure 15:
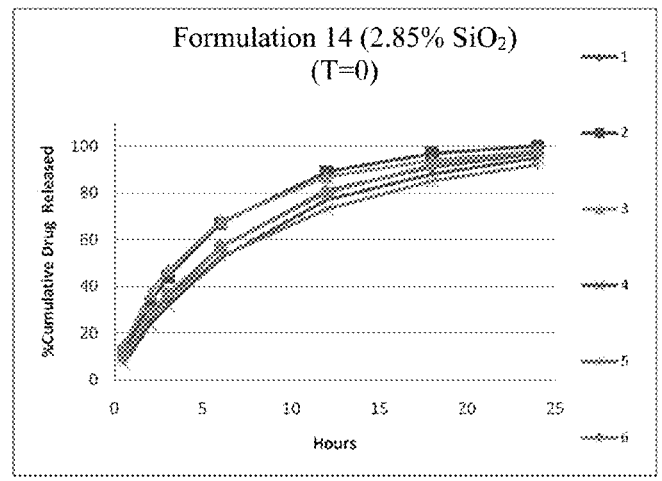
FIG. 15 provides graphs showing inter-capsule variability during dissolution testing of Formulation 14 following storage for 1 month at 25° C. or 40° C.
Figure 15:
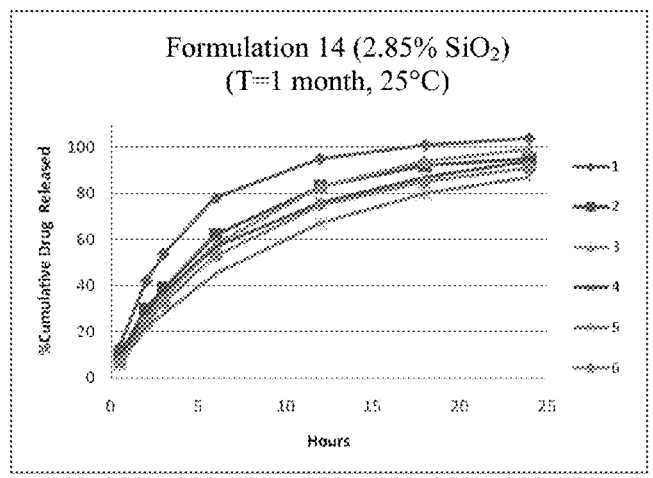
Figure 15:
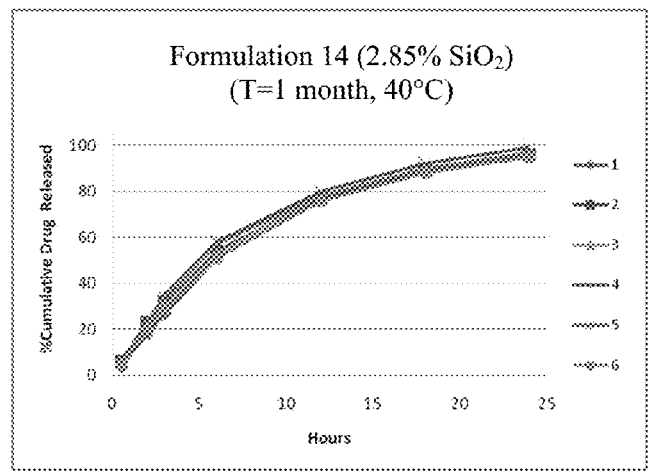

The results for Formulation 14 are provided in FIG. 14; FIG. 15, Panels A-C; and Table 16 below. Mean release is not significantly changed for the Formulation 14 samples relative to the T=0 samples as shown in FIG. 14. Sample variation was decreased for the Formulation 14 samples stored at 40° C./75% RH relative to the T=0 samples as shown in FIG. 15, Panels A-C and Table 16.

TABLE 16

| ID | $SiO_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| Formulation 14 | 2.85 | 0 | NA | 6 | Mean | 11 | 30 | 38 | 59 | 81 | 91 | 97 | 5 |
| | | | | | SD | 3 | 5 | 6 | 7 | 6 | 4 | 3 | |
| | | 1 | 25° C./60% RH | 6 | Mean | 9 | 29 | 38 | 59 | 80 | 90 | 95 | 8 |
| | | | | | SD | 3 | 7 | 9 | 11 | 10 | 7 | 6 | |
| | | | 40° C./75% RH | 6 | Mean | 5 | 21 | 31 | 54 | 78 | 90 | 97 | 2 |
| | | | | | SD | 1 | 2 | 3 | 3 | 2 | 2 | 2 | |

Figure 16:
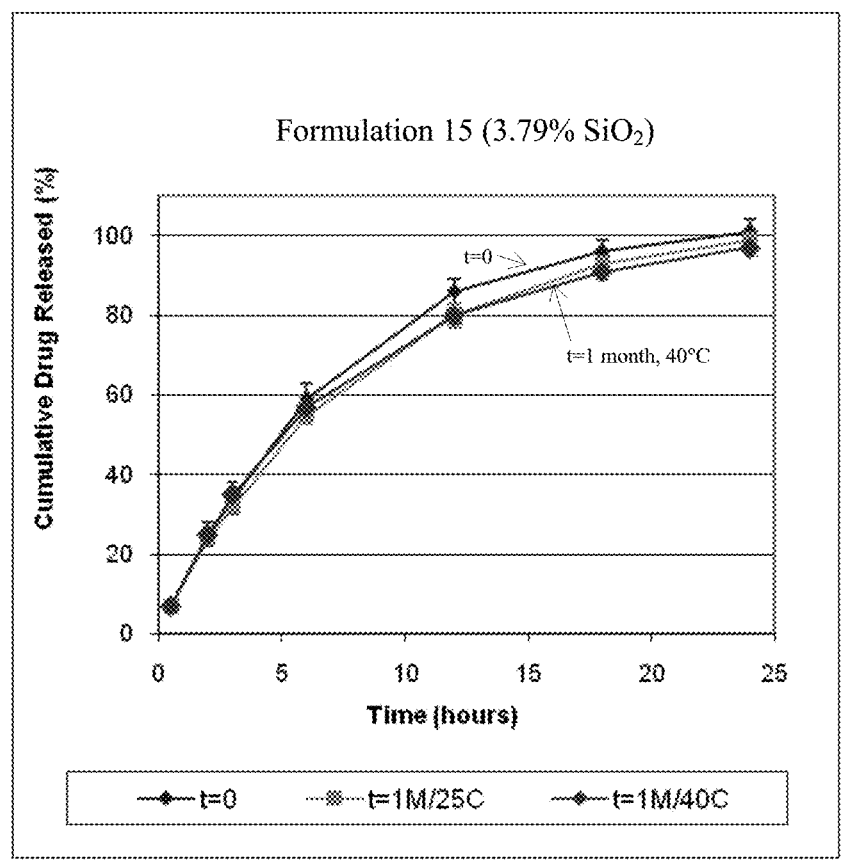
FIG. 16 is a graph showing mean release of oxycodone from Formulation 15 following storage for 1 month at 25° C. or 40° C.
Figure 17:
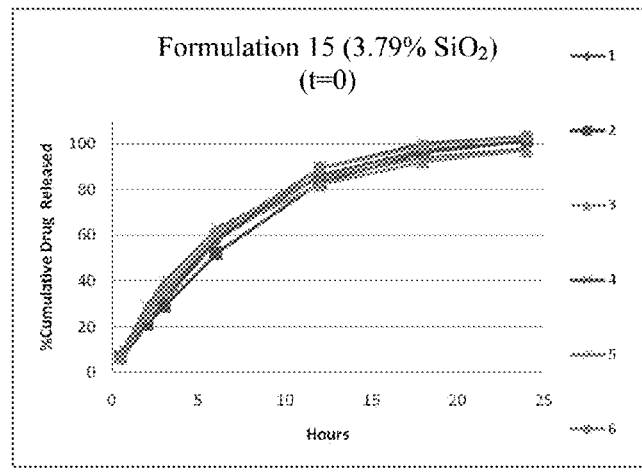
FIG. 17 provides graphs showing inter-capsule variability during dissolution testing of Formulation 15 following storage for 1 month at 25° C. or 40° C.
Figure 17:
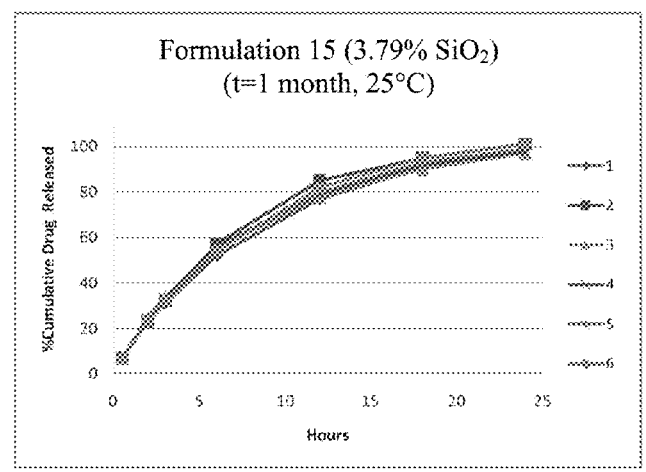
Figure 17:
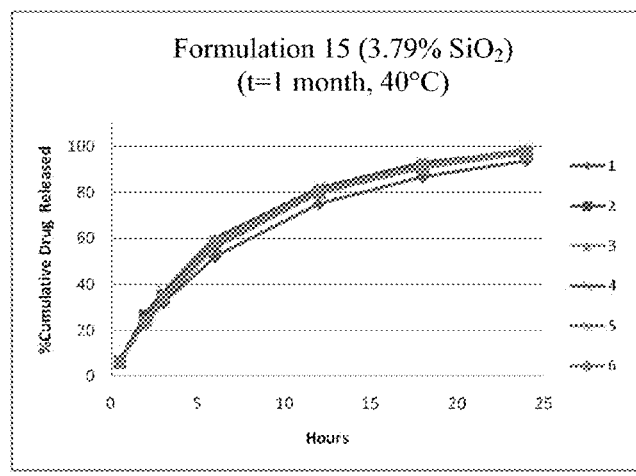

The results for Formulation 15 are provided in FIG. 16; FIG. 17, Panels A-C; and Table 17 below. Mean release is not significantly changed for the Formulation 15 relative to the T=0 samples as shown in FIG. 16. Sample variation was low and similar for the Formulation 15 samples stored at 25° C./60% RH and 40° C./75% RH relative to the T=0 samples as shown in FIG. 17, Panels A-C and Table 17.

TABLE 17

| ID | $SiO_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| Formulation 15 | 3.79 | 0 | NA | 6 | Mean | 7 | 25 | 34 | 59 | 86 | 96 | 101 | 3 |
| | | | | | SD | 1 | 3 | 4 | 4 | 3 | 3 | 3 | |
| | | 1 | 25° C./60% RH | 6 | Mean | 7 | 24 | 32 | 55 | 80 | 93 | 99 | 2 |
| | | | | | SD | 0 | 1 | 1 | 2 | 3 | 2 | 2 | |
| | | | 40° C./75% RH | 6 | Mean | 7 | 25 | 35 | 57 | 80 | 91 | 97 | 2 |
| | | | | | SD | 1 | 2 | 2 | 3 | 2 | 2 | 2 | |

Example 11: Preparation and Analysis of Extended Release Oxycodone Compositions (Formulations 16-18)

Still additional compositions (Formulations 16-18) were prepared and characterized with respect to inter-capsule dissolution variability and abuse deterrence characteristics as indicated below.

Materials and Methods

The compositions were prepared to provide the compositions indicated in Table 18 (below). Composition components were blended and individual compositions were encapsulated in HPMC capsules as described above.

TABLE 18

| Low-IPM Compositions | | | |
|---|---|---|---|
| Composition (% w/w) | Formulation 16 | Formulation 17 | Formulation 18 |
| SAIB | 42.93 | 42.42 | 41.92 |
| TA | 37.14 | 36.7 | 36.26 |
| IPM | 2.47 | 2.47 | 2.47 |
| CAB | 4.74 | 4.74 | 4.74 |
| HEC | 5.69 | 5.69 | 5.69 |
| Colloidal SiO$_2$ | 1.90 | 2.85 | 3.79 |
| Micronized oxycodone base | 5.13 | 5.13 | 5.13 |
| Capsule shell | HPMC | HPMC | HPMC |

Dissolution Testing

Six capsules from each composition lot were tested according to the testing conditions discussed above to evaluate the effect on inter-capsule dissolution variability.

Abuse Deterrence

Four capsules from each composition were tested for abuse deterrence characteristics. The release rate of oxycodone base was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5, 1, and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing

Figure 18:
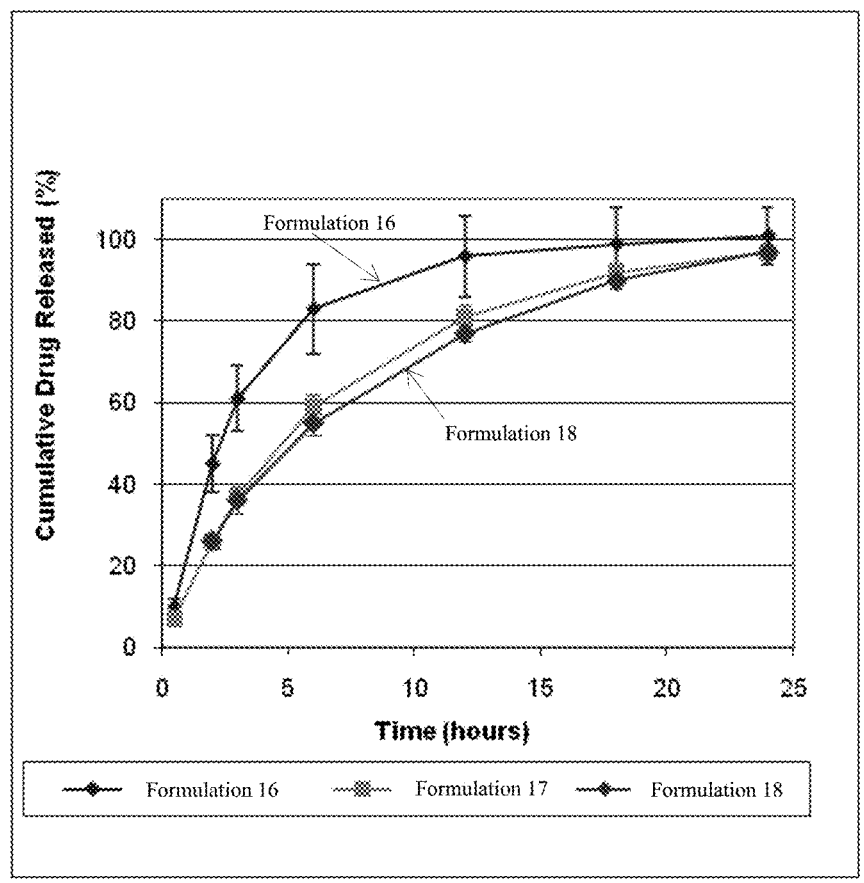
FIG. 18 is a graph showing mean release of oxycodone from Formulations 16, 17 and 18.
Figure 19:
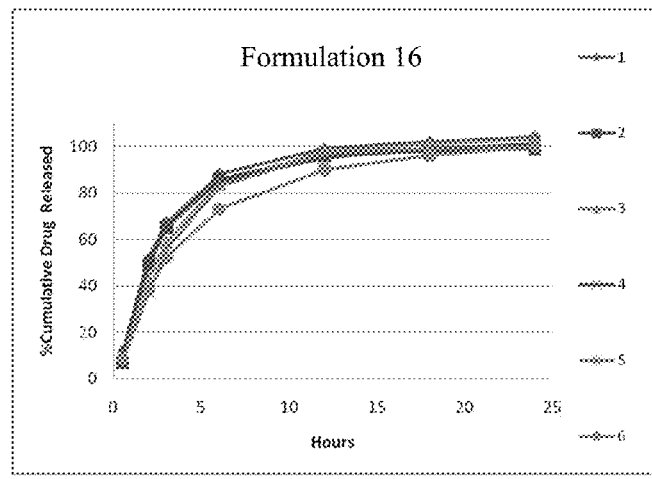
FIG. 19 provides graphs showing inter-capsule variability during dissolution testing of Formulation 16 (Panel A), Formulation 17 (Panel B) and Formulation 18 (Panel C).
Figure 19:
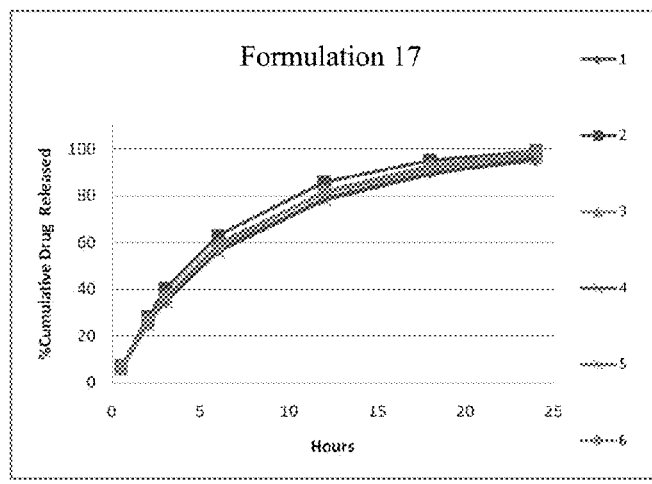
Figure 19:
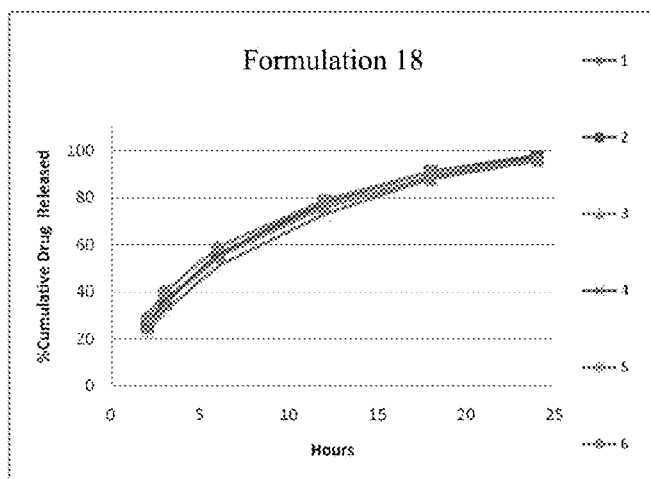

The results of the dissolution experiments are provided in FIG. 18; FIG. 19, Panels A-C; and Table 19 (below). The results demonstrate a) a reduction in the mean release with increasing SiO$_2$ concentration as shown in FIG. 18, and b) a reduction in the inter-capsule variability with increasing SiO$_2$ concentration as shown in FIG. 19, Panels A-C, and Table 19.

TABLE 19

| ID | SiO$_2$ (% w/w) | Sample No. | | Time Point (hrs) | | | | | | | |
|---|---|---|---|---|---|---|---|---|---|---|---|
| | | | | 0.5 | 2 | 3 | 6 | 12 | 18 | 24 | Sp |
| Formulation 16 | 1.90 | 6 | Mean | 10 | 45 | 61 | 83 | 96 | 99 | 101 | 4 |
| | | | SD | 2 | 7 | 6 | 5 | 3 | 2 | 2 | |
| Formulation 17 | 2.85 | 6 | Mean | 7 | 26 | 37 | 59 | 81 | 92 | 97 | 2 |
| | | | SD | 1 | 1 | 2 | 3 | 3 | 2 | 2 | |
| Formulation 18 | 3.79 | 6 | Mean | N/A | 26 | 36 | 55 | 77 | 90 | 97 | 2 |
| | | | SD | N/A | 2 | 3 | 3 | 2 | 2 | 1 | |

Abuse Deterrence

The % of oxycodone released from each composition at sampling time points 0.5, 1, and 3 hours as determined by reverse-phase HPLC is provided in Table 20 below.

TABLE 20

| ID | SiO$_2$ (%) | Sample # | | Time point (hrs) | | |
|---|---|---|---|---|---|---|
| | | | | 0.5 | 1 | 3 |
| Formulation 16 | 1.9 | 4 | Mean | 26 | 35 | 60 |
| | | | SD | 5 | 6 | 8 |
| Formulation 17 | 2.85 | 4 | Mean | 28 | 40 | 64 |
| | | | SD | 3 | 3 | 3 |
| Formulation 18 | 3.79 | 4 | Mean | 14 | 22 | 40 |
| | | | SD | 2 | 3 | 4 |

As shown above, the % release of oxycodone was decreased for the 3.79% $SiO_2$ composition relative to the 1.9% and 2.85% $SiO_2$ compositions, suggesting an improvement in this abuse deterrence characteristic at 3.79% $SiO_2$ relative to the 1.9% and 2.85% $SiO_2$.

Example 12: One Month Stability Analysis of Extended Release Oxycodone Compositions (Formulations 16-18)

Materials and Methods

Formulations 16, 17 and 18 were stored at 25° C./60% RH or 40° C./75% RH for a one-month period of time. Six capsules from each composition lot were tested according to the testing conditions discussed above to evaluate the effect on mean release and inter-capsule dissolution variability.

Results

Figure 20:
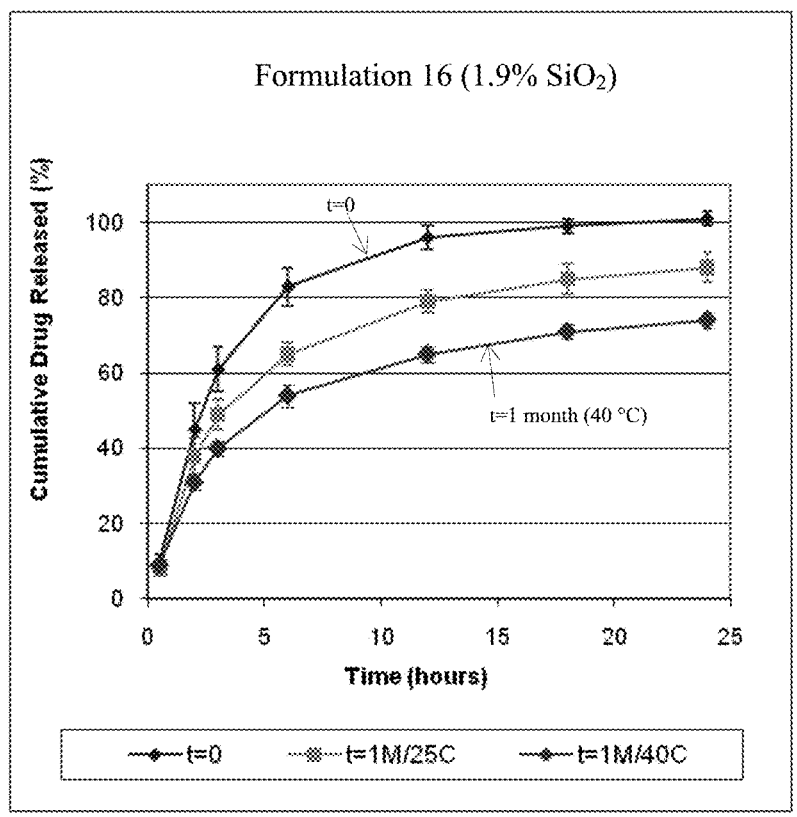
FIG. 20 is a graph showing mean release of oxycodone from Formulation 16 following storage for 1 month at 25° C. or 40° C.
Figure 21:
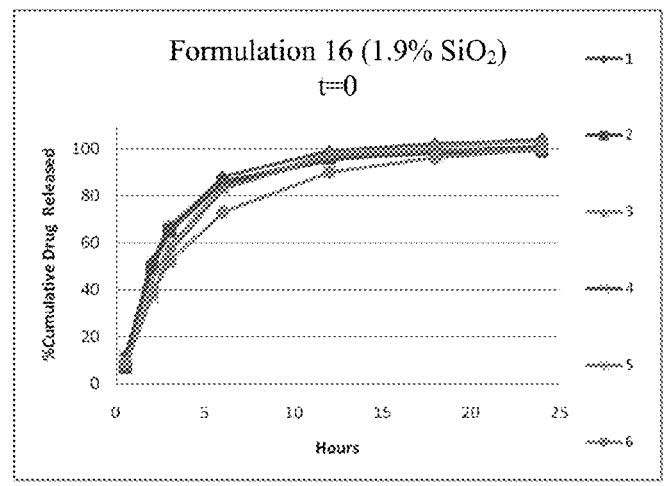
FIG. 21 provides graphs showing inter-capsule variability during dissolution testing of Formulation 16 following storage for 1 month at 25° C. or 40° C.
Figure 21:
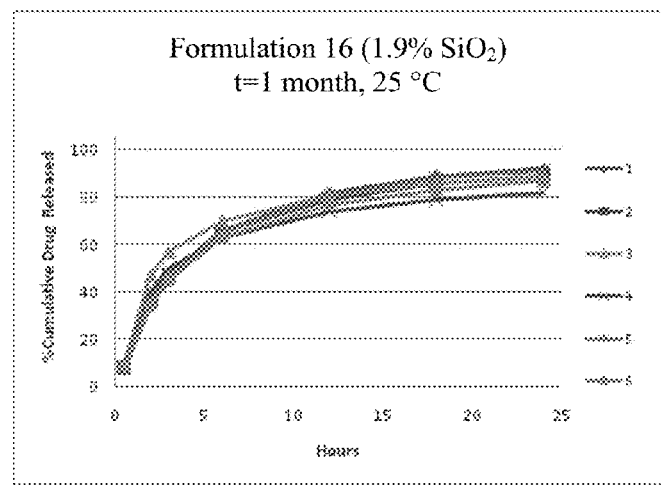
Figure 21:
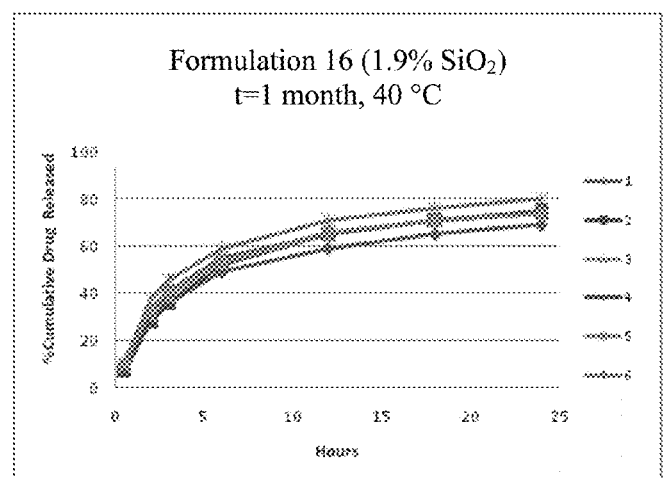

The results for Formulation 16 are provided in FIG. 20; FIG. 21, Panels A-C; and Table 21 below. Mean release decreased with increasing storage temperature for the stored Formulation 16 samples relative to the T=0 samples as shown in FIG. 20. Inter-capsule variation was similar for the stored Formulation 16 samples and the T=0 samples as shown in FIG. 21, Panels A-C and Table 21.

TABLE 21

| ID | $SiO_2$ (% w/w) | Time Point (Months) | Storage Condition | Sample No. | | Time Point (hrs) | | | | | | | Sp |
|---|---|---|---|---|---|---|---|---|---|---|---|---|---|
| | | | | | | 0.5 | 2 | 3 | 6 | 12 | 18 | 24 | |
| Formulation 16 | 1.90 | 0 | NA | 6 | Mean | 10 | 45 | 61 | 83 | 96 | 99 | 101 | 4 |
| | | | | | SD | 2 | 7 | 6 | 5 | 3 | 2 | 2 | |
| | | 1 | 25° C./60% RH | 6 | Mean | 8 | 38 | 49 | 65 | 79 | 85 | 88 | 4 |
| | | | | | SD | 1 | 5 | 4 | 3 | 3 | 4 | 4 | |
| | | | 40° C./75% RH | 6 | Mean | 9 | 31 | 40 | 54 | 65 | 71 | 74 | 3 |
| | | | | | SD | 2 | 3 | 4 | 3 | 4 | 3 | 4 | |

Figure 22:
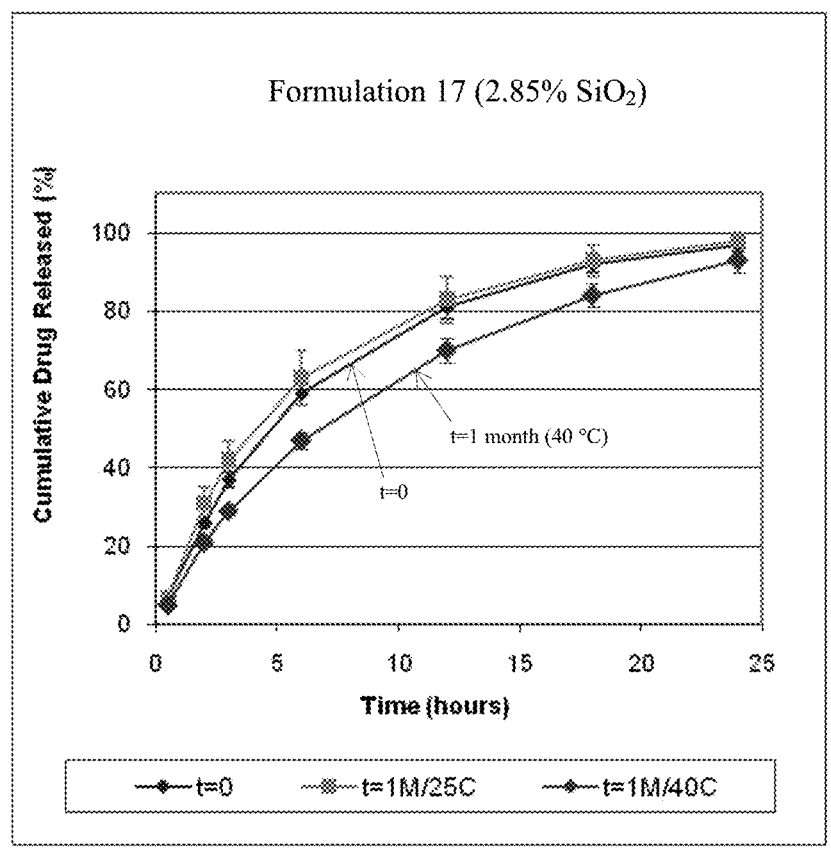
FIG. 22 is a graph showing mean release of oxycodone from Formulation 17 following storage for 1 month at 25° C. or 40° C.
Figure 23:
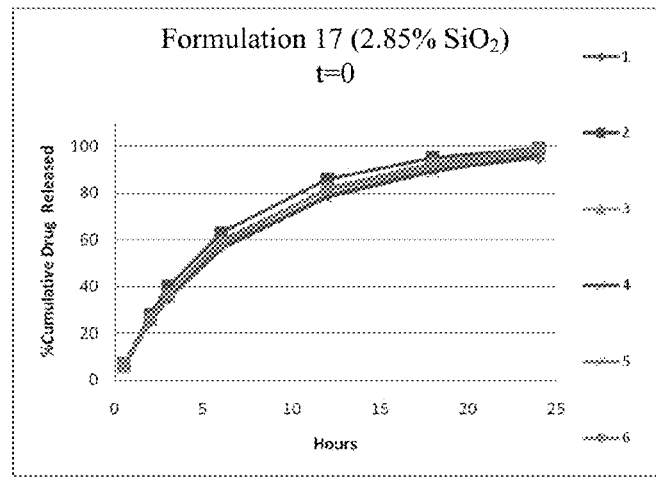
FIG. 23 provides graphs showing inter-capsule variability during dissolution testing of Formulation 17 following storage for 1 month at 25° C. or 40° C.
Figure 23:
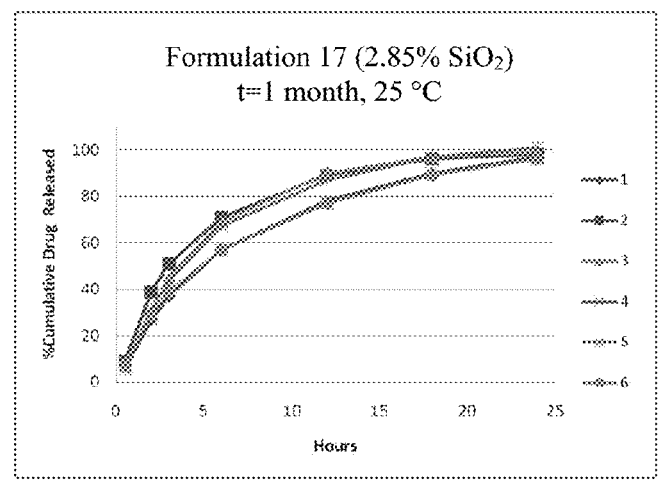
Figure 23:
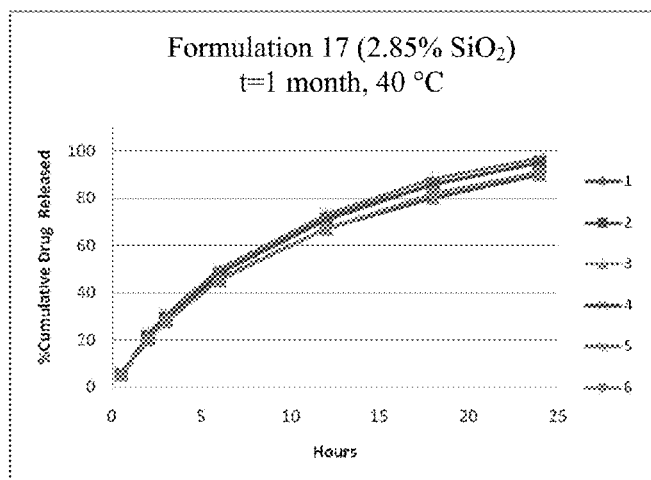

The results for Formulation 17 are provided in FIG. 22; FIG. 23, Panels A-C; and Table 22 below. Mean release is decreased for the Formulation 17 samples stored at 40° C./75% RH relative to the T=0 samples as shown in FIG. 22. Sample variation was increased for the Formulation 17 samples stored at 25° C./60% RH relative to the T=0 samples as shown in FIG. 23, Panels A-C and Table 22.

TABLE 22

| ID | $SiO_2$ (% w/w) | Time Point (Months) | Storage Condition | Sample No. | | Time Point (hrs) | | | | | | | Sp |
|---|---|---|---|---|---|---|---|---|---|---|---|---|---|
| | | | | | | 0.5 | 2 | 3 | 6 | 12 | 18 | 24 | |
| Formulation 17 | 3 | 0 | NA | 6 | Mean | 7 | 26 | 37 | 59 | 81 | 92 | 97 | 2 |
| | | | | | SD | 1 | 1 | 2 | 3 | 3 | 2 | 2 | |
| | | 1 | 25° C./60% RH | 6 | Mean | 7 | 31 | 42 | 63 | 83 | 93 | 98 | 5 |
| | | | | | SD | 1 | 4 | 5 | 7 | 6 | 4 | 2 | |
| | | | 40° C./75% RH | 6 | Mean | 5 | 21 | 29 | 47 | 70 | 84 | 93 | 2 |
| | | | | | SD | 0 | 1 | 1 | 2 | 3 | 3 | 3 | |

Figure 24:
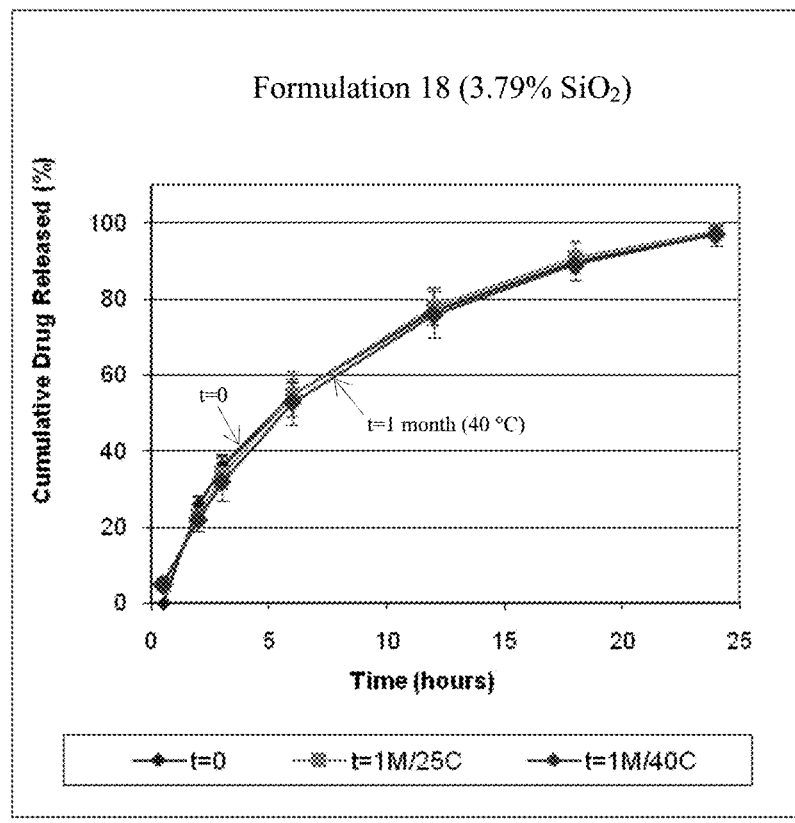
FIG. 24 is a graph showing mean release of oxycodone from Formulation 18 following storage for 1 month at 25° C. or 40° C.
Figure 25:
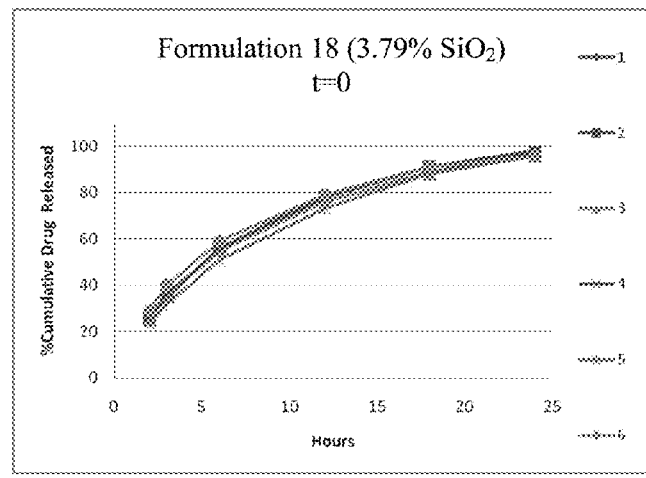
FIG. 25 provides graphs showing inter-capsule variability during dissolution testing of Formulation 18 following storage for 1 month at 25° C. or 40° C.
Figure 25:
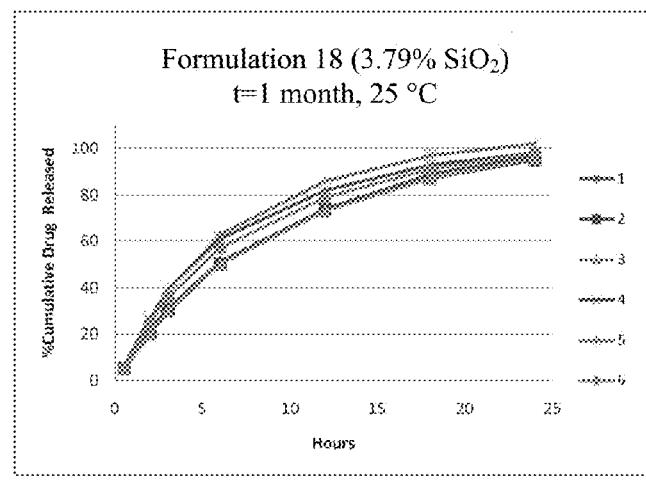
Figure 25:
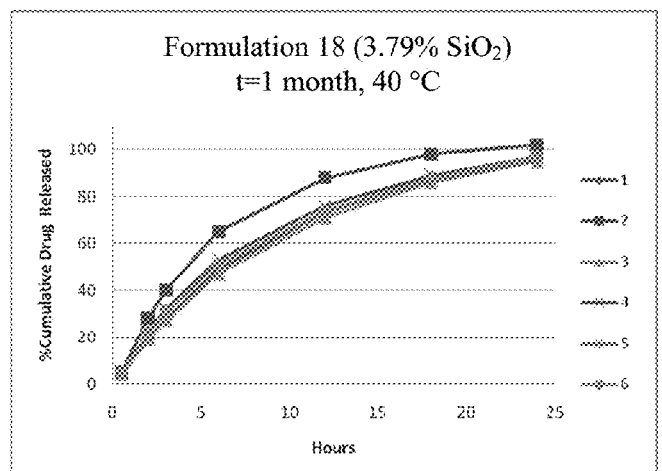

The results for Formulation 18 are provided in FIG. 24; FIG. 25, Panels A-C; and Table 23 below. Mean release is similar for the stored Formulation 18 samples relative to the T=0 samples as shown in FIG. 24. Sample variation was similar for the stored Formulation 18 samples as shown in FIG. 25, Panels A-C and Table 23.

TABLE 23

| ID | $SiO_2$ (% w/w) | Time Point (Months) | Storage Condition | Sample No. | | Time Point (hrs) | | | | | | | Sp |
|---|---|---|---|---|---|---|---|---|---|---|---|---|---|
| | | | | | | 0.5 | 2 | 3 | 6 | 12 | 18 | 24 | |
| Formulation 18 | 3.79 | 0 | NA | 6 | Mean | N/A | 26 | 36 | 55 | 77 | 90 | 97 | 2 |
| | | | | | SD | N/A | 2 | 3 | 3 | 2 | 2 | 1 | |
| | | | 25° C./60% RH | 6 | Mean | 5 | 23 | 34 | 55 | 78 | 91 | 98 | 4 |
| | | | | | SD | 0 | 3 | 4 | 6 | 5 | 4 | 2 | |
| | | | 40° C./75% RH | 6 | Mean | 5 | 22 | 32 | 53 | 76 | 89 | 97 | 4 |
| | | | | | SD | 0 | 3 | 5 | 6 | 6 | 4 | 3 | |

Example 13: Preparation and Analysis of Extended Release Oxycodone Compositions (Formulations 5, 7, 9, 19 and 20)

Formulations 5, 7, 9, and additional compositions (Formulations 19 and 20) were prepared and characterized with respect to inter-capsule dissolution variability and rheology as indicated below.

Materials and Methods

The compositions were prepared to provide the compositions indicated in Table 24 (below). Bulk compositions for Formulations 5 and 7 were mixed to make Formulations 9, 19 and 20. Individual compositions were encapsulated generally as described above for Example 8, with the exception that HPMC capsules were used in place of gelatin capsules.

TABLE 24

| Composition (% w/w) | Formulation 5 | Formulation 19 | Formulation 9 | Formulation 20 | Formulation 7 |
|---|---|---|---|---|---|
| Triacetin (TA) | 39.08 | 39.08 | 39.08 | 39.08 | 39.08 |
| Isopropyl myristate (IPM) | 2.48 | 2.48 | 2.48 | 2.48 | 2.48 |
| Sucrose Acetate Isobutyrate (SAIB) | 40.98 | 40.48 | 39.98 | 39.48 | 38.98 |
| Hydroxyethyl cellulose (HEC) | 5.69 | 5.69 | 5.69 | 5.69 | 5.69 |
| Cellulose acetate butyrate (CAB) | 4.74 | 4.74 | 4.74 | 4.74 | 4.74 |
| Colloidal silicon dioxide (Cab-o-sil) | 1.90 | 2.40 | 2.90 | 3.40 | 3.90 |
| Oxycodone | 5.13 | 5.13 | 5.13 | 5.13 | 5.13 |

Dissolution Testing

Twelve capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12, 18 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Rheology Testing

Samples of the above compositions were analyzed for rheological properties using an Anton Paar MCR301 Rheometer equipped with a parallel plate (25 mm diameter) and a gap setting of 1 mm. The samples were exposed to increasing temperature (20° C. to 80° C.) (at 2° C./min) at constant (0.5%) strain (oscillation mode) and 1 Hz frequency. Rheological properties for these compositions were compared with those of Reference Formulation A and Reference Formulation B, where the vehicle composition of Reference Formulation B was as follows: SAM (39.98% w/w), Triacetin (29.62% w/w), IPM (16.00% w/w), CAB 380-20BP (5.50% w/w), HEC (5.00 w/w), Cab-O-Sil (2.40% w/w), and Gelucire 44/14 (1.50% w/w).

Results

Dissolution Testing Results

Figure 26:
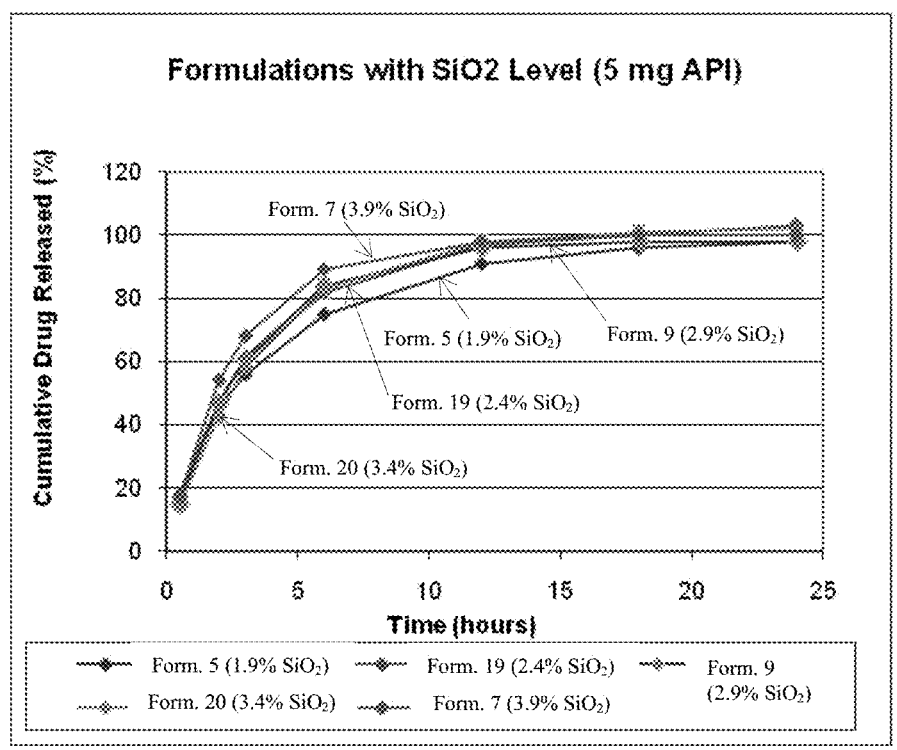
FIG. 26 is a graph showing mean release of oxycodone from Formulations 5, 7, 9, 19 and 20, with varying levels of $SiO_2$ and 5 mg oxycodone.
Figure 27:
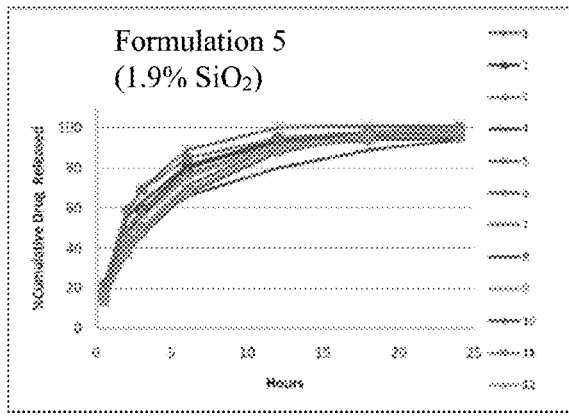
FIG. 27 provides graphs showing inter-capsule variability during dissolution testing of Formulations 5 (Panel A), 7 (Panel E), 9 (Panel C), 19 (Panel B) and 20 (Panel D), with varying levels of $SiO_2$ and 5 mg oxycodone.
Figure 27:
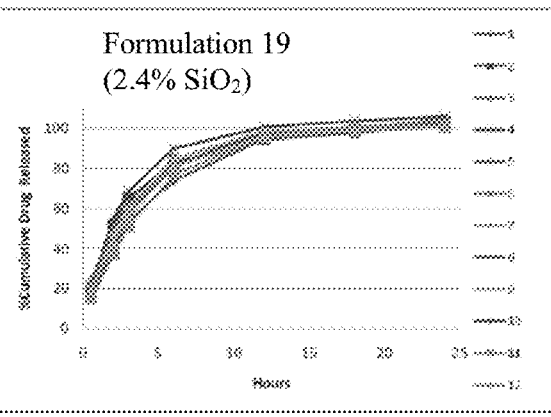
Figure 27:
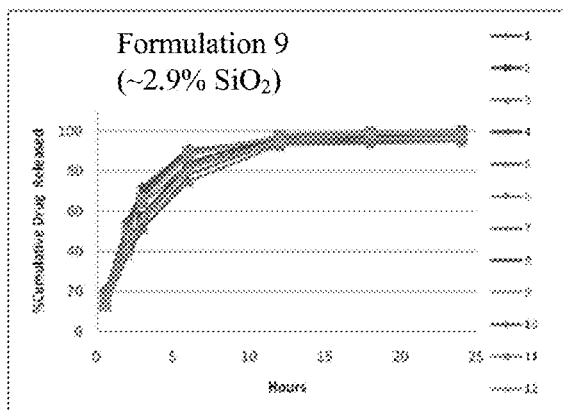
Figure 27:
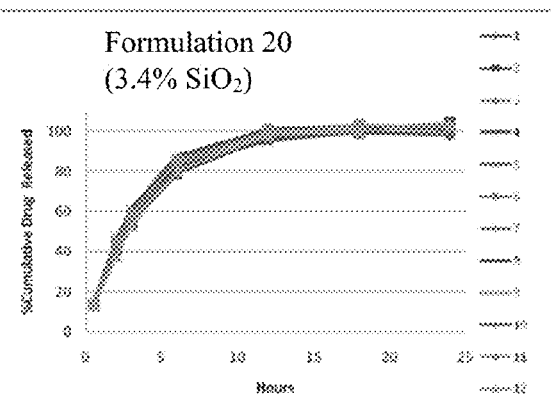
Figure 27:
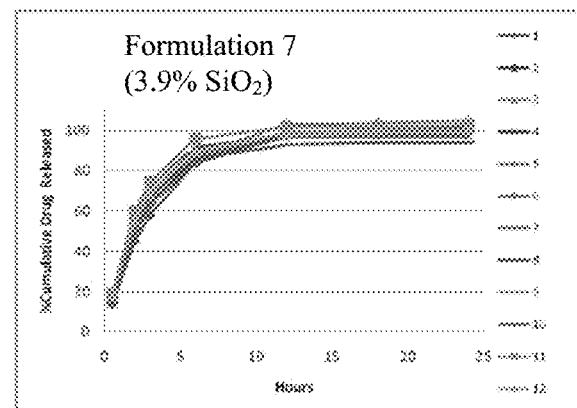

The results of the dissolution experiments for the 5 mg oxycodone compositions are shown in FIG. 26; FIG. 27, Panels A-E; and Table 25 below. The in vitro dissolution results indicate an increase in mean release at earlier time points with an increase in the concentration level of $SiO_2$ in the composition (FIG. 26). Formulations 19, 9, 20 and 7, with 2.4%, 2.9%, 3.4% and 3.9% $SiO_2$ respectively, showed decreased sample variability relative to Formulation 5 (1.9% $SiO_2$), with Formulation 20 (3.4% $SiO_2$) showing the least amount of sample variability (FIG. 27, Panels A-E).

TABLE 25

| ID | $SiO_2$ (% w/w) | Sample No. | | Time Point (hrs) | | | | | | | |
|---|---|---|---|---|---|---|---|---|---|---|---|
| | | | | 0.5 | 2 | 3 | 6 | 12 | 18 | 24 | Sp |
| Formulation 5 | 1.9 | 12 | Mean | 17 | 46 | 56 | 75 | 91 | 96 | 98 | 5 |
| | | | SD | 3 | 7 | 8 | 7 | 5 | 3 | 2 | |
| Formulation 19 | 2.4 | 12 | Mean | 18 | 47 | 60 | 82 | 97 | 100 | 103 | 3 |
| | | | SD | 3 | 5 | 5 | 4 | 2 | 1 | 1 | |
| Formulation 9 | 2.9 | 12 | Mean | 15 | 47 | 61 | 84 | 96 | 98 | 98 | 4 |
| | | | SD | 2 | 6 | 7 | 5 | 2 | 2 | 2 | |
| Formulation 20 | 3.4 | 12 | Mean | 14 | 43 | 58 | 83 | 98 | 101 | 102 | 2 |
| | | | SD | 1 | 3 | 3 | 3 | 2 | 2 | 2 | |
| Formulation 7 | 3.9 | 12 | Mean | 17 | 54 | 68 | 89 | 98 | 100 | 100 | 4 |
| | | | SD | 2 | 5 | 5 | 3 | 3 | 3 | 3 | |

Figure 28:
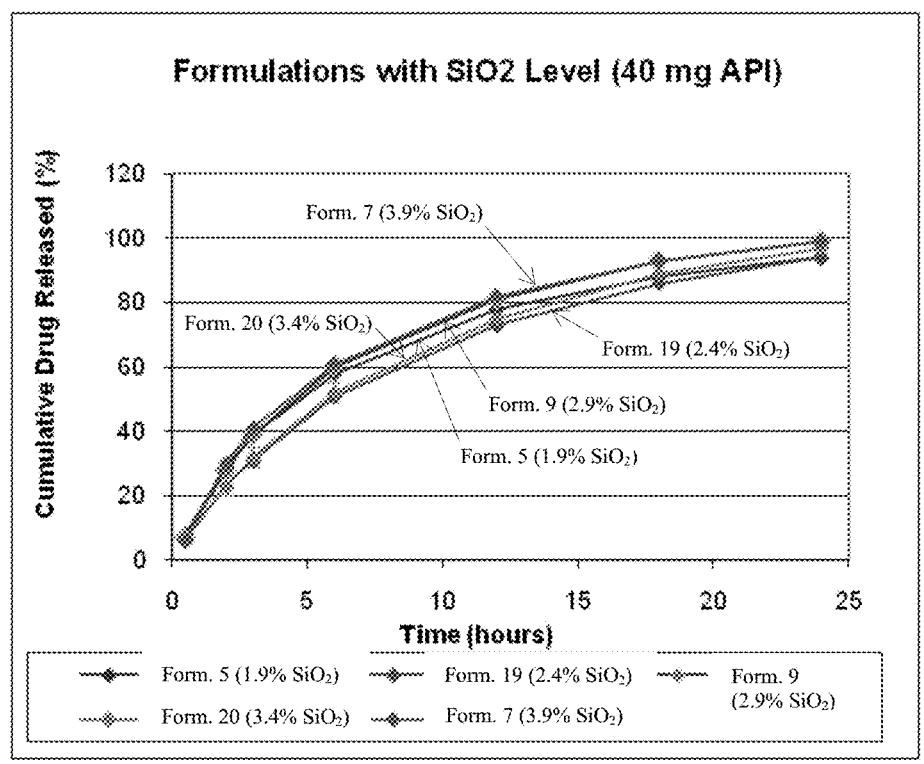
FIG. 28 is a graph showing mean release of oxycodone from Formulations 5, 7, 9, 19 and 20, with varying levels of $SiO_2$ and 40 mg oxycodone.
Figure 29:
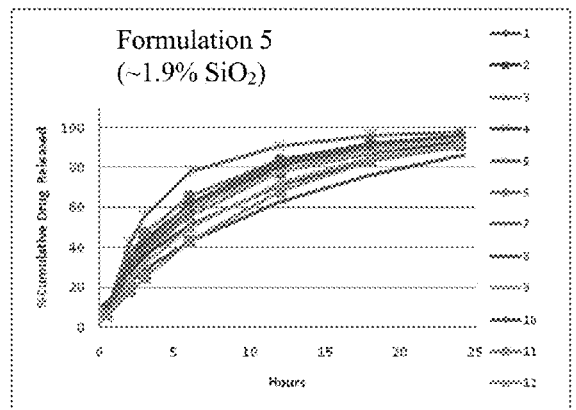
FIG. 29 provides graphs showing inter-capsule variability during dissolution testing of Formulations 5 (Panel A), 7 (Panel E), 9 (Panel C), 19 (Panel B) and 20 (Panel D), with varying levels of $SiO_2$ and 40 mg oxycodone.
Figure 29:
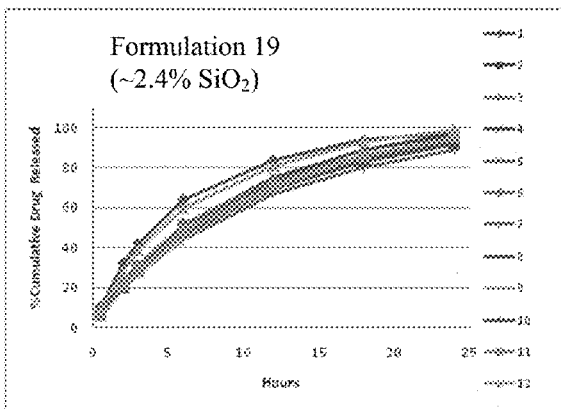
Figure 29:
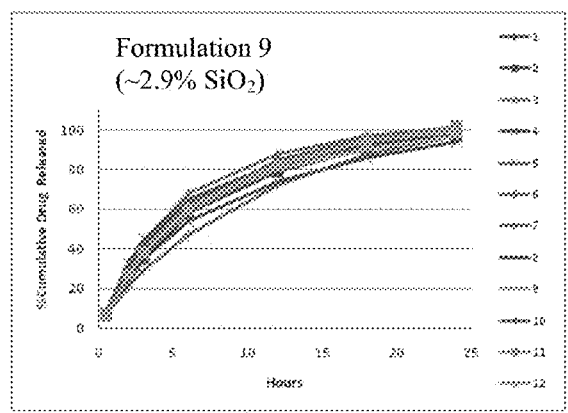
Figure 29:
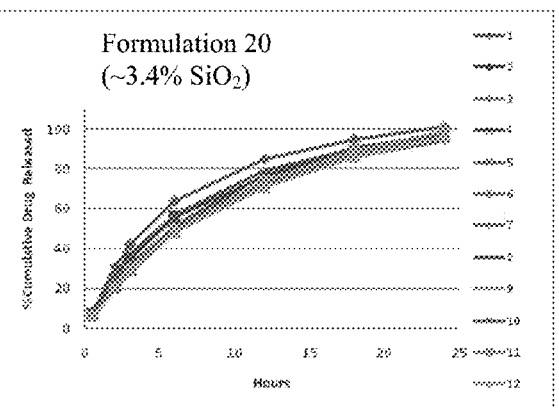
Figure 29:
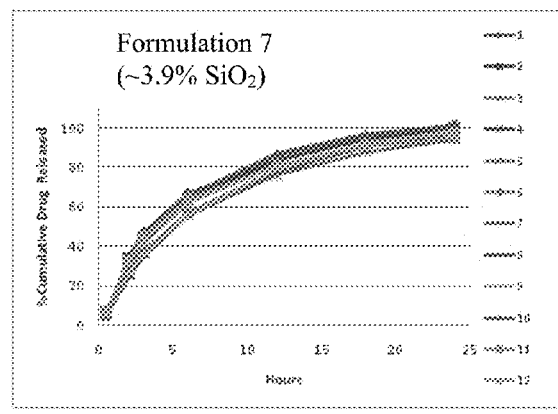

The results of the dissolution experiments for the 40 mg oxycodone compositions are shown in FIG. 28; FIG. 29, Panels A-E; and Table 26 below. The in vitro dissolution results showed a decrease in sample variability with increasing $SiO_2$ concentration (FIG. 29, Panels A-E).

TABLE 26

| ID | $SiO_2$ (%) | Sample No. | | Time Point (hrs) | | | | | | | |
|---|---|---|---|---|---|---|---|---|---|---|---|
| | | | | 0.5 | 2 | 3 | 6 | 12 | 18 | 24 | Sp |
| Formulation 5 | 1.9 | 12 | Mean | 8 | 29 | 39 | 58 | 78 | 88 | 94 | 7 |
| | | | SD | 2 | 7 | 8 | 10 | 8 | 5 | 3 | |
| Formulation 19 | 2.4 | 12 | Mean | 7 | 23 | 31 | 51 | 73 | 86 | 94 | 4 |
| | | | SD | 1 | 4 | 5 | 6 | 5 | 4 | 3 | |

TABLE 26-continued

| ID | SiO₂ (%) | Sample No. | | 0.5 | 2 | 3 | 6 | 12 | 18 | 24 | Sp |
|---|---|---|---|---|---|---|---|---|---|---|---|
| Formulation 9 | 2.9 | 12 | Mean | 7 | 28 | 39 | 60 | 81 | 93 | 99 | 4 |
| | | | SD | 1 | 3 | 4 | 5 | 5 | 3 | 2 | |
| Formulation 20 | 3.4 | 12 | Mean | 6 | 23 | 32 | 52 | 75 | 89 | 97 | 3 |
| | | | SD | 1 | 3 | 4 | 5 | 4 | 3 | 2 | |
| Formulation 7 | 3.9 | 12 | Mean | 6 | 30 | 41 | 61 | 82 | 93 | 99 | 3 |
| | | | SD | 1 | 3 | 4 | 4 | 3 | 3 | 2 | |

Rheology Testing Results

Figure 30:
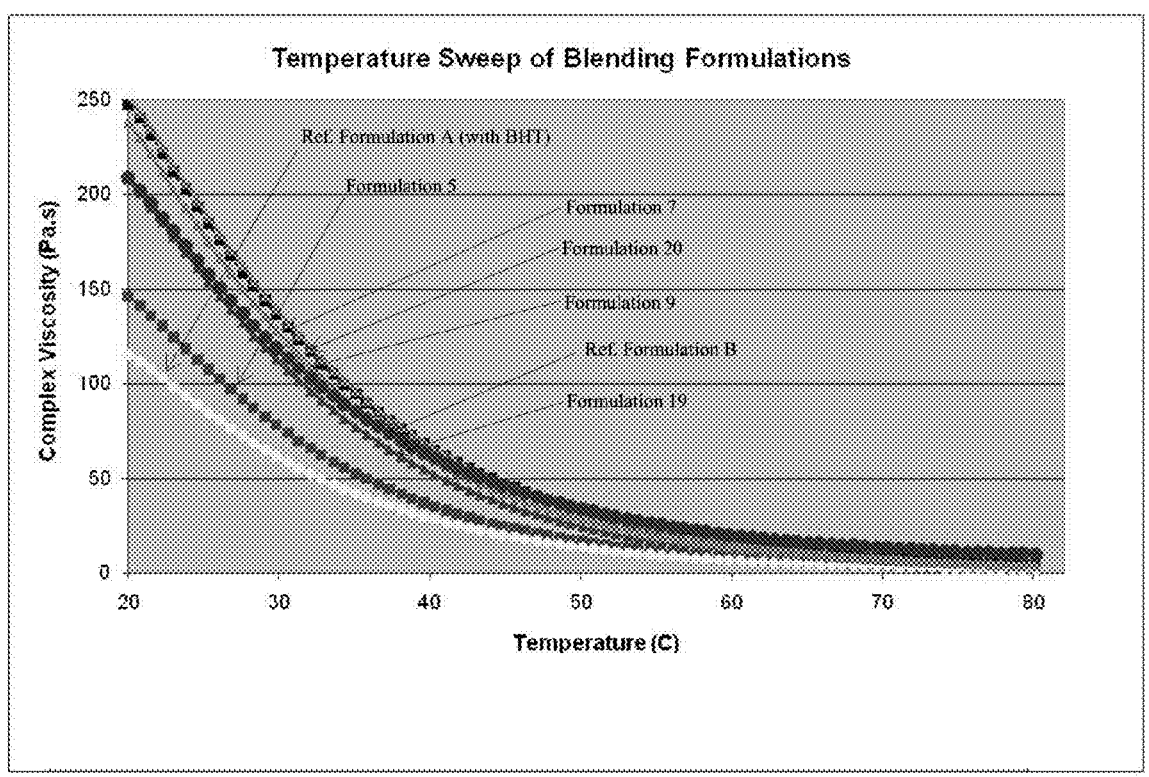
FIG. 30 is a graph showing complex viscosity as a function of temperature for Reference Formulation A and Formulations 5, 7, 9, 19 and 20.
Figure 31:
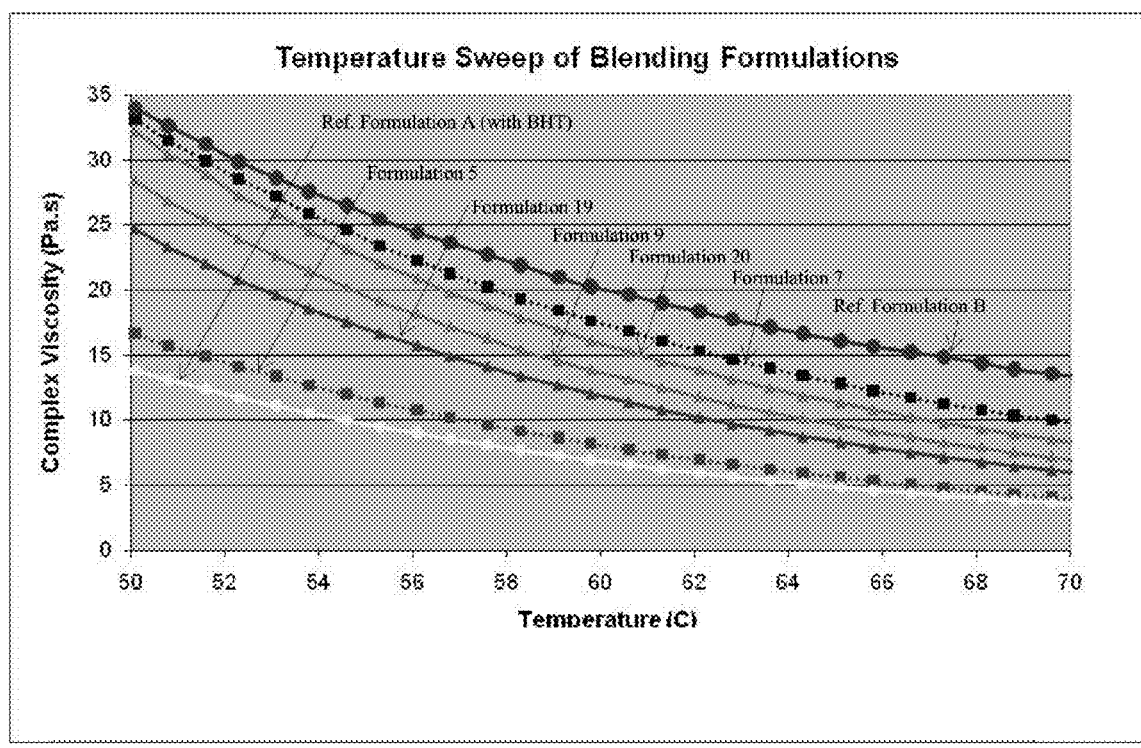
FIG. 31 is another graph showing complex viscosity as a function of temperature for Reference Formulation A and Formulations 5, 7, 9, 19 and 20. The graph in FIG. 31 provides a different temperature scale than that for FIG. 30.
Figure 32:
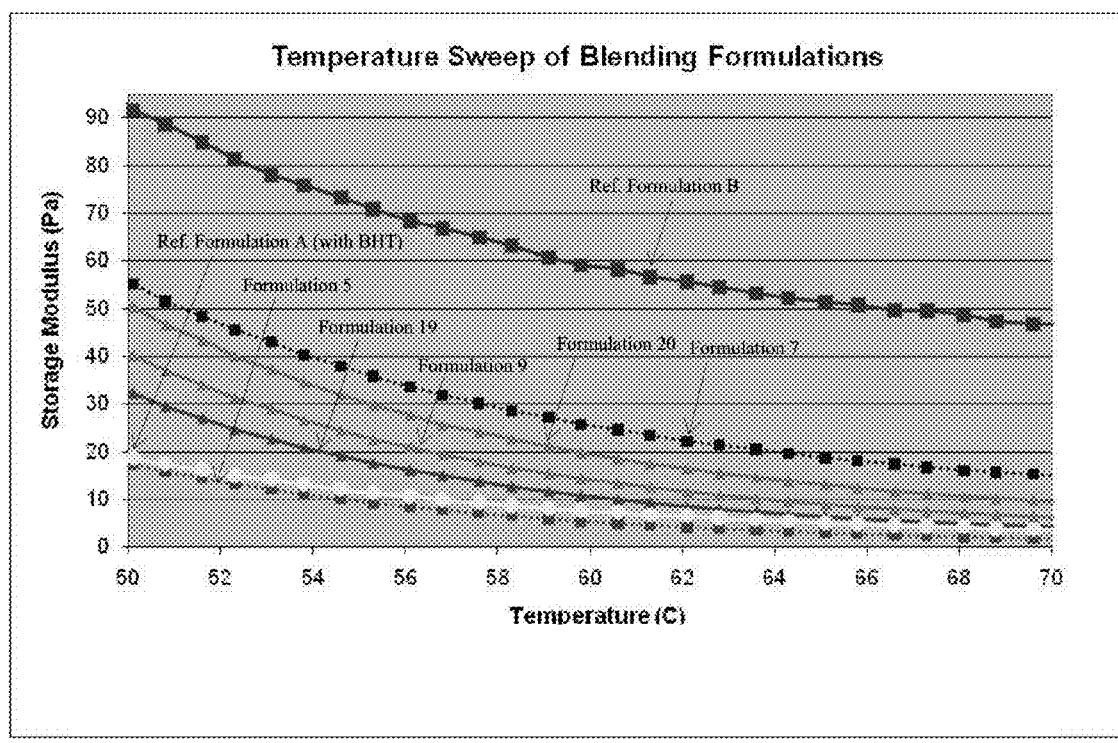
FIG. 32 is a graph showing storage modulus (G') as a function of temperature for Reference Formulation A and Formulations 5, 7, 9, 19 and 20.
Figure 33:
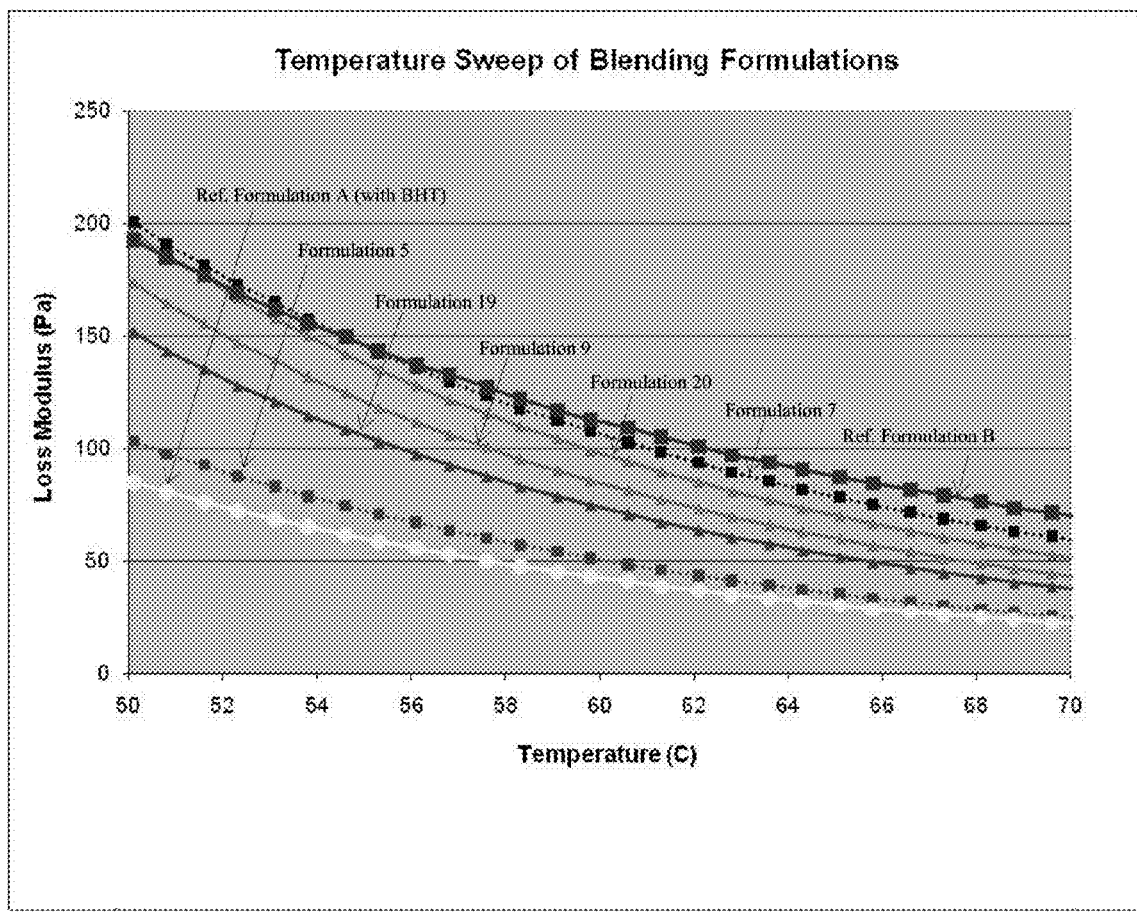
FIG. 33 is a graph showing loss modulus (G") as a function of temperature for Reference Formulation A and Formulations 5, 7, 9, 19 and 20.
Figure 34:
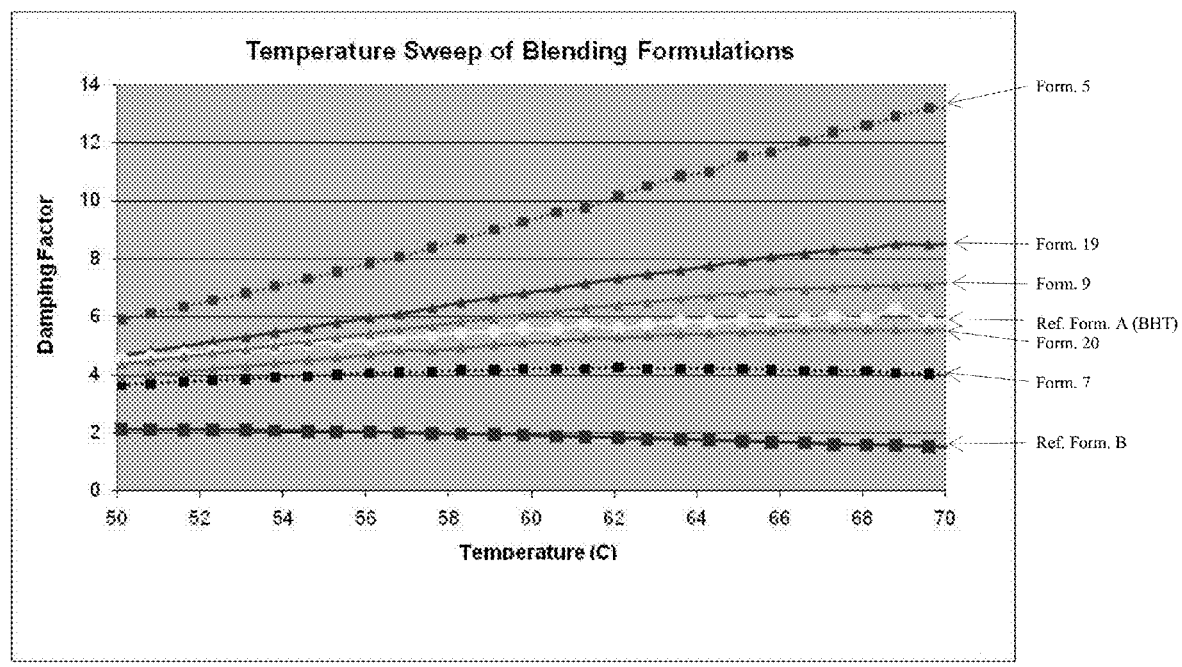
FIG. 34 is a graph showing damping factor (G"/G') as a function of temperature for Reference Formulation A and Formulations 5, 7, 9, 19 and 20.
Figure 35:
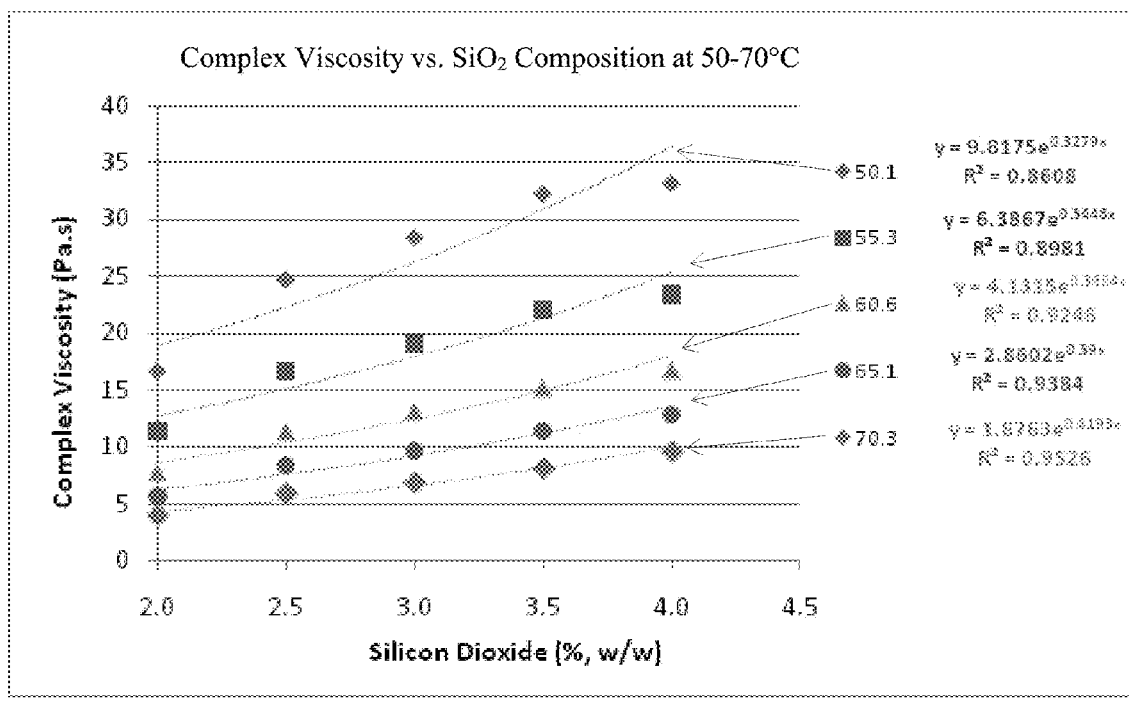
FIG. 35 provides graphs showing complex viscosity (Panel A) and storage modulus (Panel B) as a function of $SiO_2$ content at temperatures between about 50 and 70° C. based on the results for Formulations 5, 7, 9, 19 and 20.
Figure 35:
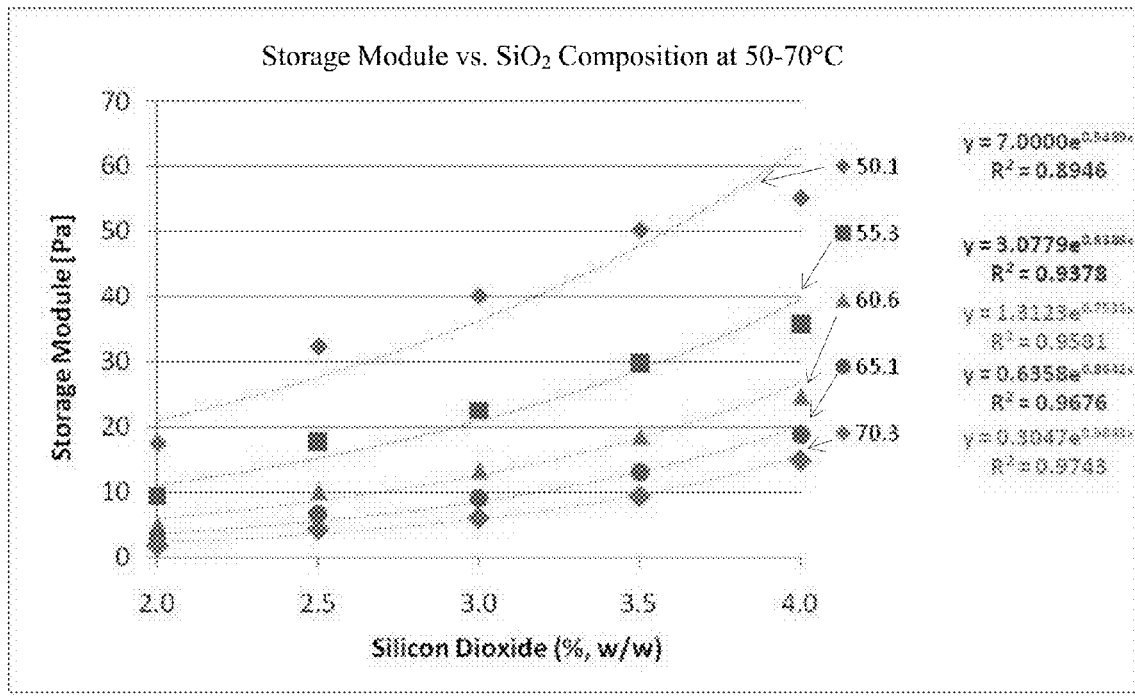
Figure 36:
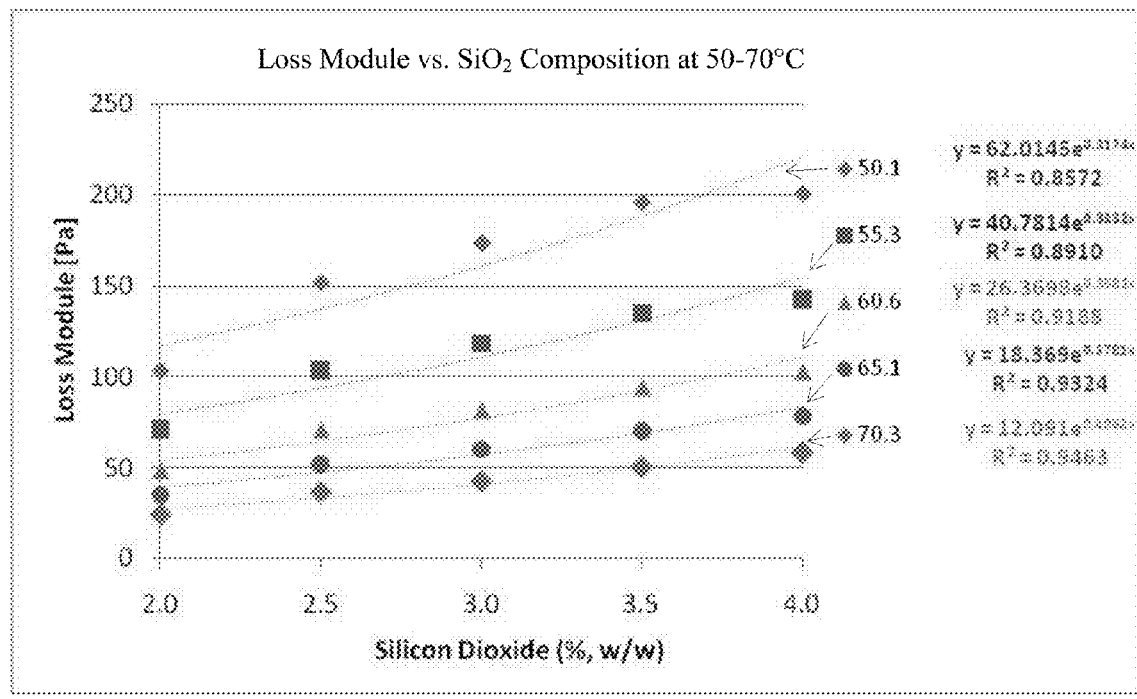
FIG. 36 provides graphs showing loss modulus (Panel A) and damping factor (Panel B) as a function of $SiO_2$ content at temperatures between about 50 and 70° C. based on the results for Formulations 5, 7, 9, 19 and 20.
Figure 36:
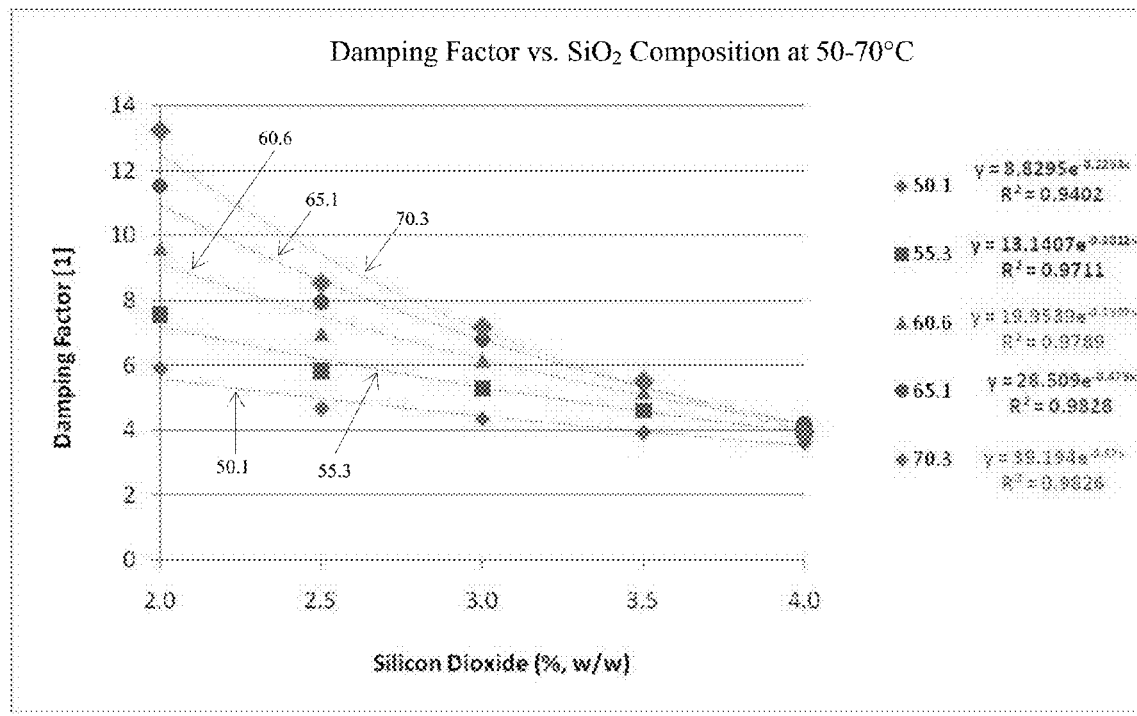

The viscoelastic outputs of the rheology testing experiments are provided in Tables 27-30 (below) and FIGS. 26-32. As shown in Table 27 and FIGS. 30 and 31, the complex viscosity range for the tested compositions narrows with an increase in temperature. In addition, there is an increase in complex viscosity with increasing concentration of SiO₂ for Formulations 5, 7, 9, 19 and 20 as shown in FIGS. 30, 31 and 35 (Panel A).

TABLE 27

Complex Viscosity

| Temp. (° C.) | Formulation 5 | Formulation 19 | Formulation 9 | Formulation 20 | Formulation 7 |
|---|---|---|---|---|---|
| 50 | 17 | 25 | 28 | 32 | 33 |
| 55 | 11 | 17 | 19 | 22 | 23 |
| 61 | 8 | 11 | 13 | 15 | 17 |
| 65 | 6 | 8 | 10 | 11 | 13 |
| 70 | 4 | 6 | 7 | 8 | 10 |

TABLE 28

Loss Module (G")

| Temp. (° C.) | Formulation 5 | Formulation 19 | Formulation 9 | Formulation 20 | Formulation 7 |
|---|---|---|---|---|---|
| 50 | 103 | 152 | 174 | 196 | 201 |
| 55 | 71 | 103 | 118 | 135 | 143 |
| 61 | 49 | 71 | 82 | 94 | 103 |
| 65 | 35 | 52 | 60 | 70 | 78 |
| 70 | 25 | 37 | 43 | 50 | 58 |

TABLE 29

Damping Factor (G"/G')

| Temp. (° C.) | Formulation 5 | Formulation 19 | Formulation 9 | Formulation 20 | Formulation 7 |
|---|---|---|---|---|---|
| 50 | 5.9 | 4.7 | 4.4 | 3.9 | 3.6 |
| 55 | 7.6 | 5.8 | 5.3 | 4.6 | 4.0 |
| 61 | 9.6 | 7.0 | 6.2 | 5.2 | 4.2 |
| 65 | 11.5 | 7.9 | 6.8 | 5.5 | 4.2 |
| 70 | 13.2 | 8.5 | 7.2 | 5.5 | 4.0 |

TABLE 30

Storage Module (G')

| Temp. (° C.) | Formulation 5 | Formulation 19 | Formulation 9 | Formulation 20 | Formulation 7 |
|---|---|---|---|---|---|
| 50 | 17 | 32 | 40 | 50 | 55 |
| 55 | 9 | 18 | 23 | 30 | 36 |
| 61 | 5 | 10 | 13 | 19 | 25 |

TABLE 30-continued

Storage Module (G')

| Temp. (° C.) | Formulation 5 | Formulation 19 | Formulation 9 | Formulation 20 | Formulation 7 |
|---|---|---|---|---|---|
| 65 | 3 | 7 | 9 | 13 | 19 |
| 70 | 2 | 4 | 6 | 9 | 15 |

Formulations 19, 9, 20 and 7, with increased concentration of SiO₂ (as compared to Formulation 5), exhibited higher elastic property (lower G"/G') as shown in Tables 27-30 and FIGS. 32-36. Without intending to be bound by any particular theory, this higher elastic property may have resulted in the lower inter-capsule dissolution variability shown in FIGS. 27 and 29.

Example 14: Stability Analysis of Stored Extended Release Oxycodone Compositions (Formulations 5, 8, 9 and 7)

Formulations 5, 8, 9 and 7 were analyzed following storage for various periods of time to determine the effect on drug release and inter-capsule dissolution variability.

Materials and Methods

Formulations 5, 8, 9 and 7 (40 mg oxycodone) were stored at 25° C./60% RH and/or 40° C./75% RH for a total of 6 months, 2 months, 2 months, and 3 months respectively. Twelve capsules from each composition lot were tested according to the testing conditions discussed above to evaluate the effect on mean release and inter-capsule dissolution variability.

Results

Figure 37:
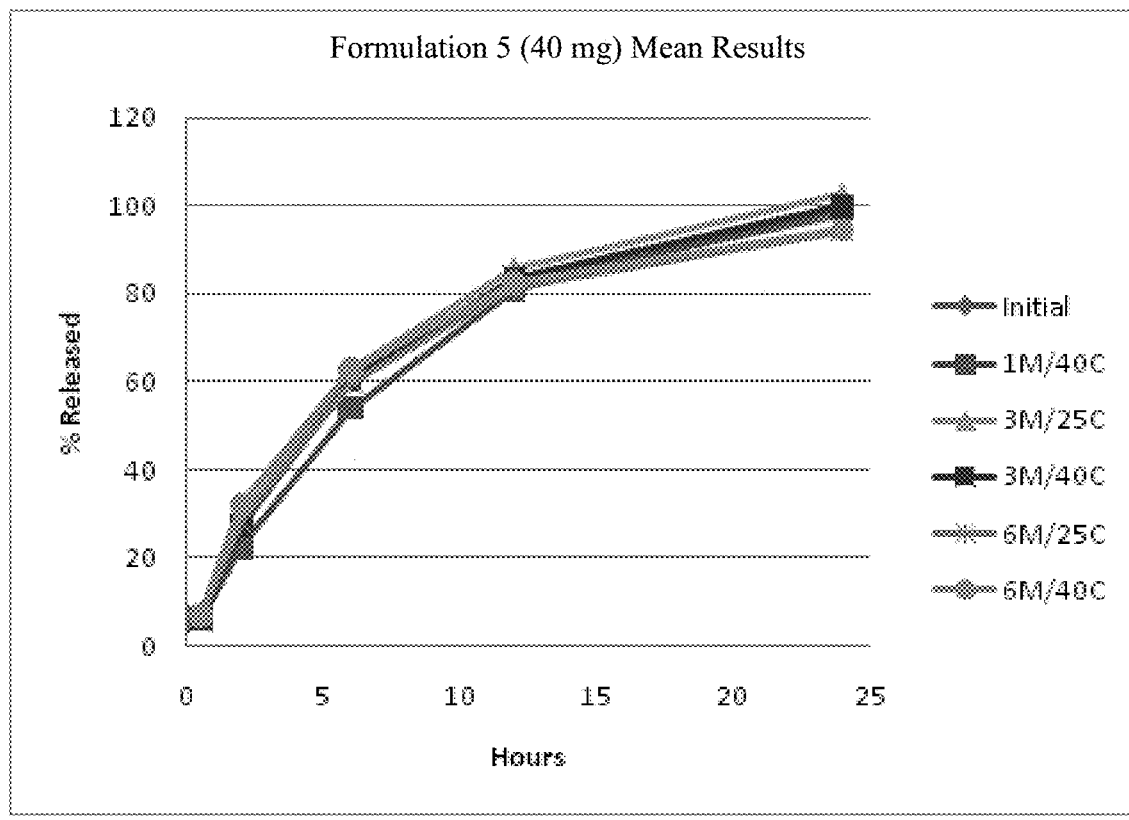
FIG. 37 is a graph showing mean release for Formulation 5 (40 mg) following storage at 25° C./60% relative humidity (RH) and 40° C./75% RH for up to 6 months.

The results for Formulation 5 are provided in FIG. 37 and Table 31 (below). No significant change in mean release was seen as a result of storage up to 6 months for Formulation 5. Formulation 5 testing resulted in a relatively higher level of dissolution sample variation than that seen for Formulations 9 and 7 (discussed below).

TABLE 31

| Time Point (Months) | Storage Condition | Sample No. | | 0.5 | 2 | 6 | 12 | 24 | Sp |
|---|---|---|---|---|---|---|---|---|---|
| 0 | N/A | 12 | Mean | 7 | 29 | 61 | 83 | 98 | 5 |
| | | | SD | 1 | 4 | 7 | 6 | 3 | |
| 1 | 40° C./75% RH | 12 | Mean | 6 | 22 | 54 | 81 | 100 | 3 |
| | | | SD | 1 | 3 | 5 | 4 | 3 | |
| 3 | 25° C./60% RH | 12 | Mean | 7 | 29 | 63 | 86 | 103 | 4 |
| | | | SD | 1 | 3 | 5 | 6 | 4 | |
| | 40° C./75% RH | 12 | Mean | 6 | 27 | 60 | 84 | 100 | 4 |
| | | | SD | 1 | 3 | 6 | 6 | 4 | |
| 6 | 25° C./60% RH | 12 | Mean | 7 | 28 | 60 | 81 | 95 | 4 |
| | | | SD | 1 | 3 | 6 | 6 | 3 | |
| | 40° C./75% RH | 12 | Mean | 7 | 32 | 63 | 83 | 95 | 3 |
| | | | SD | 1 | 3 | 5 | 4 | 2 | |

Figure 38:
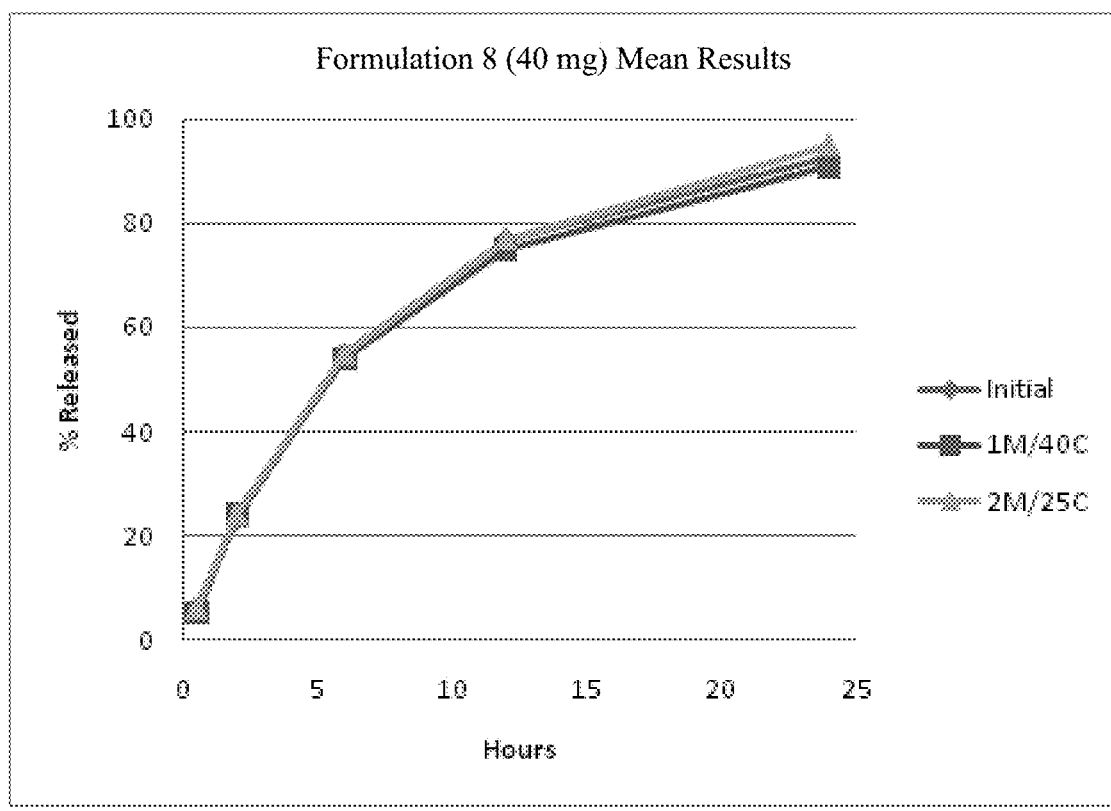
FIG. 38 is a graph showing mean release for Formulation 8 (40 mg) following storage for 1 month at 40° C./75% RH or 2 months at 25° C./60% RH.

The results for Formulation 8 are provided in FIG. 38 and Table 32 below. No significant change in mean release was seen as a result of storage up to 2 months for Formulation 8. Formulation 8 testing resulted in a relatively higher level of variation than that seen for Formulations 9 and 7 (discussed below).

TABLE 32

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 6 | 23 | 55 | 77 | 93 | 5 |
| | | | SD | 1 | 5 | 8 | 6 | 4 | |
| 1 | 40° C./75% RH | 12 | Mean | 5 | 24 | 54 | 75 | 91 | 4 |
| | | | SD | 1 | 3 | 5 | 5 | 3 | |
| 2 | 25° C./60% RH | 12 | Mean | 5 | 24 | 55 | 77 | 95 | 4 |
| | | | SD | 1 | 4 | 6 | 5 | 3 | |

Figure 39:
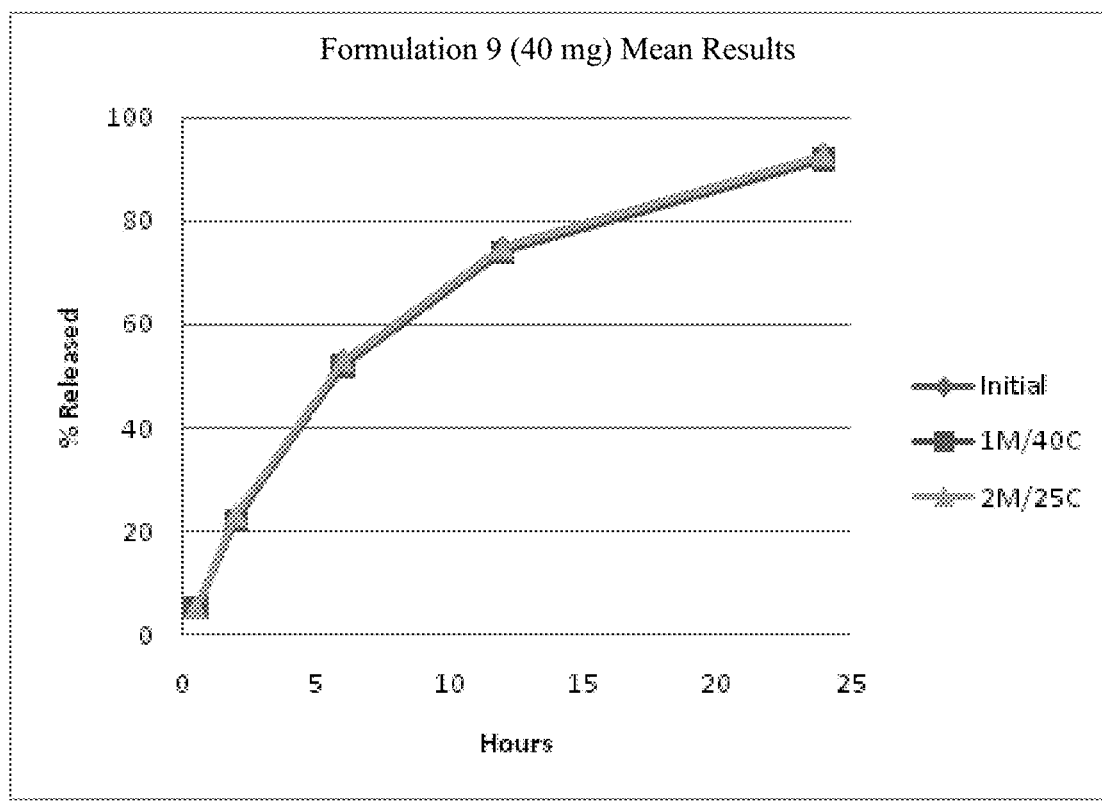
FIG. 39 is a graph showing mean release for Formulation 9 (40 mg) following storage for 1 month at 40° C./75% RH or 2 months at 25° C./60% RH.

The results for Formulation 9 are provided in FIG. 39 and Table 33 below. No significant change in mean release was seen as a result of storage for up to 2 months for Formulation 9. In addition, Formulation 9 showed a relatively low level of inter-capsule dissolution variability following storage for a 1 month period.

TABLE 33

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 5 | 22 | 53 | 75 | 93 | 2 |
| | | | SD | 1 | 1 | 2 | 2 | 2 | |
| 1 | 40° C./75% RH | 12 | Mean | 5 | 22 | 52 | 74 | 92 | 2 |
| | | | SD | 0 | 1 | 2 | 2 | 1 | |
| 2 | 25° C./60% RH | 12 | Mean | 5 | 23 | 53 | 75 | 93 | 1 |
| | | | SD | 1 | 1 | 2 | 2 | 1 | |

Figure 40:
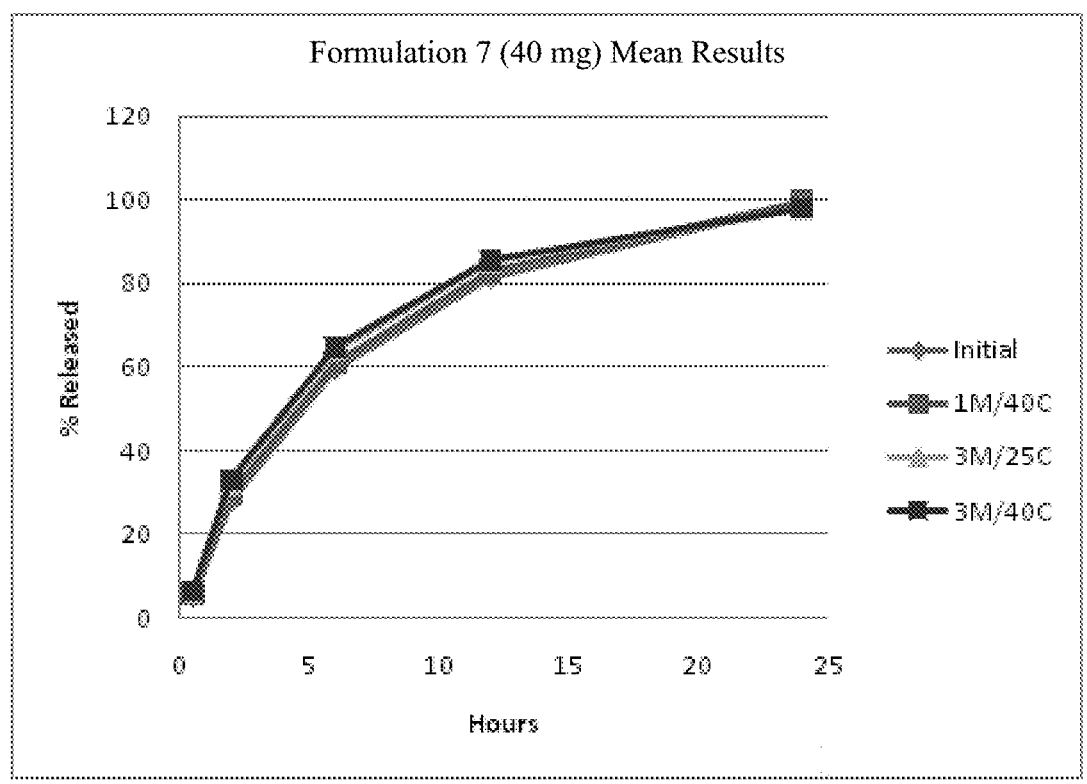
FIG. 40 is a graph showing mean release for Formulation 7 (40 mg) following storage for 1 month at 40° C./75% RH or 3 months at 25° C./60% RH or 40° C./75% RH.

The results for Formulation 7 are provided in FIG. 40 and Table 34 below. No significant change in mean release was seen as a result of storage for up to 3 months for Formulation 7. In addition, Formulation 7 showed a relatively low level of inter-capsule dissolution variability following storage for up to three months.

TABLE 34

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 5 | 28 | 59 | 82 | 99 | 2 |
| | | | SD | 1 | 1 | 2 | 3 | 3 | |
| 1 | 40° C./75% RH | 12 | Mean | 6 | 30 | 61 | 83 | 100 | 2 |
| | | | SD | 1 | 2 | 2 | 2 | 2 | |

TABLE 34-continued

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 3 | 25° C./60% RH | 12 | Mean | 6 | 32 | 64 | 85 | 98 | 2 |
| | | | SD | 0 | 1 | 2 | 3 | 3 | |
| | 40° C./75% RH | 12 | Mean | 6 | 33 | 65 | 86 | 98 | 2 |
| | | | SD | 0 | 1 | 2 | 2 | 3 | |

The initial T=0 dissolution data from Tables 31-34 was used to calculate % RSD ((SD/mean)×100) for Formulations 5, 8, 9 and 7. The results are provided below in Table 35. As shown below, Formulations 9 and 7 exhibited a % RSD of 5% or less at the 2 and 6 hour time points, while Formulations 5 exhibited a % RSD of less than 15% at the 2 and 6 hour time points. Formulation 8 exhibited a % RSD of less than 25% at the 2 and 6 hour time points.

TABLE 35

| ID | SiO$_2$ (%) | Sample # | | Time point (hrs) | | | | |
|---|---|---|---|---|---|---|---|---|
| | | | | 0.5 | 2 | 6 | 12 | 24 |
| 5 | 1.90 | 12 | Mean | 7 | 29 | 61 | 83 | 98 |
| | | | SD | 1 | 4 | 7 | 6 | 3 |
| | | | % RSD | 14 | 14 | 11 | 7 | 3 |
| 8 | 2.50 | 12 | Mean | 6 | 23 | 55 | 77 | 93 |
| | | | SD | 1 | 5 | 8 | 6 | 4 |
| | | | % RSD | 17 | 22 | 15 | 8 | 4 |
| 9 | 2.90 | 12 | Mean | 5 | 22 | 53 | 75 | 93 |
| | | | SD | 1 | 1 | 2 | 2 | 2 |
| | | | % RSD | 20 | 5 | 4 | 3 | 2 |
| 7 | 3.90 | 12 | Mean | 5 | 28 | 59 | 82 | 99 |
| | | | SD | 1 | 1 | 2 | 3 | 3 |
| | | | % RSD | 20 | 4 | 3 | 4 | 3 |

Example 15: Preparation and Analysis of Extended Release Hydrocodone Compositions (Formulations 21-26)

Hydrocodone compositions (Formulations 21-26) were prepared and characterized with respect to inter-capsule dissolution variability as indicated below.

Materials and Methods

The compositions were prepared to provide the compositions indicated in Table 36 (below). Composition components were blended and individual compositions were encapsulated in gelatin (Licaps® (GC)) or HPMC (Vcaps® (VC)) capsules as described above.

TABLE 36

| | Composition (% w/w unless otherwise noted) | | | | | |
|---|---|---|---|---|---|---|
| | Formulation 21 | Formulation 22 | Formulation 23 | Formulation 24 | Formulation 25 | Formulation 26 |
| Hydrocodone Bitartrate | 13.64 | 13.64 | 13.64 | 10.00 | 10.00 | 10.00 |
| SAIB | 36.64 | 35.99 | 35.61 | 38.50 | 37.84 | 37.45 |
| Triacetin | 34.89 | 34.94 | 34.92 | 36.67 | 36.73 | 36.72 |
| IPM | 2.50 | 2.50 | 2.50 | 2.50 | 2.50 | 2.50 |
| CAB | 4.74 | 4.74 | 4.74 | 4.74 | 4.74 | 4.74 |
| HEC | 5.69 | 5.69 | 5.69 | 5.69 | 5.69 | 5.69 |
| Cab-O-Sil | 1.90 | 2.50 | 2.90 | 1.90 | 2.50 | 2.90 |
| Capsule Shell | GC, VC | GC, VC | GC, VC | VC | VC | VC |

Six capsules from each composition lot were tested according to the testing conditions discussed above to evaluate the effect on inter-capsule dissolution variability.

Results

The results of the dissolution experiments are provided in Table 37 (below). A clear trend with respect to inter-capsule dissolution variability and $SiO_2$ concentration was not demonstrated. However, inter-capsule dissolution variability was reduced for each composition when formulated in HPMC capsules as opposed to gelatin capsules. Formulation 23 with 2.9% $SiO_2$ showed the least amount of inter-capsule dissolution variability.

The HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 67% Mobile phase A and 33% Mobile phase B; 210 nm wavelength.

TABLE 38

| Composition (% w/w) | Formulation 27 | Formulation 28 | Formulation 29 | Formulation 30 |
|---|---|---|---|---|
| D-Amphetamine Sulfate | 10.00 | 10.00 | 10.00 | 10.00 |

TABLE 37

| Formulation ID | $SiO_2$ (% w/w) | Capsule Shell | Sample # | | Time point (hrs) | | | | | | | Sp |
|---|---|---|---|---|---|---|---|---|---|---|---|---|
| | | | | | 0.5 | 2 | 3 | 6 | 12 | 18 | 24 | |
| Formulation 21 | 1.90 | GC | 6 | Mean | 15 | 60 | 75 | 95 | 101 | 102 | 102 | 6 |
| | | | | SD | 4 | 9 | 9 | 5 | 4 | 4 | 4 | |
| | | VC | 6 | Mean | 13 | 59 | 74 | 95 | 102 | 102 | 102 | 4 |
| | | | | SD | 2 | 6 | 6 | 3 | 2 | 2 | 2 | |
| Formulation 22 | 2.50 | GC | 6 | Mean | 15 | 52 | 66 | 90 | 100 | 102 | 102 | 9 |
| | | | | SD | 4 | 12 | 12 | 8 | 7 | 7 | 7 | |
| | | VC | 6 | Mean | 11 | 45 | 69 | 94 | 103 | 104 | 105 | 5 |
| | | | | SD | 2 | 5 | 7 | 6 | 4 | 4 | 4 | |
| Formulation 23 | 2.90 | GC | 6 | Mean | 16 | 52 | 67 | 91 | 101 | 103 | 103 | 5 |
| | | | | SD | 5 | 8 | 7 | 3 | 3 | 3 | 3 | |
| | | VC | 6 | Mean | 10 | 50 | 66 | 92 | 101 | 101 | 102 | 2 |
| | | | | SD | 2 | 4 | 4 | 1 | 2 | 1 | 1 | |
| Formulation 24 | 1.90 | VC | 6 | Mean | 5 | 42 | 58 | 84 | 99 | 100 | 101 | 4 |
| | | | | SD | 1 | 3 | 4 | 4 | 5 | 4 | 4 | |
| Formulation 25 | 2.50 | VC | 6 | Mean | 9 | 45 | 59 | 84 | 100 | 103 | 103 | 4 |
| | | | | SD | 2 | 5 | 5 | 3 | 3 | 3 | 3 | |
| Formulation 26 | 2.90 | VC | 6 | Mean | 13 | 53 | 66 | 88 | 101 | 103 | 103 | 5 |
| | | | | SD | 3 | 7 | 7 | 6 | 4 | 4 | 4 | |

Example 16: Preparation and Analysis of Extended Release Amphetamine Compositions (Formulations 27-30)

Amphetamine compositions (Formulations 27-30) were prepared and characterized with respect to inter-capsule dissolution variability as indicated below.

Materials and Methods

The compositions were prepared to provide the compositions indicated in Table 38 (below). Composition components were blended and individual compositions were encapsulated in HPMC (Vcaps® (VC)) capsules as described above.

Dissolution experiments were performed using 2-phase medium in a USP Apparatus 2. The capsules were placed in stainless steel (316SS) wire spiral capsule sinkers for dissolution testing. The dissolution parameters were as follows: Dissolution medium: 750 ml 0.1N HCl for the first 2 hours, add 200 ml 0.19M phosphate buffer to achieve a final pH of 6.0; Paddle speed: 50 rpm; Vessel temperature: 37 C. Sampling time points: 0.25, 0.5, 1, 1.5, 2, 3, 6, 9, 12 and 24 hours. Sampling volume: 1 mL.

TABLE 38-continued

| Composition (% w/w) | Formulation 27 | Formulation 28 | Formulation 29 | Formulation 30 |
|---|---|---|---|---|
| SAIB | 38.50 | 37.84 | 37.45 | 36.59 |
| Triacetin | 36.67 | 36.73 | 36.72 | 36.59 |
| IPM | 2.50 | 2.50 | 2.50 | 2.50 |
| CAB | 4.74 | 4.74 | 4.74 | 4.74 |
| HEC | 5.69 | 5.69 | 5.69 | 5.69 |
| Cab-O-Sil | 1.90 | 2.50 | 2.90 | 3.90 |
| Capsule Shell | VC | VC | VC | VC |

Results

The results of the dissolution experiments are provided in Table 39 (below).

TABLE 39

| Formulation ID | $SiO_2$ (%) | Capsule Shell | Sample # | | Time point (hrs) | | | | | | | | | | Sp |
|---|---|---|---|---|---|---|---|---|---|---|---|---|---|---|---|
| | | | | | 0.25 | 0.5 | 1 | 1.5 | 2 | 3 | 6 | 9 | 12 | 24 | |
| Formulation 27 | 1.90 | VC | 6 | Mean | 4 | 11 | 22 | 30 | 38 | 50 | 76 | 94 | 100 | 106 | 4 |
| | | | | SD | 0 | 1 | 2 | 2 | 3 | 4 | 4 | 5 | 2 | 3 | |
| Formulation 28 | 2.50 | VC | 6 | Mean | 4 | 12 | 23 | 33 | 41 | 52 | 79 | 93 | 100 | 104 | 3 |
| | | | | SD | 1 | 1 | 1 | 1 | 1 | 2 | 2 | 2 | 2 | 5 | |

TABLE 39-continued

| Formulation ID | SiO$_2$ (%) | Capsule Shell | Sample # | | Time point (hrs) | | | | | | | | | | Sp |
|---|---|---|---|---|---|---|---|---|---|---|---|---|---|---|---|
| | | | | | 0.25 | 0.5 | 1 | 1.5 | 2 | 3 | 6 | 9 | 12 | 24 | |
| Formulation 29 | 2.90 | VC | 6 | Mean | 4 | 12 | 25 | 36 | 46 | 58 | 84 | 99 | 105 | 108 | 2 |
| | | | | SD | 0 | 1 | 0 | 1 | 1 | 1 | 1 | 1 | 2 | 2 | |
| Formulation 30 | 3.90 | VC | 6 | Mean | 5 | 14 | 28 | 39 | 48 | 61 | 88 | 101 | 106 | 108 | 5 |
| | | | | SD | 1 | 2 | 3 | 3 | 4 | 4 | 4 | 3 | 4 | 4 | |

Example 17: Preparation and Analysis of Extended Release Methylphenidate Compositions (Formulations 30-33)

Methylphenidate compositions (Formulations 31-34) were prepared and characterized with respect to inter-capsule dissolution variability as indicated below.

Materials and Methods

The compositions were prepared to provide the compositions indicated in Table 40 (below). Composition components were blended and individual compositions were encapsulated in HPMC (Vcaps® (VC)) capsules as described above.

Dissolution experiments were performed using 2-phase medium in a USP Apparatus 2. The capsules were placed in stainless steel (316SS) wire spiral capsule sinkers for dissolution testing. The dissolution parameters were as follows:

Dissolution medium: 750 ml 0.1N HCl for the first 2 hours, add 200 ml 0.19M phosphate buffer to achieve a final pH of 6.0; Paddle speed: 50 rpm; Vessel temperature: 37 C. Sampling time points: 0.25, 0.5, 1, 1.5, 2, 3, 6, 9, 12 and 24 hours. Sampling volume: 1 mL.

The HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 71% Mobile phase A and 29% Mobile phase B; 210 nm wavelength.

TABLE 40

| Composition (% w/w) | Formulation 31 | Formulation 32 | Formulation 33 | Formulation 34 |
|---|---|---|---|---|
| Methylphenidate HCl | 20.00 | 20.00 | 20.00 | 20.00 |
| SAIB | 33.38 | 32.76 | 32.40 | 31.59 |
| Triacetin | 31.79 | 31.81 | 31.77 | 31.59 |
| IPM | 2.50 | 2.50 | 2.50 | 2.50 |
| CAB | 4.74 | 4.74 | 4.74 | 4.74 |
| HEC | 5.69 | 5.69 | 5.69 | 5.69 |
| Cab-O-Sil | 1.90 | 2.50 | 2.90 | 3.90 |
| Capsule Shell | VC | VC | VC | VC |

Results

The results of the dissolution experiments are provided in Table 41 (below).

TABLE 41

| Formulation ID | SiO$_2$ (%) | Capsule Shell | Sample # | | Time point (hrs) | | | | | | | | | | Sp |
|---|---|---|---|---|---|---|---|---|---|---|---|---|---|---|---|
| | | | | | 0.25 | 0.5 | 1 | 1.5 | 2 | 3 | 6 | 9 | 12 | 24 | |
| Formulation 31 | 1.90 | VC | 6 | Mean | 3 | 11 | 24 | 34 | 42 | 55 | 82 | 95 | 100 | 103 | 2 |
| | | | | SD | 1 | 1 | 1 | 2 | 2 | 2 | 2 | 2 | 2 | 2 | |
| Formulation 32 | 2.50 | VC | 6 | Mean | 4 | 12 | 27 | 38 | 48 | 61 | 89 | 100 | 102 | 104 | 2 |
| | | | | SD | 1 | 1 | 2 | 2 | 2 | 2 | 2 | 1 | 1 | 1 | |
| Formulation 33 | 2.90 | VC | 6 | Mean | 4 | 14 | 29 | 41 | 51 | 65 | 92 | 101 | 104 | 105 | 2 |
| | | | | SD | 1 | 2 | 1 | 1 | 1 | 1 | 1 | 2 | 2 | 3 | |
| Formulation 34 | 3.90 | VC | 6 | Mean | 4 | 14 | 30 | 42 | 52 | 66 | 92 | 99 | 102 | 103 | 2 |
| | | | | SD | 1 | 2 | 2 | 2 | 1 | 1 | 2 | 2 | 2 | 2 | |

What is claimed is:

1. A method for treating pain in a subject, the method comprising:
   orally administering to the subject a composition comprising:
   oxycodone;
   sucrose acetate isobutyrate (SAIB), wherein the SAIB is present in the composition in an amount from about 35% by weight to about 45% by weight relative to the total weight of the composition;
   triacetin, wherein the triacetin is present in the composition in an amount from about 31% by weight to about 45% by weight relative to the total weight of the composition;
   isopropyl myristate (IPM), wherein the IPM is present in the composition in an amount from about 2% by weight to about 10% by weight relative to the total weight of the composition;
   cellulose acetate butyrate (CAB), wherein the CAB is present in the composition at about 2% to about 10% by weight relative to the total weight of the composition;
   hydroxyethyl cellulose (HEC), wherein the HEC is present in the composition in an amount from about 2% by weight to about 7% by weight relative to the total weight of the composition; and
   silicon dioxide, wherein the silicon dioxide is present in the composition in an amount from 2.4% by weight to about 4.0% by weight relative to the total weight of the composition, wherein the composition is formulated for oral administration, and one or more symptoms or signs associated with the subject's pain is alleviated.

2. The method of claim 1, wherein the composition comprises about 38% by weight to about 41% by weight of the triacetin relative to the total weight of the composition.

3. The method of claim 1, wherein the composition comprises about 2% by weight to about 3% by weight of the IPM relative to the total weight of the composition.

4. The method of claim 1, wherein the CAB has a number average molecular weight ranging from 66,000 Daltons to 83,000 Daltons.

5. The method of claim 1, wherein the CAB has at least one feature selected from a butyryl content ranging from about 17% to about 38%, an acetyl content ranging from about 13% to about 30%, and a hydroxyl content ranging from about 0.8% to about 1.7%.

6. The method of claim 1, wherein the silicon dioxide is present in the composition in an amount from about 2.5% by weight to about 3.2% by weight relative to the total weight of the composition.

7. The method of claim 1, wherein the silicon dioxide is present in the composition in an amount from about 2.5% by weight to about 3.0% by weight relative to the total weight of the composition.

8. The method of claim 1, wherein the silicon dioxide is present in the composition in an amount from about 2.5% by weight to about 2.9% by weight relative to the total weight of the composition.

9. The method of claim 1, wherein:

the composition comprises about 38% by weight to about 41% by weight of the triacetin relative to the total weight of the composition, the composition comprises about 2% by weight to about 3% by weight of the IPM relative to the total weight of the composition, the CAB has a number average molecular weight ranging from 66,000 Daltons to 83,000 Daltons, the CAB has at least one feature selected from a butyryl content ranging from about 17% to about 38%, an acetyl content ranging from about 13% to about 30%, and a hydroxyl content ranging from about 0.8% to about 1.7%, and the silicon dioxide is present in the composition in an amount from about 2.5% by weight to about 3.0% by weight relative to the total weight of the composition.

10. The method of claim 1, wherein the composition is administered no more than twice in a 24-hour period.

11. The method of claim 1, wherein the subject is a human.

\* \* \* \* \*